(12) United States Patent
Mussmann et al.

(10) Patent No.: US 11,624,059 B2
(45) Date of Patent: *Apr. 11, 2023

(54) DETERGENT COMPOSITIONS COMPRISING GH9 ENDOGLUCANASE VARIANTS II

(71) Applicant: Henkel AG & Co. KGaA, Duesseldorf (DE)

(72) Inventors: Nina Mussmann, Willich (DE); Susanne Wieland, Dormagen/Zons (DE); Christian Degering, Erkrath (DE); Rune Nygaard Monrad, Hilleroed (DK); Vasudeva P. Rao, Karnataka (IN); Rajendra Kulothungan Sainathan, Bangalore (IN); Sohel Dalal, Ahmedabad (IN); Santhosh Vasu Mepadam, Bangalore (IN); Allan Svendsen, Hoersholm (DK); Mette Louise Dissing Overgaard, Copenhagen (DK); Lars Anderson, Malmoe (SE); Geetha Hiremath Mendez, Bangalore (IN)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/638,798

(22) PCT Filed: Aug. 3, 2018

(86) PCT No.: PCT/EP2018/071105
§ 371 (c)(1),
(2) Date: Feb. 13, 2020

(87) PCT Pub. No.: WO2019/038059
PCT Pub. Date: Feb. 28, 2019

(65) Prior Publication Data
US 2020/0239815 A1    Jul. 30, 2020

(30) Foreign Application Priority Data

Aug. 24, 2017   (DE) .................... 10 2017 214 809.8

(51) Int. Cl.
*C12N 9/42*   (2006.01)
*C11D 3/386*   (2006.01)
*C11D 11/00*   (2006.01)

(52) U.S. Cl.
CPC ........ *C12N 9/2437* (2013.01); *C11D 3/38636* (2013.01); *C11D 11/0017* (2013.01); *C12Y 302/01004* (2013.01)

(58) Field of Classification Search
CPC .................................................... C12N 9/2437
See application file for complete search history.

(56) References Cited

U.S. PATENT DOCUMENTS

| 9,458,441 B2* | 10/2016 | Segura | C09K 8/52 |
| 9,988,616 B2* | 6/2018 | Segura | C11D 3/38636 |
| 10,988,747 B2* | 4/2021 | Mussmann | C11D 3/38645 |
| 2015/0132824 A1* | 5/2015 | Segura | C09K 8/52 |
| | | | 435/209 |
| 2017/0073656 A1 | 3/2017 | Segura et al. | |
| 2017/0175096 A1 | 6/2017 | Jensen et al. | |

FOREIGN PATENT DOCUMENTS

| WO | 2013167581 A1 | 11/2013 |
| WO | 2015001017 A2 | 1/2015 |
| WO | 2018037062 A1 | 3/2018 |
| WO | 2018037065 A1 | 3/2018 |

OTHER PUBLICATIONS

Studer. Residue mutations and their impact on protein structure and function: detecting beneficial and pathogenic changes. Biochem. J. (2013) 449, 581-594.*
International search report from parallel PCT Patent Application PCT/EP2018/071105 dated Nov. 15, 2018, 11 pages (for reference purposes only).
Moroz et al., "Structural Dynamics and Catalytic Properties of a Multi-Modular Xanthanase", ACS Catalysis, 2018, 30 pages, vol. 8, No. 7.
Santos et al., "Dissecting structure-function-stability relationships of a thermostable GH5-CBM3 cellulase from Bacillus subtilis 168", Biochemical Journal, 2012, 15 pages, vol. 441, The Authors Journal compilation/Biochemical Society.
Hamuro et al., Rapid Analysis of Protein Structure and Dynamics by Hydrogen/Deuterium Exchange Mass Spectrometry, Journal of Biomolecular Techniques, Sep. 2003, pp. 171-182, vol. 14, Issue 3.
Ruijssenaars et al., "A Pyruvated Mannose-Specific Xanthan Lyase Involved in Xanthan Degradation by Paenibacillus alginolyticus XL-1", Applied and Environmental Microbiology, Jun. 1999, pp. 2446-2452, vol. 65, No. 6, American Society for Microbiology.

(Continued)

*Primary Examiner* — Yong D Pak
(74) *Attorney, Agent, or Firm* — Viering Jentschura & Partner mbB

(57) ABSTRACT

Detergent compositions may include endoglucanase variants and methods of using such detergent compositions. The endoglucanase may have an alteration at one or more positions where the variant has at least 60% but less than 100% sequence identity to SEQ ID NO: 2.

12 Claims, No Drawings
Specification includes a Sequence Listing.

(56) References Cited

OTHER PUBLICATIONS

Ruijssenaars et al., "A Novel Gene Encoding Xanthan Lyase of Paenibacillus alginolyticus Strain XL-1", Applied and Environmental Microbiology, Sep. 2000, pp. 3945-3950, vol. 66, No. 9, American Society for Microbiology.
Alignment of SEQ ID No. 2 of US20170073656 to SEQ ID No. 2 of the instant application (Year: 2017).
Ruijssenaars et al., 1999, Appl Environ Microbiol, vol. 65, No. 6, pp. 2446-2452.
Ruijssenaars et al., 2000, Appl Environ Microbiol, vol. 66, No. 9, pp. 3945-3950.
Non-Final Office Action from parallel U.S. Appl. No. 16/636,550 dated Aug. 19, 2021, 17 pages, for information purpose only.

\* cited by examiner

SEQUENCE LISTING

```
<160> NUMBER OF SEQ ID NOS: 4

<210> SEQ ID NO 1
<211> LENGTH: 12110
<212> TYPE: DNA
<213> ORGANISM: Paenibacillus sp-62047

<400> SEQUENCE: 1
tctggttgtt ttcttcattt caggtttcgc cctttccttg ccaaatataa gaaaaacggc      60
gttccgataa tcgcggtgac ggtgattcat aaggaaatgc aatccatctg gccagaacat     120
ctgcgtacac cagcaaaatg gcaccgaaca gtgccgaaaa cggaagcacg tattgataat     180
gttctccgat cagcttgcgg acaatatgcg ggacgagcag cccgacaaag ccaatcggcc     240
cggcgacggc tacggaagcg ccggaaagaa ttaaaataat caaactgatc agaatcctga     300
tgccgttcat attttgtcca agcccttttg ctgtttcgtc tccgagaccg agaacagaaa     360
cagaaccgga aaatacgagg gcaagcccga tgccaatgac agaaaaagga gcgatggtta     420
tgacgtcctg ccagttgctg ccgtcgattg cgcctgtcat ccagtacaga acatcctcac     480
ctgactcatt taaaataatg atggcctgtg tcatagagga gaggaacaag tgcacggcca     540
ttcctgacag cgccagcttg acaggcgtca ttccgccgga tgaggcaatc atatacacaa     600
tcgcgccgcc tgctgccgca cccgcaaaag cgaatataac agatgaatag ggcgatgccg     660
gcagaatgac gagagaagca acaacaaaaa gcgatgcacc cgcattcaca ccgaaaattt     720
ggggtgaagc cagaggattt ctggtcatag cctgcatcag cgccctgct acagctaggc     780 tggcgccgac aaaaacgccg attaatgtgc ggggaaggcg aagagtagag atgatgagct     840
gttcctttga accgtccat acaaaaagat atttcaatga atctatgatg ctgatgtctg     900
aggctcctac tgaaagattc agcccaagcc caaatataaa aataatcagt gcaatgataa     960
acatcatcag tcttgatgat gagcgccgtt tggctgaatg atacaacagt ctcacttcct    1020
```

-continued

```
tactgcgtct ggttgcaaaa acgaagaagc aaggattccc ctcgcttctc atttgtccta    1080
tttattatac acttttttaa gcacatcttt ggcgcttgtt tcactagact tgatgcctct    1140
gaatcttgtc caagtgtcac ggtccgcatc atagacttgt ccattttcca ccgctttgag    1200 attttttccag agcgggttcg ttttccactc atctacaatg ttttgcctt cgttggctga    1260 gatgaacaaa atatcaggat cgattttgct caattgctca aggctgacct cttgataggc    1320
gttatctgac ttcacagcgt gtgtaaagcc tagcatttta aagatttctc cgtcatagga    1380
tgatgatgta tgaagctgga aggaatccgc tcttgcaacg ccgagaacga tgttgcggtt    1440
ttcatctttc ggaagttcgg cttttagatc gttgatgact ttttttgtgct cggcaagctt    1500 ttcttttcct tcatcttctt tatttaatgc tttagcaatg gtcgtaaagc tgtcgatcgt    1560
ttcgtcatat gtcgcttcac ggcttttttaa ttcaatcgtc ggggcgattt ttttcagctg    1620
tttataaatg ttttttatggc gctcagcgtc agcgatgatt aaatcaggct tcaaggaact    1680
gatgacctca agattgggtt cgctgcgtgt gcctacagat gtgtaatcaa tggagctgcc    1740
gacaagcttt ttaatcatat ctttttttgtt gtcatctgcg atgcccaccg gcgtaatgcc    1800
gagattgtga acggcatcca agaatgaaag ctcaagcaca accacccgct taggtgtgcc    1860
gcttactgtc gttttttcctt cttcgtcatg gatcactctg gaatccttag actcgctttt    1920
gccgcttccg ttgttattct ggcttgatga acagccggat acaatgaggc aggcgagcaa    1980
taaaacactc atgatggcaa tcaacttgtt agaataggtg cgcatgtcat tcttcctttt    2040
ttcagattta gtaatgagaa tcattatcac atgtaacact ataatagcat ggcttatcat    2100
gtcaatattt ttttagtaaa gaaagctgcg ttttttactgc tttctcatga aagcatcatc    2160
agacacaaat aagtggtatg cagcgttacc gtgtcttcga gacaaaaacg catgggcgtt    2220
ggctttagag gtttcgaaca tatcagcagt gacataagga aggagagtgc tgagataacc    2280
ggacaatttc ttttctattt catctgttag tgcaaattca atgtcgccga tattcatgat    2340
aatcgagaaa acaaagtcga tatcgatatg aaaatgttcc tcggcaaaaa ccgcaagctc    2400
gtgaattcct ggtgaacatc cggcacgctt atggaaaatc tgtttgacta aatcactcac    2460
aatccaagca ttgtattgct gttctggtga aaagtattgc attagacata cctcctgctc    2520
gtacggataa aggcagcgtt tcatggtcgt gtgctccgtg cagcggcttc tccttaatttt    2580 tgattttttct gaaataggt cccgttccta tcactttacc atggacggaa acaaatagc     2640 tactaccatt cctcctgttt ttctcttcaa tgttctggaa tctgtttcag gtacagacga    2700
tcgggtatga agaaatata gaaaacatga aggaggaata tcgacatgaa accagttgta    2760
aaagagtata caaatgacga acagctcatg aaagatgtag aggaattgca gaaaatgggt    2820
gttgcgaaag aggatgtata cgtcttagct cacgacgatg acagaacgga acgcctggct    2880
gacaacacga acgccaacac gatcggagcc aaagaaacag gtttcaagca cgcggtggga    2940
aatatcttca ataaaaaagg agacgagctc cgcaataaaa ttcacgaaat cggttttttct    3000 gaagatgaag ccgctcaatt tgaaaaacgc ttagatgaag gaaaagtgct tctctttgtg    3060
acagataacg aaaaagtgaa agcttgggca taaagcaagg aaaaaaccaa aaggccaatg    3120
tcggcctttt ggttttttttg cggtctttgc ggtgggattt tgcagaatgc cgcaatagga    3180
tagcggaaca ttttcggttc tgaatgtccc tcaatttgct attatatttt tgtgataaat    3240
tggaataaaa tctcacaaaa tagaaaatgg gggtacatag tggatgaaaa aagtgatgtt    3300
agctacggct ttgttttttag gattgactcc agctggcgcg aacgcagctg atttaggcca    3360
ccagacgttg ggatccaatg atggctgggg cgcgtactcg accggcacga caggcggatc    3420
```

```
aaaagcatcc tcctcaaatg tgtataccgt cagcaacaga aaccagcttg tctcggcatt    3480
agggaaggaa acgaacacaa cgccaaaaat catttatatc aagggaacga ttgacatgaa    3540
cgtggatgac aatctgaagc cgcttggcct aaatgactat aaagatccgg agtatgattt    3600
ggacaaatat ttgaaagcct atgatcctag cacatggggc aaaaagagc cgtcgggaac     3660 acaagaagaa gcgagagcac gctctcagaa aaaccaaaaa gcacgggtca tggtggatat    3720
ccctgcaaac acgacgatcg tcggttcagg gactaacgct aaagtcgtgg gaggaaactt    3780
ccaaatcaag agtgataacg tcattattcg caacattgaa ttccaggatg cctatgacta    3840
ttttccgcaa tggttgtaaa acgacggcca gtgaattctg atcaaatggt tcagtgagag    3900
cgaagcgaac acttgatttt ttaattttct atcttttata ggtcattaga gtatacttat    3960
ttgtcctata aactatttag cagcataata gatttattga ataggtcatt taagttgagc    4020
atattagagg aggaaaatct tggagaaata tttgaagaac ccgaggatct agatcaggta    4080
ccgcaacgtt cgcagatgct gctgaagaga ttattaaaaa gctgaaagca aaaggctatc    4140
aattggtaac tgtatctcag cttgaagaag tgaagaagca gagaggctat tgaataaatg    4200
agtagaaagc gccatatcgg cgcttttctt tggaagaaa atatagggaa aatggtactt     4260
gttaaaaatt cggaatattt atacaatatc atatgtatca cattgaaagg aggggcctgc    4320
tgtccagact gtccgctgtg taaaaaaaag gaataaaggg gggttgacat tattttactg    4380
atatgtataa tataatttgt ataagaaaat ggaggggccc tcgaaacgta agatgaaacc    4440
ttagataaaa gtgctttttt tgttgcaatt gaagaattat taatgttaag cttaattaaa    4500
gataatatct ttgaattgta acgcccctca aaagtaagaa ctacaaaaaa agaatacgtt    4560
atatagaaat atgtttgaac cttcttcaga ttacaaatat attcggacgg actctacctc    4620
aaatgcttat ctaactatag aatgacatac aagcacaacc ttgaaaattt gaaaatataa    4680
ctaccaatga acttgttcat gtgaattatc gctgtattta attttctcaa ttcaatatat    4740
aatatgccaa tacattgtta caagtagaaa ttaagacacc cttgatagcc ttactatacc    4800
taacatgatg tagtattaaa tgaatatgta aatatattta tgataagaag cgacttattt    4860
ataatcatta catatttttc tattggaatg attaagattc caatagaata gtgtataaat    4920
tatttatctt gaaaggaggg atgcctaaaa acgaagaaca ttaaaaacat atatttgcac    4980
cgtctaatgg atttatgaaa aatcatttta tcagtttgaa aattatgtat tatggagctc    5040
tataaaaatg aggagggaac cgaatgaaac aacaaaaacg gctttacgcc cgattgctga    5100
cgctgttatt tgcgctcatc ttcttgctgc ctcattctgc agcagcagcg atcgcaggcg    5160
tggttcaaag cgtgaatgtc tcccaagctg gttatagttc aaacgatttt aagacggcta    5220
cggtgactgc gtcggataaa ctaagcgata ctagctacca gatattgcaa ggcactaccg    5280
ttatcgcaac cggtacgatg aaggatgaag gatatgtatg gggcaaatat gtgtactcga    5340
tcgatttctc ctccgttaca gctacgggca ccaactttac gatccgtagc aacgagtttt    5400
catcttacac gttccctatc caaaccaata tgtggaatga atataaggat gaaatgaccg    5460
cgttctaccg tttgctccgg actacggata ccttttgcggc ctatcctgca gggtacagca    5520
atattgcgcc ttcgaataaa atattacatc cggattcttt ccttgatgat gcttttttcgc    5580 cggaccgaac gacgcattat gacctgactg gcggttggtt cgatgcagga gactacggta    5640
agtatggcgg caatcagtgg gtacagggaa atatcgccat ctcttatctg cggcatgcct    5700
cttcggcggc ggtcaatttc gataaggata ccaacggcat tccggatctg gtggatgaag    5760
```

```
cgatctttgg tagtcagtac ttggtgaagt ttgccaatca gcttggcggg gccattcata    5820
atattttgag gaaaggcggc tttgtgcttc cgcataaagt gacagacaat gttccgggta    5880
acacagacga ccgagcgctc gaagctgtcg aagcggtggg aggctccggg aaatcctctg    5940
gctcgctggc ggcaacggcg cgagcgattc gcactgccat cgcgggcggt aaagtggcag    6000
cgaataaagt cgcccagctg cagacacttg cgaatgagtt tcaggctgcc gcaatcatct    6060
tctataatta cacattgact catcaaagtg gaaaccatgg ctcctatgga caatgaaca    6120
atggagggat tgcaaatcct ctcttatggg cggaagtaca gttgtatctg ttaacagggg    6180
acgctgcata caagacgcaa gctcagacac gcattaatgc aataaatgaa gcctatgttt    6240
cgtccacgaa ttattgggat atgcatccga ttgcgctggc cgaatttat tcctgaagca    6300
ccaagcatat tatttcatca cgctgatgga tgaaacgcca tacggtgtat tgaaccaatt    6360
cggcaatttt ggtgtgaatg agccgcatgc atcgtatatg gccgatttgc tccgatatta    6420
tgaattgttt aacgatccgg tagcgcttcg agcggcgaag aaggcgctgt actggattgt    6480
cggcaacaat ccatggaata tcagctgggt atccggtgtc ggctccaact tcaccgattt    6540
cctgcacact cgtctggatg aagaagcata cagccagacg aatacaggcg ttgttctgcc    6600
tggagccatg gttagcggac cgaatatcaa agatccgaat aacaaattga gctctagccc    6660
ttggtatgag gataaaccta tttgggcaga tgacaccaat caatggagat acaacgaata    6720
tagtgtcagt atacagacgg gattattcta caccatcatg ggcttgtcgg cccttggcgg    6780
aaatgcatcc actggtggcg cggagcccgt taagctgccg atcacttggc ctatcattgg    6840
ggattatgtg actggggatg tgacggtatt cgcacagccg gaaggcagct tgagcaatgt    6900
gtcagcgaac ggaatcgtct tgagcccctc cgacggtgtc tatacgacga cagtaagcac    6960
aagcgctgat gcaccatata ccgaaagaaa agtacagatc aaagggacgg acgacagcgg    7020
attcaccact tatagcaata cacatttcac ggtggcgcct gcacttccgg atccatctca    7080
tcctttactt ttcgatgact ttaaccagaa aggaatctgg ggtagccaaa agctggattg    7140
ggtgaattgg tataaccaaa acggaggtac agcatcctac acgcggacga cagtggatac    7200
aagaacagtt gggaaatttg cacataccc tgcagccact acatccaaag ccaaattcca    7260
gccgtggaaa tacaacgcaa atcttaacgg atatcgctat cttaatttca ccatgaagaa    7320
tccgggttat cccaatacca aaattcggat agcagcgaat gacggcacca aatcagttaa    7380
ccttacgagc ggcgaggttg cgatctcgag cacgtggaca acgtatcaat atgatttgaa    7440
tctgcatccg acgctgaaca agagcaacgt tctgattgag gtatggctca gcaacccaac    7500
tgcgggggca tatgggaaa ttctcattga cgaaatctcg gctgtgaata cgaacagcgg    7560
aacggcgcca accttatccg ccacaggtgt gaacgcctcg atcggtaatc agtcgacggt    7620
atttacttat acagcgacct acaccgatgc taataatcaa gcgccgtttg atgtccaggt    7680
cgtcattgac ggcgtcatcc gttcgatgac ggcggcggat cctactgaca ctacttattc    7740
cgatgggaga gtgtatacgt acgctactac cttgccggtg gggacgcata agttttactt    7800
ccggacgaca gatacaacca cgaacttcgt cagcacttcc gtgcaaaccg gaccaaccgt    7860
cattcggaat atacacatgc tgtaaaagac aatgcggatg cgagcggagg gaagtatcgc    7920
ttgttcaatg gtcggcaggc caacgattat attgaatatg cggtgaatgt ccctaaggct    7980
ggaacatatc aagtatctgc cagagccatg agattaagcg acaatgggat ctaccagctg    8040
cagattaacg gcagcaatca aggtactccg ttcgatactt accagtcatc ggggaagtat    8100
cttgactatg ctcttggaaa tgtgaccata actagcccgg gaacgcagtt atttcgattc    8160
```

```
aaagtaacgg gcaaaaatgc aagctcactc ggatataagc tgccgcttga tttcattcag   8220
cttgttccag ttccgtaaac gcgttaatca ataaaaaaac gctgtgcggt taagggcac    8280 agcgttttt tgtgtatcgg caatagttac ccttattatc aagataagaa agaaaaggat    8340
ttttcgctac gctcaaatcc tttaaaaaaa cacaaaagac cacatttttt aatgtggtct   8400
ttattcttca actaaagcac ccattagttc aacaaacgaa aattggataa agtgggatat   8460
ttttaaaata tatatttatg ttacagtaat attgactttt aaaaaaggat tgattctaat   8520
gaagaaagca gacaagtaag cctcctaaat tcactttaga taaaaattta ggaggcatat   8580
caaatgaact ttaataaaat tgatttagac aattggaaga gaaagagat atttaatcat    8640 tatttgaacc aacaaacgac ttttagtata accacagaaa ttgatattag tgttttatac   8700
cgaaacataa aacaagaagg atataaattt taccctgcat ttattttctt agtgacaagg   8760
gtgataaact caaatacagc ttttagaact ggttacaata gcgacggaga gttaggttat   8820
tgggataagt tagagccact ttatacaatt tttgatggtg tatctaaaac attctctggt   8880
atttggactc ctgtaaagaa tgacttcaaa gagttttatg atttatacct ttctgatgta   8940
gagaaatata atggttcggg gaaattgttt cccaaaacac ctatacctga aaatgctttt   9000
tctctttcta ttattccatg gacttcattt actgggttta acttaaatat caataataat   9060
agtaattacc ttctacccat tattacagca ggaaaattca ttaataaagg taattcaata   9120
tatttaccgc tatctttaca ggtacatcat tctgtttgtg atggttatca tgcaggattg   9180
tttatgaact ctattcagga attgtcagat aggcctaatg actggctttt ataatatgag   9240
ataatgccga ctgtactttt tacagtcggt tttctaacga tacattaata ggtacgaaaa   9300
agcaactttt tttgcgctta aaaccagtca taccaataac ttaagggtaa ctagcctcgc   9360
cggaaagagc gaaaatgcct cacatttgtg ccacctaaaa aggagcgatt tacatatgag   9420
ttatgcagtt tgtagaatgc aaaaagtgaa atcagctgga ctaaaagggg ccgcagagta   9480
gaatggaaaa ggggatcgga aaacaagtat ataggaggag acctatttat ggcttcagaa   9540
aaagacgcag gaaaacagtc agcagtaaag cttgttccat tgcttattac tgtcgctgtg   9600
ggactaatca tctggtttat tcccgctccg tccggacttg aacctaaagc ttggcatttg   9660
tttgcgattt ttgtcgcaac aattatcggc tttatctcca gcccttgcc aatgggtgca    9720 attgcaattt ttgcattggc ggttactgca ctaactggaa cactatcaat tgaggataca   9780
ttaagcggat tcgggaataa gaccatttgg cttatcgtta tcgcattctt tatttcccgg   9840
ggatttatca aaaccggtct cggtgcgaga atttcgtatg tattcgttca gaaattcgga   9900
aaaaaacccc ttggactttc ttattcactg ctattcagtg atttaatact ttcacctgct   9960
attccaagta atacgcgcg tgcaggaggc attatatttc ctattatcag atcattatcc    10020
gaaacattcg gatcaagccc ggcaaatgga acagagagaa aaatcggtgc attcttatta   10080
aaaaccggtt ttcaggggaa tctgatcaca tctgctatgt tcctgacagc gatggcggcg   10140
aacccgctga ttgccaagct ggcccatgat gtcgcagggg tggacttaac atggacaagc   10200
tgggcaattg ccgcgattgt accgggactt gtaagcttaa tcatcacgcc gcttgtgatt   10260
tacaaactgt atccgccgga aatcaaagaa acaccggatg cggcgaaaat cgcaacgaaa   10320
aaactgaaag aaatgggacc gttcaaaaaa tcggagcttt ccatggttat cgtgtttctt   10380
ttggtgcttg tgctgtggat ttttggcggc agcttcaaca tcgacgctac cacaaccgca   10440
ttgatcggtt tggccgttct cttattatca caagttctga cttgggatga tatcaagaaa   10500
```

| | | |
|---|---|---|
| gaacagggcg cttgggatac gctcacttgg tttgcggcgc ttgtcatgct cgccaacttc | 10560 | |
| ttgaatgaat taggcatggt gtcttggttc agtaatgcca tgaaatcatc cgtatcaggg | 10620 | |
| ttctcttgga ttgtggcatt catcatttta attgttgtgt attattactc tcactatttc | 10680 | |
| tttgcaagtg cgacagccca catcagtgcg atgtattcag cattttttggc tgtcgtcgtg | 10740 | |
| gcagcgggcg caccgccgct tttagcagcg ctgagcctcg cgttcatcag caacctgttc | 10800 | |
| gggtcaacga ctcactacgg ttctggagcg gctccggtct tcttcggagc aggctacatc | 10860 | |
| ccgcaaggca aatggtggtc catcggattt atcctgtcga ttgttcatat catcgtatgg | 10920 | |
| cttgtgatcg gcggattatg gtggaaagta ctaggaatat ggtagaaaga aaaaggcaga | 10980 | |
| cgcggtctgc ctttttttat tttcactcct tcgtaagaaa atggattttg aaaaatgaga | 11040 | |
| aaattccctg tgaaaaatgg tatgatctag gtagaaagga cggctggtgc tgtggtgaaa | 11100 | |
| aagcggttcc attttcccct gcaaacaaaa ataatggggc tgattgcggc tctgctggtc | 11160 | |
| tttgtcattg gtgtgctgac cattacgtta gccgttcagc atacacaggg agaacggaga | 11220 | |
| caggcagagc agctggcggt tcaaacggcg agaaccattt cctatatgcc gccggttaaa | 11280 | |
| gagctcattg agagaaaaga cggacatgcg gctcagacgc aagaggtcat tgaacaaatg | 11340 | |
| aaagaacaga ctggtgcgtt tgccatttat gttttgaacg aaaaaggaga cattcgcagc | 11400 | |
| gcctctggaa aaagcggatt aaagaaactg gagcgcagca gagaaatttt gtttggcggt | 11460 | |
| tcgcatgttt ctgaaacaaa agcggatgga cgaagagtga tcagagggag cgcgccgatt | 11520 | |
| ataaaagaac agaagggata cagccaagtg atcggcagcg tgtctgttga ttttctgcaa | 11580 | |
| acggagacag agcaaagcat caaaaagcat ttgagaaatt tgagtgtgat tgctgtgctt | 11640 | |
| gtactgctgc tcggatttat tggcgccgcc gtgctggcga aaagcatcag aaaggatacg | 11700 | |
| ctcgggcttg aaccgcatga gatcgcggct ctatatcgtg agaggaacgc aatgcttttc | 11760 | |
| gcgattcgag aagggattat tgccaccaat cgtgaaggcg tcgtcaccat gatgaacgta | 11820 | |
| tcggcggccg agatgctgaa gctgcccgag cctgtgatcc atcttcctat agatgacgtc | 11880 | |
| aaatgctgcc gaaccaggaa gtaagcgtca acgatcaagt gtttattatc aatacgaaag | 11940 | |
| tgatgaatca aggcgggcag gcgtatggga ttgtcgtcag cttcagggag aaaacagagc | 12000 | |
| tgaagaagct gatcgacaca ttgacagagg ttcgcaaata ttcagaggat ctcagggcgc | 12060 | |
| agactcatga atttttcaaat aagctttatg cgattttagg gctgcgtcga | 12110 | |

<210> SEQ ID NO 2
<211> LENGTH: 1050
<212> TYPE: PRT
<213> ORGANISM: Paenibacillus sp-62047

<400> SEQUENCE: 2

```
Ile Ala Gly Val Val Gln Ser Val Asn Val Ser Gln Ala Gly Tyr Ser
1               5                   10                  15

Ser Asn Asp Phe Lys Thr Ala Thr Val Thr Ala Ser Asp Lys Leu Ser
            20                  25                  30

Asp Thr Ser Tyr Gln Ile Leu Gln Gly Thr Thr Val Ile Ala Thr Gly
        35                  40                  45

Thr Met Lys Asp Glu Gly Tyr Val Trp Gly Lys Tyr Val Tyr Ser Ile
    50                  55                  60

Asp Phe Ser Ser Val Thr Ala Thr Gly Thr Asn Phe Thr Ile Arg Ser
65                  70                  75                  80

Asn Gly Val Ser Ser Tyr Thr Phe Pro Ile Gln Thr Asn Met Trp Asn
                85                  90                  95
```

```
Glu Tyr Lys Asp Glu Met Thr Ala Phe Tyr Arg Leu Leu Arg Thr Thr
            100                 105                 110

Asp Thr Phe Ala Ala Tyr Pro Ala Gly Tyr Ser Asn Ile Ala Pro Ser
            115                 120                 125

Asn Lys Ile Leu His Pro Asp Ser Phe Leu Asp Ala Phe Ser Pro
            130                 135                 140

Asp Arg Thr Thr His Tyr Asp Leu Thr Gly Gly Trp Phe Asp Ala Gly
145                 150                 155                 160

Asp Tyr Gly Lys Tyr Gly Gly Asn Gln Trp Val Gln Gly Asn Ile Ala
                165                 170                 175

Ile Ser Tyr Leu Arg His Ala Ser Ser Ala Ala Val Asn Phe Asp Lys
            180                 185                 190

Asp Thr Asn Gly Ile Pro Asp Leu Val Asp Glu Ala Ile Phe Gly Ser
            195                 200                 205

Gln Tyr Leu Val Lys Phe Ala Asn Gln Leu Gly Gly Ala Ile His Asn
            210                 215                 220

Ile Leu Arg Lys Gly Gly Phe Val Leu Pro His Lys Val Thr Asp Asn
225                 230                 235                 240

Val Pro Gly Asn Thr Asp Asp Arg Ala Leu Glu Ala Val Glu Ala Val
                245                 250                 255

Gly Gly Ser Gly Lys Ser Ser Gly Ser Leu Ala Ala Thr Ala Arg Ala
            260                 265                 270

Ile Arg Thr Ala Ile Ala Gly Gly Lys Val Ala Ala Asn Lys Val Ala
            275                 280                 285

Gln Leu Gln Thr Leu Ala Asn Glu Phe Gln Ala Ala Ile Ile Phe
            290                 295                 300

Tyr Asn Tyr Thr Leu Thr His Gln Ser Gly Asn His Gly Ser Tyr Gly
305                 310                 315                 320

Thr Met Asn Asn Gly Gly Ile Ala Asn Pro Leu Leu Trp Ala Glu Val
                325                 330                 335

Gln Leu Tyr Leu Leu Thr Gly Asp Ala Ala Tyr Lys Thr Gln Ala Gln
            340                 345                 350

Thr Arg Ile Asn Ala Ile Asn Glu Ala Tyr Val Ser Ser Thr Asn Tyr
            355                 360                 365

Trp Asp Met His Pro Ile Ala Leu Ala Glu Phe Tyr Pro Val Ala Asp
            370                 375                 380

Ser Ala Ile Lys Thr Lys Ile Gln Ser Ile Leu Lys His Gln Ala Tyr
385                 390                 395                 400

Tyr Phe Ile Thr Leu Met Asp Glu Thr Pro Tyr Gly Val Leu Asn Gln
                405                 410                 415

Phe Gly Asn Phe Gly Val Asn Glu Pro His Ala Ser Tyr Met Ala Asp
            420                 425                 430

Leu Leu Arg Tyr Tyr Glu Leu Phe Asn Asp Pro Val Ala Leu Arg Ala
            435                 440                 445

Ala Lys Lys Ala Leu Tyr Trp Ile Val Gly Asn Asn Pro Trp Asn Ile
            450                 455                 460

Ser Trp Val Ser Gly Val Gly Ser Asn Phe Thr Asp Phe Leu His Thr
465                 470                 475                 480

Arg Leu Asp Glu Glu Ala Tyr Ser Gln Thr Asn Thr Gly Val Val Leu
                485                 490                 495

Pro Gly Ala Met Val Ser Gly Pro Asn Ile Lys Asp Pro Asn Asn Lys
            500                 505                 510
```

-continued

Leu Ser Ser Ser Pro Trp Tyr Glu Asp Lys Pro Ile Trp Ala Asp Asp
                515                 520                 525

Thr Asn Gln Trp Arg Tyr Asn Glu Tyr Ser Val Ser Ile Gln Thr Gly
530                 535                 540

Leu Phe Tyr Thr Ile Met Gly Leu Ser Ala Leu Gly Gly Asn Ala Ser
545                 550                 555                 560

Thr Gly Gly Ala Glu Pro Val Lys Leu Pro Ile Thr Trp Pro Ile Ile
                565                 570                 575

Gly Asp Tyr Val Thr Gly Asp Val Thr Val Phe Ala Gln Pro Glu Gly
                580                 585                 590

Ser Leu Ser Asn Val Ser Ala Asn Gly Ile Val Leu Ser Pro Ser Asp
                595                 600                 605

Gly Val Tyr Thr Thr Thr Val Ser Thr Ser Ala Asp Ala Pro Tyr Thr
                610                 615                 620

Glu Arg Lys Val Gln Ile Lys Gly Thr Asp Asp Ser Gly Phe Thr Thr
625                 630                 635                 640

Tyr Ser Asn Thr His Phe Thr Val Ala Pro Ala Leu Pro Asp Pro Ser
                645                 650                 655

His Pro Leu Leu Phe Asp Asp Phe Asn Gln Lys Gly Ile Trp Gly Ser
                660                 665                 670

Gln Lys Leu Asp Trp Val Asn Trp Tyr Asn Gln Asn Gly Gly Thr Ala
                675                 680                 685

Ser Tyr Thr Arg Thr Thr Val Asp Thr Arg Thr Val Gly Lys Phe Ala
                690                 695                 700

His Thr Pro Ala Ala Thr Thr Ser Lys Ala Lys Phe Gln Pro Trp Lys
705                 710                 715                 720

Tyr Asn Ala Asn Leu Asn Gly Tyr Arg Tyr Leu Asn Phe Thr Met Lys
                725                 730                 735

Asn Pro Gly Tyr Pro Asn Thr Lys Ile Arg Ile Ala Ala Asn Asp Gly
                740                 745                 750

Thr Lys Ser Val Asn Leu Thr Ser Gly Glu Val Ala Ile Ser Ser Thr
                755                 760                 765

Trp Thr Thr Tyr Gln Tyr Asp Leu Asn Leu His Pro Thr Leu Asn Lys
                770                 775                 780

Ser Asn Val Leu Ile Glu Val Trp Leu Ser Asn Pro Thr Ala Gly Ala
785                 790                 795                 800

Tyr Gly Glu Ile Leu Ile Asp Glu Ile Ser Ala Val Asn Thr Asn Ser
                805                 810                 815

Gly Thr Ala Pro Thr Leu Ser Ala Thr Gly Val Asn Ala Ser Ile Gly
                820                 825                 830

Asn Gln Ser Thr Val Phe Thr Tyr Thr Ala Thr Tyr Thr Asp Ala Asn
                835                 840                 845

Asn Gln Ala Pro Phe Asp Val Gln Val Val Ile Asp Gly Val Ile Arg
                850                 855                 860

Ser Met Thr Ala Ala Asp Pro Thr Asp Thr Thr Tyr Ser Asp Gly Arg
865                 870                 875                 880

Val Tyr Thr Tyr Ala Thr Thr Leu Pro Val Gly Thr His Lys Phe Tyr
                885                 890                 895

Phe Arg Thr Thr Asp Thr Thr Thr Asn Phe Val Ser Thr Ser Val Gln
                900                 905                 910

Thr Gly Pro Thr Val Ile Arg Asn Lys Leu Glu Ala Glu Val Leu Ser
                915                 920                 925

-continued

```
Ile Asn Leu Thr Asn Tyr Thr His Ala Val Lys Asp Asn Ala Asp Ala
        930             935             940

Ser Gly Gly Lys Tyr Arg Leu Phe Asn Gly Arg Gln Ala Asn Asp Tyr
945             950             955             960

Ile Glu Tyr Ala Val Asn Val Pro Lys Ala Gly Thr Tyr Gln Val Ser
            965             970             975

Ala Arg Ala Met Arg Leu Ser Asp Asn Gly Ile Tyr Gln Leu Gln Ile
        980             985             990

Asn Gly Ser Asn Gln Gly Thr Pro  Phe Asp Thr Tyr Gln  Ser Ser Gly
        995             1000            1005

Lys Tyr  Leu Asp Tyr Ala Leu  Gly Asn Val Thr Ile  Thr Ser Pro
    1010             1015            1020

Gly Thr  Gln Leu Phe Arg Phe  Lys Val Thr Gly Lys  Asn Ala Ser
    1025             1030            1035

Ser Leu  Gly Tyr Lys Leu Pro  Leu Asp Phe Ile Gln
    1040             1045            1050

<210> SEQ ID NO 3
<211> LENGTH: 87
<212> TYPE: DNA
<213> ORGANISM: Bacillus licheniformis

<400> SEQUENCE: 3
atgaaacaac aaaaacggct ttacgcccga ttgctgacgc tgttatttgc gctcatcttc      60
ttgctgcctc attctgcagc agcagcg                                          87

<210> SEQ ID NO 4
<211> LENGTH: 29
<212> TYPE: PRT
<213> ORGANISM: Bacillus licheniformis

<400> SEQUENCE: 4

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala
            20                  25
```

DETERGENT COMPOSITIONS COMPRISING GH9 ENDOGLUCANASE VARIANTS II

CROSS-REFERENCE TO RELATED APPLICATIONS

The present application is a national stage entry according to 35 U.S.C. § 371 of PCT application No.: PCT/EP2018/0171105 filed on Aug. 3, 2018; which claims priority to German Patent Application Serial No.: 10 2017 214 809,8, which was filed on Aug. 24, 2017; which is incorporated herein by reference in its entirety and for all purposes.

REFERENCE TO A SEQUENCE LISTING

This application contains a Sequence Listing in computer readable form, which is incorporated herein by reference.

JOINT RESEARCH AGREEMENT

The presently claimed invention was made by or on behalf of the below listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are NOVOZYMES AS and HENKEL AG and Co KGaA.

TECHNICAL FIELD

Detergent compositions comprising novel GH9 endoglucanase variants may exhibit alterations relative to the parent GH9 endoglucanase in one or more properties including: detergent stability (e.g. improved stability in a detergent composition,) and/or storage stability (e.g. improved storage stability in a detergent composition). Detergent compositions may include novel GH9 endoglucanase variants having activity on xanthan gum pre-treated with xanthan lyase. Methods for producing and using the detergent compositions are also disclosed. Variants as described herein are particularly suitable for use in cleaning processes and detergent compositions, such as laundry compositions and dish wash compositions, including hand wash and automatic dish wash compositions.

BACKGROUND

Xanthan gum is a polysaccharide derived from the bacterial coat of *Xanthomonas campestris*. It is produced by the fermentation of glucose, sucrose, or lactose by the *Xanthomonas campestris* bacterium. After a fermentation period, the polysaccharide is precipitated from a growth medium with isopropyl alcohol, dried, and ground into a fine powder. Later, it is added to a liquid medium to form the gum. Xanthan gum is a natural polysaccharide consisting of different sugars which are connected by several different bonds, such as β-D-mannosyl-β-D-1,4-glucuronosyl bonds and β-D-glucosyl-β-D-1,4-glucosyl bonds. Xanthan gum is at least partly soluble in water and forms highly viscous solutions or gels. Complete enzymatic degradation of xanthan gum requires several enzymatic activities including xanthan lyase activity and endo-β-1,4-glucanase activity. Xanthan lyases are enzymes that cleave the β-D-mannosyl-β-D-1,4-glucuronosyl bond of xanthan and have been described in the literature. Xanthan lyases are known in the art, e.g. two xanthan lyases have been isolated from *Paenibacillus alginolyticus* XL-1 (e.g. Ruijssenaars et al. (1999) 'A pyruvated mannose-specific xanthan lyase involved in xanthan degradation by *Paenibacillus alginolyticus* XL-1', Appl. Environ. Microbiol. 65(6): 2446-2452, and Ruijssenaars et al. (2000), 'A novel gene encoding xanthan lyase of *Paenibacillus alginolyticus* strain XL-1', Appl. Environ. Microbiol. 66(9): 3945-3950). Glycoside hydrolases are enzymes that catalyse the hydrolysis of the glycosyl bond to release smaller sugars. There are over 100 classes of glycoside hydrolases which have been classified, see Henrissat et al. (1991) 'A classification of glycosyl hydrolases based on amino-acid sequence similarities', J. Biochem. 280: 309-316 and the Uniprot website at www.cazy.org. The glycoside hydrolase family 9 (GH9) consists of over 70 different enzymes that are mostly endo-glucanases (EC 3.2.1.4), cellobiohydrolases (EC 3.2.1.91), β-glucosidases (EC 3.2.1.21) and exo-β-glucosaminidase (EC 3.2.1.165). In recent years xanthan gum has been used as an ingredient in many consumer products including foods (e.g. as thickening agent in salad dressings and dairy products) and cosmetics (e.g. as stabilizer and thickener in toothpaste and make-up, creams and lotions to prevent ingredients from separating and to provide the right texture of the product). Further xanthan gum has found use in the oil industry as an additive to regulate the viscosity of drilling fluids etc. The widespread use of xanthan gum has led to a desire to degrade solutions, gels or mixtures containing xanthan gum thereby allowing easier removal of the byproducts. Endoglucanases and xanthan lyases for the degradation of xanthan gum and the use of such enzymes for cleaning purposes, such as the removal of xanthan gum containing stains, and in the drilling and oil industries are known in the art, e.g. WO2013167581A1.

The known xanthan endoglucanase having SEQ ID NO: 2 was found to be sensitive to storage in detergent. To improve the applicability and/or cost and/or the performance of such enzymes there is an ongoing search for variants with altered properties, such as increased stability, e.g. improved stability in a detergent composition. However, mutagenesis of large enzymes followed by purification and functional analysis of mutant libraries can be very expensive and laborious.

SUMMARY

Since the known xanthan endoglucanase having SEQ ID NO: 2 is a large enzyme (>1000 residues), it is difficult and expensive to randomly target its properties for improvement of, e.g., stability in a detergent composition.

In some aspects a non-limiting embodiment identifies regions in the protein sequence/structure of the known xanthan endoglucanase having SEQ ID NO: 2 that are relevant for e.g. storage stability, and therefore provides an important guidance on where to mutate an endoglucanase in order to stabilize the molecule in a detergent.

In some aspects, a non-limiting embodiment relates to a detergent composition comprising an endoglucanase variant, comprising an alteration (e.g., a substitution, deletion or insertion) at one or more positions in a region selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2.

In some aspects, a non-limiting embodiment relates to a detergent composition comprising an endoglucanase variant, comprising an alteration (e.g., a substitution, deletion or insertion) at one or more positions in a region selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2, wherein said variant has at least 60% and less than 100% sequence identity to SEQ ID NO: 2; said endoglucanase variant has activity on xanthan gum pre-treated with xanthan lyase.

In some aspects, a non-limiting embodiment relates to a detergent composition comprising an endoglucanase variant having at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

In some aspects, a non-limiting embodiment relates to a detergent composition comprising an endoglucanase variant, comprising an alteration (e.g., a substitution, deletion or insertion) at one or more positions in a region selected from the group consisting of:
i) region 10 corresponding to amino acids 1 to 94 of SEQ ID NO: 2, e.g., said alteration at one or more positions selected from the group consisting of positions: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, wherein said positions correspond to amino acid positions of SEQ ID NO: 2 (e.g., using the numbering of SEQ ID NO: 2),
ii) region 11 corresponding to amino acids 106 to 114 of SEQ ID NO: 2, e.g., said alteration at one or more positions selected from the group consisting of positions: 107, 108, 109, 110, 111, 112, 113, 114, wherein said positions correspond to amino acid positions of SEQ ID NO: 2 (e.g., using the numbering of SEQ ID NO: 2),
iii) region 12 corresponding to amino acids 139 to 209 of SEQ ID NO: 2, e.g., said alteration at one or more positions selected from the group consisting of positions: 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, wherein said positions correspond to amino acid positions of SEQ ID NO: 2 (e.g., using the numbering of SEQ ID NO: 2),
iv) region 13 corresponding to amino acids 252 to 266 of SEQ ID NO: 2, e.g., said alteration at one or more positions selected from the group consisting of positions: 252, 253, 254, 255, 256, 257, 258, 259, 260, 261, 262, 263, 264, 265, 266, wherein said positions correspond to amino acid positions of SEQ ID NO: 2 (e.g., using the numbering of SEQ ID NO: 2),
v) region 14 corresponding to amino acids 302 to 338 of SEQ ID NO: 2, e.g., said alteration at one or more positions selected from the group consisting of positions: 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, wherein said positions correspond to amino acid positions of SEQ ID NO: 2 (e.g., using the numbering of SEQ ID NO: 2),
vi) region 15 corresponding to amino acids 362 to 546 of SEQ ID NO: 2, e.g., said alteration at one or more positions selected from the group consisting of positions: 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, wherein said positions correspond to amino acid positions of SEQ ID NO: 2 (e.g., using the numbering of SEQ ID NO: 2),
vii) region 16 corresponding to amino acids 596 to 611 of SEQ ID NO: 2, e.g., said alteration at one or more positions selected from the group consisting of positions: 596, 597, 598, 599, 600, 601, 602, 603, 604, 605, 606, 607, 608, 609, 610, 611, wherein said positions correspond to amino acid positions of SEQ ID NO: 2 (e.g., using the numbering of SEQ ID NO: 2),
viii) region 17 corresponding to amino acids 661 to 805 of SEQ ID NO: 2, e.g., said alteration at one or more positions selected from the group consisting of positions: 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, wherein said positions correspond to amino acid positions of SEQ ID NO: 2 (e.g., using the numbering of SEQ ID NO: 2), ix) region 18 corresponding to amino acids 829 to 838 to 1042 of SEQ ID NO: 2, e.g., said alteration at one or more positions selected from the group consisting of positions: 829, 830, 831, 832, 833, 834, 835, 836, 837, 838, wherein said positions correspond to amino acid positions of SEQ ID NO: 2 (e.g., using the numbering of SEQ ID NO: 2)

x) region 19 corresponding to amino acids 1043 to 1055 of SEQ ID NO: 2, e.g., said alteration at one or more positions selected from the group consisting of positions 1043, 1044, 1045, 1046, 1047, 1048, 1049, 1050, 1051, 1052, 1053, 1054, 1055, wherein said positions correspond to amino acid positions of SEQ ID NO: 2 (e.g., using the numbering of SEQ ID NO: 2).

In some aspects, a non-limiting embodiment relates to a detergent composition comprising an endoglucanase variant, comprising an alteration (e.g., a substitution, deletion or insertion) at one or more positions in:

a) one or more regions selected from the group consisting of:

i) region 10 corresponding to amino acids 1 to 94 of SEQ ID NO: 2, e.g., said alteration at one or more positions selected from the group consisting of positions: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, wherein said positions correspond to amino acid positions of SEQ ID NO: 2 (e.g., using the numbering of SEQ ID NO: 2), ii) region 11 corresponding to amino acids 106 to 114 of SEQ ID NO: 2, e.g., said alteration at one or more positions selected from the group consisting of positions: 107, 108, 109, 110, 111, 112, 113, 114, wherein said positions correspond to amino acid positions of SEQ ID NO: 2 (e.g., using the numbering of SEQ ID NO: 2), iii) region 12 corresponding to amino acids 139 to 209 of SEQ ID NO: 2, e.g., said alteration at one or more positions selected from the group consisting of positions: 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, wherein said positions correspond to amino acid positions of SEQ ID NO: 2 (e.g., using the numbering of SEQ ID NO: 2), iv) region 13 corresponding to amino acids 252 to 266 of SEQ ID NO: 2, e.g., said alteration at one or more positions selected from the group consisting of positions: 252, 253, 254, 255, 256, 257, 258, 259, 260, 261, 262, 263, 264, 265, 266, wherein said positions correspond to amino acid positions of SEQ ID NO: 2 (e.g., using the numbering of SEQ ID NO: 2), v) region 14 corresponding to amino acids 302 to 338 of SEQ ID NO: 2, e.g., said alteration at one or more positions selected from the group consisting of positions: 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, wherein said positions correspond to amino acid positions of SEQ ID NO: 2 (e.g., using the numbering of SEQ ID NO: 2), vi) region 15 corresponding to amino acids 362 to 546 of SEQ ID NO: 2, e.g., said alteration at one or more positions selected from the group consisting of positions: 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, wherein said positions correspond to amino acid positions of SEQ ID NO: 2 (e.g., using the numbering of SEQ ID NO: 2), vii) region 16 corresponding to amino acids 596 to 611 of SEQ ID NO: 2, e.g., said alteration at one or more positions selected from the group consisting of positions: 596, 597, 598, 599, 600, 601, 602, 603, 604, 605, 606, 607, 608, 609, 610, 611, wherein said positions correspond to amino acid positions of SEQ ID NO: 2 (e.g., using the numbering of SEQ ID NO: 2), viii) region 17 corresponding to amino acids 661 to 805 of SEQ ID NO: 2, e.g., said alteration at one or more positions selected from the group consisting of positions: 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, wherein said positions correspond to amino acid positions of SEQ ID NO: 2 (e.g., using the numbering of SEQ ID NO: 2), ix) region 18 corresponding to amino acids 829 to 838 to 1042 of SEQ ID NO: 2, e.g., said alteration at one or more positions selected from the group consisting of positions: 829, 830, 831, 832, 833, 834, 835, 836, 837, 838, wherein said positions correspond to amino acid positions of SEQ ID NO: 2 (e.g., using the numbering of SEQ ID NO: 2)

x) region 19 corresponding to amino acids 1043 to 1055 of SEQ ID NO: 2, e.g., said alteration at one or more positions selected from the group consisting of positions 1043, 1044, 1045, 1046, 1047, 1048, 1049, 1050, 1051, 1052, 1053, 1054, 1055, wherein said positions correspond to amino acid positions of SEQ ID NO: 2 (e.g., using the numbering of SEQ ID NO: 2).

In some aspects, a non-limiting embodiment relates to a detergent composition comprising an endoglucanase variant having an alteration (e.g., a substitution, deletion or insertion) at one or more positions selected from the group consisting of positions: 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2, wherein numbering is according to SEQ ID NO: 2.

In some aspects, a non-limiting embodiment relates to a detergent composition comprising an endoglucanase variant having an alteration (e.g., a substitution, deletion or insertion) at one or more positions selected from the group consisting of: 517A, F20P, F20N, F20G, F20Y, K51Q, K51H, E53P, E53G, Y55M, V56M, Y60F, S63F, T87R, A186P, K192N, I302D, I302H, I302V, I302M, H311N, S313D, I387T, K388R, K390Q, I403Y, E408D, E408S, E408P, E408A, E408G, E408N, P410G, Q416S, Q416D, A448E, A448W, A448S, K451S, G471S, S472Y, D476R, Q489P, K507R, K512P, S515V, S538C, Y579W, S598Q, A599S, I602T, I602D, V603P, S605T, G609E, D676H, A688G, Y690F, T694A, T697G, R698W, T699A, T711V, T711Y, W719R, K754R, V756H, V756Y, S760G, T781M, N786K, T797S, A824D, N833D, Q834E, S835D, and F1048W wherein numbering is according to SEQ ID NO: 2.

In one embodiment, a non-limiting embodiment relates to a detergent composition comprising an endoglucanase variant comprising an alteration (e.g., a substitution, deletion or insertion) at one or more positions selected from the group consisting of alterations in positions: 17, 20, 302, 311, 313, 408, 476, 602, 688, 697, and 719, wherein numbering is according to SEQ ID NO: 2.

In an embodiment, the endoglucanase variant comprised in the detergent compositions comprises an alteration at one or more positions selected from the group consisting of alterations in positions: 517A, F20P, I302D, H311N, S313D, E408D, D476R, I602T, A688G, T697G, and W719R, wherein numbering is according to SEQ ID NO: 2.

In an embodiment, the endoglucanase variant comprised in the detergent compositions further comprises an alteration at one or more positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999, and 1037.

In an embodiment, the endoglucanase variant comprised in the detergent compositions further comprises an alteration (e.g., substitution) at one or more positions selected from the group consisting of: N216D, N216Q, A283D, A346D, A559P, A559N, A564E, Y579W, S636K, S636N, F638N, A651P, A824D, N848D, A869V, R880K, V881T, V881Q, T883R, T887K, T892P, N905D, F906A, A912V, K921R, S928D, Y934G, A937E, K948R, Q956Y, T999R, and A1037E.

In an embodiment, the endoglucanase variant comprised in the detergent compositions comprises one or more of the following set of substitutions:

F20Y + A448S + T781M
E408D + K451S
E408D + A448E
E408D
Y579W + E408D

In an embodiment, the endoglucanase variant comprised in the detergent compositions comprises one or more of the following set of substitutions:

S17A, F20P, N216D, A283D, H311N, E408D, Y579W, I602T, A651P, A688G, T883R, F906A, Y934G, Q956Y

F20P, I302D, S313D, E408D, D476R, Y579W, S636K, T697G, V756Y, V881Q, T887K, F906A, A937E
F20P, S313D, E408D, Y579W, S636K, A688G, T697G, N905D, A937E
F20P, I302D, S313D, E408D, D476R, Y579W, S636K, T697G, W719R, V756Y, V881Q, T887K, F906A, A937E
N216Q, S313D, E408D, D476R, Y579W, I602T, F638N, A651P, T697G, W719R, R880K, T887K, K921R, Y934G
N216D, S313D, E408D, D476R, A564E, Y579W, I602T, F638N, A651P, Y690F, T697G, W719R, V756H, N833D, A869V, R880K, V881T, T887K, K921R, S928D, Y934G, T999R
F20P, I302D, S313D, E408D, D476R, Y579W, S636K, T697G, W719R, V756Y, N848D, A869V, V881Q, T887K, N905D, F906A, Q912V, A937E, T999R, F1048W
F20P, I302D, S313D, E408D, D476R, Q489P, Y579W, S636N, T697G, W719R, V756Y, A824D, N848D, V881Q, T887K, F906A, S928D, A937E
F20P, I302D, S313D, E408D, Q416S, D476R, Q489P, Y579W, I602T, S636K, A651P, T697G, W719R, V756Y, A824D, N833D, N848D, T883R, T887K, F906A, A937E
F20P, A186P, I302D, S313D, E408D, D476R, Q489P, Y579W, A599S, I602T, S636K, A651P, T697G, W719R, V756Y, N848D, T883R, T887K, F906A, A937E
N216D, S313D, E408D, D476R, Y579W, I602T, V603P, F638N, A651P, A688G, T697G, W719R, V756H, R880K, T887K, K921R, S928D, Y934G, K948R
F20P, K51Q, I302D, S313D, E408D, D476R, Q489P, Y579W, I602T, S636K, A651P, T697G, W719R, V756Y, N848D, T883R, T887K, F906A, A937E
F20P, I302D, S313D, A346D, E408D, D476R, Q489P, Y579W, S636N, T697G, W719R, V756Y, A824D, N848D, V881Q, T887K, F906A, A937E, T999R
F20P, I302D, S313D, E408D, D476R, Q489P, Y579W, I602T, S636N, T697G, W719R, V756Y, A824D, N848D, V881Q, T887K, N905D, F906A, A937E, T999R, A1037E, F1048W
F20P, K51Q, I302D, S313D, E408D, D476R, Q489P, Y579W, I602T, S636K, A651P, T697G, W719R, V756Y, A824D, N848D, T883R, T887K, F906A, S928D, A937E, A1037E
N216D, S313D, A346D, E408D, D476R, Q489P, A559W, Y579W, I602T, F638N, A651P, A688G, T697G, W719R, V756H, R880K, T887K, K921R, S928D, Y934G
F20P, I302D, S313D, A346D, E408D, D476R, Q489P, Y579W, I602T, T697G, W719R, V756Y, N848D, V881Q, T887K, F906A, A937E
N216D, S313D, E408D, D476R, Q489P, A559P, Y579W, I602T, F638N, A651P, A688G, T697G, W719R, V756H, Q834E, R880K, T887K, T892P, K921R, S928D, Y934G
F20P, I302D, S313D, E408D, D476R, Q489P, A559N, Y579W, I602T, S636K, A651P, T697G, W719R, V756Y, N848D, T883R, T887K, F906A, S928D, A937E
F20P, I302D, S313D, E408D, D476R, Q489P, Y579W, I602T, S636K, A651P, T697G, W719R, V756Y, N848D, T883R, T887K, F906A, A937E
F20P, I302D, S313D, E408D, Q416S, D476R, Q489P, A559N, Y579W, I602T, S636K, A651P, T697G, W719R, V756Y, N848D, T883R, T887K, F906A, A937E
F20P, I302D, S313D, E408D, D476R, Y579W, I602T, S636N, T697G, W719R, V756Y, A824D, N848D, V881Q, T887K, F906A, S928D, A937E, T999R, F1048W

In a particular aspect, the endoglucanase variant as described herein is one that does not comprise any amino acid alteration at a position outside of regions 10, 11, 12, 13, 14, 15, 16, 17, 18, and 19. In this aspect, the endoglucanase variant thus does not comprise any alteration (e.g., a substitution, deletion or insertion) in a region selected from the group consisting of: region 1 corresponding to amino acids 95 to 105 of SEQ ID NO: 2, region 2 corresponding to amino acids 115 to 138 of SEQ ID NO: 2, region 3 corresponding to amino acids 210 to 251 of SEQ ID NO: 2, region 4 corresponding to amino acids 267 to 301 of SEQ ID NO: 2, region 5 corresponding to amino acids 339 to 361 of SEQ ID NO: 2, region 6 corresponding to amino acids 547 to 595 of SEQ ID NO: 2, region 7 corresponding to amino acids 612 to 660 of SEQ ID NO: 2, region 8 corresponding to amino acids 806 to 828 of SEQ ID NO: 2, and region 9 corresponding to amino acids 839 to 1045 of SEQ ID NO: 2.

In some aspects, a non-limiting embodiment relates to a detergent composition comprising an endoglucanase variant having activity on xanthan gum pre-treated with xanthan lyase; said activity comprises endoglucanase EC 3.2.1.4 activity, said activity is endoglucanase EC 3.2.1.4 activity.

In some aspects, a non-limiting embodiment relates to a detergent composition comprising an endoglucanase variant having an improved stability in a detergent composition compared to a parent endoglucanase (e.g., with SEQ ID NO: 2).

In some aspects, a non-limiting embodiment relates to a detergent composition comprising an endoglucanase variant having a half-life improvement factor (HIF) of >1.0 relative to a parent endoglucanase, e.g. an endoglucanase of SEQ ID NO: 2.

In some aspects, a non-limiting embodiment relates to a detergent composition comprising an isolated GH9 endoglucanase variant having activity on xanthan gum pre-treated with xanthan lyase. In a further aspect, the detergent composition further comprises an isolated polypeptide having xanthan lyase activity.

In some aspects, a non-limiting embodiment relates to a detergent composition comprising one or more detergent components for degrading xanthan gum.

In some aspects, a non-limiting embodiment relates to use of a detergent composition, wherein said use is selected from the group consisting of: use for degrading xanthan gum and use in a cleaning process, such as laundry or hard surface cleaning such as dish wash.

In some aspects, a non-limiting embodiment further relates to the use of a detergent composition for degrading xanthan gum, for washing or cleaning textiles and/or hard surfaces, such as dish wash, wherein the composition has an enzyme detergency benefit.

In some aspects, a non-limiting embodiment also relates to methods of degrading xanthan gum using detergent compositions, wherein xanthan gum is on the surface of a hard surface or textile.

OVERVIEW OF SEQUENCE LISTING

SEQ ID NO: 1 is the DNA sequence of the parent mature endoglucanase from a strain of a *Paenibacillus* sp.

SEQ ID NO: 2 is the amino acid sequence of mature polypeptide encoded by SEQ ID NO: 1.

SEQ ID NO: 3 is the DNA sequence of the alpha-amylase secretion signal from *Bacillus licheniformis*.

SEQ ID NO: 4 is the amino acid sequence of the alpha-amylase secretion signal from *Bacillus licheniformis*.

DEFINITIONS cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cleaning or Detergent Application: the term "cleaning or detergent application" means applying the endoglucanase of the application in any composition for the purpose of cleaning or washing, by hand, machine or automated, a hard surface or a textile.

Cleaning Composition: the term "cleaning composition" refers to compositions that find use in the removal of undesired compounds from items to be cleaned, such as textiles, dishes, and hard surfaces. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to the endoglucanase, the detergent formulation may contain one or more additional enzymes (such as xanthan lyases, proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, anti-oxidants, and solubilizers.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Colour clarification: During washing and wearing loose or broken fibers can accumulate on the surface of the fabrics. One consequence can be that the colours of the fabric appear less bright or less intense because of the surface contaminations. Removal of the loose or broken fibers from the textile will partly restore the original colours and looks of the textile. By the term "colour clarification", as used herein, is meant the partial restoration of the initial colours of textile.

Control sequences: The term "control sequences" means nucleic acid sequences necessary for expression of a polynucleotide encoding a mature polypeptide. Each control sequence may be native (La, from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Corresponding to: The term "corresponding to" as used herein, refers to a way of determining the specific amino acid of a sequence wherein reference is made to a specific amino acid sequence. E.g. for the purposes, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 2, or any other sequence listed herein, has been described elsewhere herein. Alternative alignment methods may be used, and are well-known for the skilled person.

Degrading xanthan gum and xanthan gum degrading activity: The terms "degrading xanthan gum" and "xanthan gum degrading activity" are used interchangeably and are defined as the depolymerization, degradation or breaking down of xanthan gum into smaller components. The degradation of xanthan gum can either be the removal of one or more side chain saccharides, the cutting of the backbone of xanthan gum into smaller components or the removal of one or more side chain saccharides and the cutting of the backbone of xanthan gum into smaller components. A non-limiting assay for measuring degradation of xanthan gum is the reducing sugar assay as described in example 3 herein. Non-limiting examples of the xanthan gum degrading activity include endoglucanase EC 3.2.1.4 activity.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to containing a GH9 endoglucanase as described herein and/or xanthan lyase, the detergent formulation may contain one or more additional enzymes (such as xanthan lyases, proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transfer-ase(s), hydrolytic enzymes, oxido reductases, bluing agents and fluorescent dyes, antioxidants, and solubilizers.

Dish wash: The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Endoglucanase: The term "endoglucanase" or "EG" means an endo-1,4-(1,3;1,4)-beta-D-glucan 4-glucanohydrolase (EC 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans, xyloglucans, xanthans and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). A non-limiting assay for measuring endoglucanase activity is the reducing sugar assay as described in example 3 herein. Non-limiting examples of endoglucanases include the mature parent endoglucanase having SEQ ID NO: 2.

Enzyme detergency benefit: The term "enzyme detergency benefit" is defined herein as the advan-tageous effect an enzyme may add to a detergent compared to the same detergent without the enzyme. Important detergency benefits which can be provided by enzymes are stain removal with no or very little visible soils after washing and or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils are also important for enzyme detergency benefits. Examples of such textile care benefits are prevention or reduction of dye transfer from one fabric to another fabric or another part of the same fabric an effect that is also termed dye transfer inhibition or anti-backstaining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide; wherein the fragment has endoglucanase activity. In one aspect, a fragment contains at least 85%, 86%, 87%, 88%, 89%, 90%, 91%, 92%, 93%, 94% or 95% of the number of amino acids of the mature polypeptide.

Endoglucanase variant having activity on xanthan gum pre-treated with xanthan lyase: The term "Endoglucanase variant having activity on xanthan gum pre-treated with xanthan lyase" or an "endoglucanase having activity on xanthan gum pre-treated with xanthan lyase and belonging to the GH9 class of glycosyl hydrolases" is defined as a polypeptide comprising a domain belonging to the GH9 class of glycosyl hydrolases, and having activity (e.g. enzymatic activity, xanthan degrading activity, endoglucanase EC 3.2.1.4 activity) on xanthan gum pre-treated with xanthan lyase. A non-limiting assay for measuring activity on xanthan gum pre-treated with xanthan lyase is disclosed in example 3 herein.

Xanthan lyase variant having activity on xanthan gum: The term "Xanthan lyase variant having activity on xanthan gum" is defined as a polypeptide that cleaves the β-D-mannosyl-β-D-1,4-glucuronosyl bond of xanthan (e.g., xanthan lyase EC 4.2.2.12 activity). Examples of the xanthan lyase variants having activity on xanthan gum, are xanthan lyase polypeptides as such. Thus, polypeptides that that cleaves the β-D-mannosyl-β-D-1,4-glucuronosyl bond of xanthan.

Half-life: the term "half-life" is the time it takes for an enzyme to lose half of its enzymatic activity under a given set of conditions. It is denoted as T ½ and is measured in hours (hrs). Half-lives can be calculated at a given detergent concentration and storage temperature for parent (e.g. wild-type) and/or variants, as the degradation follows an exponential decay and the incubation time (hours) is known, i.e., according to the following formulas:

$$T1/2(\text{variant}) = (Ln(0.5)/Ln(\text{RA-variant}/100)) * \text{Time}$$

$$T1/2(\text{wild-type}) = (Ln(0.5)/Ln(\text{RA-wild-type}/100)) * \text{Time}$$

Where 'RA' is the residual activity in percent and 'Time' is the incubation time in hours.

Half-life improvement factor: the term "Half-life improvement factor" or "HIF" is the improvement of half-life of a variant compared to the parent polypeptide, such as the parent endoglucanase. A half-life improvement factor (HIF) under a given set of storage conditions (detergent concentration and temperature) can be calculated as:

$$HIF = \frac{T1/2, \text{variant}}{T1/2, wt}$$

where the wild-type (wt) is incubated under the same storage condition (detergent concentration and incubation temperature) as the variant. In the cases where the difference in stability between wild-type and variant is too big to accurately assess half-life for both wild-type and variant using the same incubation time, the incubation time for wild-type and variant is different e.g. 1 h for wild-type and 138 h for the most stable variants.

A non-limiting way of calculating HIF is also described in example 3 herein.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Host cell: The term "host cell" means any cell type that is susceptible to transformation, transfection, transduction, or the like with a nucleic acid construct or expression vector comprising a polynucleotide. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, catalytic efficiency, catalytic rate, chemical stability, oxidation stability, pH activity, pH stability, specific activity, stability under storage conditions, chelator stability, substrate binding, substrate cleavage, substrate specificity, substrate stability, surface properties, thermal activity, and thermostability.

Improved wash performance: The term "improved wash performance" is defined herein as a (variant) enzyme (also a blend of enzymes, not necessarily only variants but also backbones, and in combination with certain cleaning composition etc.) displaying an alteration of the wash performance of a variant relative to the wash performance of the parent variant e.g. by increased stain removal. The term "wash performance" includes wash performance in laundry but also e.g. in dish wash.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Laundering: The term "laundering" relates to both household laundering and industrial laundering and means the process of treating textiles with a solution containing a cleaning or detergent composition. The laundering process can for example be carried out using e.g. a household or an industrial washing machine or can be carried out by hand.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 1055 of SEQ ID NO: 2.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having enzymatic activity such as activity on xanthan gum pre-treated with xanthan lyase or xanthan lyase activity. In one aspect, the mature polypeptide coding sequence is nucleotides 1 to 3165 of SEQ ID NO: 1.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent: The term "parent" or "parent endoglucanase" means any polypeptide with endoglucanase activity to which an alteration is made to produce the enzyme variants. In one aspect, the parent is an endoglucanase having the identical amino acid sequence of the variant, but not having the alterations at one or more of the specified positions. It will be understood, that the expression "having identical amino acid sequence" relates to 100% sequence identity. Non-limiting examples of parent endoglucanases include the mature parent endoglucanase having SEQ ID NO: 2.

Sequence identity: The relatedness between two amino acid sequences or between two nucleotide sequences is described by the parameter "sequence identity". For purposes, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), such as version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), such as version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having enzymatic activity, such as activity on xanthan gum pre-treated with xanthan lyase or xanthan lyase activity.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabbit and silk or synthetic polymer such as nylon, aramid, polyester, acrylic, polypropylene and spandex/elastane, or blends thereof as well as blend of cellulose based and non-cellulose based fibers.

Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Textile care benefit: "Textile care benefits", which are not directly related to catalytic stain removal or prevention of redeposition of soils, are also important for enzyme detergency benefits. Examples of such textile care benefits are prevention or reduction of dye transfer from one textile to another textile or another part of the same textile an effect that is also termed dye transfer inhibition or anti-backstaining, removal of protruding or broken fibers from a textile surface to decrease pilling tendencies or remove already existing pills or fuzz an effect that also is termed anti-pilling, improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species.

Variant: The term "variant" means a polypeptide (e.g., a GH9 endoglucanase polypeptide) comprising an alteration i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g. several) amino acids e.g., 1-5 amino acids adjacent to and immediately following the amino acid occupying a position. Non-limiting examples of endoglucanase variants as described herein include endoglucanase variants having an activity on xanthan gum pre-treated with xanthan lyase. Non-limiting examples of variants as described herein further include variants having at least 20%, e.g., at least 40%, at least 50%, at least 60%, at least 70%, at least 80%, at least 90%, at least 95%, or at least 100% endoglucanase activity of the mature parent having SEQ ID NO: 2. A non-limiting assay for measuring activity on xanthan gum pre-treated with xanthan lyase is disclosed in example 3 herein.

Stability: The term "stability" means resistance or the degree of resistance to change, unfolding, disintegration, denaturation or activity loss. Non-limiting examples of stability include conformational stability, storage stability and stability during use, e.g. during a wash process and reflects the stability of a polypeptide (e.g. an endoglucanase variant) as a function of time, e.g. how much activity is retained when said polypeptide (e.g. said endoglucanase variant) is kept in solution, in particular in a detergent solution. The stability is influenced by many factors, e.g. presence of chelator(s), pH, temperature, detergent composition, e.g. amount of builders, surfactants, chelators etc. The endoglucanase stability may be measured using a half-life improvement factor (HIF) as described in example 3 herein. The endoglucanase stability may also be measured using a reducing sugar assay as described in example 3 herein.

Improved stability: The term "improved stability" or "increased stability" is defined herein as increased stability in a detergent composition (e.g., in solutions), relative to the stability of the parent endoglucanase, relative to an endoglucanase having the identical amino acid sequence of the variant, but not having the alterations at one or more of the specified positions, or relative to SEQ ID NO: 2. The terms "improved stability" and "increased stability" includes "improved chemical stability", "detergent stability" and "improved detergent stability.

Improved chemical stability: The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants being more able (e.g., better that the parent) to catalyze a reaction in the presence of such chemicals. In a particular aspect the improved chemical stability is an improved stability in a detergent, in particular in a liquid detergent. The term "detergent stability" or "improved detergent stability is in particular an improved stability of the endoglucanase compared to the parent endoglucanase, when an endoglucanase variant as described herein is mixed into a liquid detergent formulation, especially into a liquid detergent formulation comprising a chelator (e.g. EDTA or citrate).

Conformational stability: The term "conformational stability" means resistance or a degree of resistance to conformational change, unfolding or disintegration. Accordingly, the term "less conformationally stable" means less resistant or having lesser degree of resistance to conformational change, unfolding or disintegration.

Instability: The term "instability" means lack of stability. Non-limiting examples of instability include conformational instability, unfolding, denaturation, disintegration, activity loss.

Wash performance: The term "wash performance" is used as an enzyme's ability to remove stains present on the object to be cleaned during e.g. wash or hard surface cleaning. The improvement in the wash performance may be quantified by calculating the so-called intensity value (Int) in 'Automatic Mechanical Stress Assay (AMSA) for laundry' or the remission value (Rem) as defined herein.

Conventions for Designation of Variants

For purposes, the mature polypeptide disclosed in SEQ ID NO: 2 is used to determine the corresponding amino acid residue in another endoglucanase. The amino acid sequence of another endoglucanase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another endoglucanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bio-*

*informatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Altschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implemen-tation of these algorithms can additionally be utilized to query structure databases with a structure of interest in order to discover possible structural homologs (e.g., Holm and Park, 2000, *Bioinformatics* 16: 566-567).

In describing the variants, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Multiple alteration variants may also be separated by a comma (","), e.g., "Arg170Tyr,Gly195Glu" or "R170Y,G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION

The known xanthan endoglucanase having SEQ ID NO: 2 is a large enzyme (>1000 residues), it is therefore extremely laborious and expensive to target its properties for improvement of, e.g. stability in a detergent composition. In some aspects, a non-limiting embodiment has targeted specific regions of the endoglucanase which have an effect on the stability of the endoglucanase molecules using protein engineering to a region selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2.

In one embodiment the detergent compositions dramatically decrease the number of residues to target when trying to stabilize endoglucanase molecules using protein engineering.

Variants

In one embodiment, regions in the protein sequence of the known xanthan endoglucanase having SEQ ID NO: 2 that are affected when the molecule is incubated in detergent, are the following: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2. This embodiment relates to an important guidance on where to mutate an endoglucanase in order to stabilize its molecule in a detergent.

In one embodiment a detergent composition may include an endoglucanase variant, comprising an alteration (e.g., a substitution, deletion or insertion) at one or more positions in a region selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2; said endoglucanase variant has activity on xanthan gum pre-treated with xanthan lyase, said activity is a xanthan gum degrading activity.

In one embodiment, a detergent composition may include an endoglucanase variant, comprising an alteration (e.g., a substitution, deletion or insertion) at one or more positions in a region selected from the group consisting of:

i) region 10 corresponding to amino acids 1 to 94 of SEQ ID NO: 2, e.g., said alteration at one or more positions selected from the group consisting of positions: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, wherein said positions correspond to amino acid positions of SEQ ID NO: 2 (e.g., using the numbering of SEQ ID NO: 2), ii) region 11 corresponding to amino acids 106 to 114 of SEQ ID NO: 2, e.g., said alteration at one or more positions selected from the group consisting of positions: 107, 108, 109, 110, 111, 112, 113, 114, wherein said positions correspond to amino acid positions of SEQ ID NO: 2 (e.g., using the numbering of SEQ ID NO: 2), iii) region 12 corresponding to amino acids 139 to 209 of SEQ ID NO: 2, e.g., said alteration at one or more positions selected from the group consisting of positions: 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, wherein said positions correspond to amino acid positions of SEQ ID NO: 2 (e.g., using the numbering of SEQ ID NO: 2), iv) region 13 corresponding to amino acids 252 to 266 of SEQ ID NO: 2, e.g., said alteration at one or more positions selected from the group consisting of positions: 252, 253, 254, 255, 256, 257, 258, 259, 260, 261, 262, 263, 264, 265, 266, wherein said positions correspond to amino acid positions of SEQ ID NO: 2 (e.g., using the numbering of SEQ ID NO: 2), v) region 14 corresponding to amino acids 302 to 338 of SEQ ID NO: 2, e.g., said alteration at one or more positions selected from the group consisting of positions: 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, wherein said positions correspond to amino acid positions of SEQ ID NO: 2 (e.g., using the numbering of SEQ ID NO: 2), vi) region 15 corresponding to amino acids 362 to 546 of SEQ ID NO: 2, e.g., said alteration at one or more positions selected from the group consisting of positions: 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, wherein said positions correspond to amino acid positions of SEQ ID NO: 2 (e.g., using the numbering of SEQ ID NO: 2), vii) region 16 corresponding to amino acids 596 to 611 of SEQ ID NO: 2, e.g., said alteration at one or more positions selected from the group consisting of positions: 596, 597, 598, 599, 600, 601, 602, 603, 604, 605, 606, 607, 608, 609, 610, 611, wherein said positions correspond to amino acid positions of SEQ ID NO: 2 (e.g., using the numbering of SEQ ID NO: 2), viii) region 17 corresponding to amino acids 661 to 805 of SEQ ID NO: 2, e.g., said alteration at one or more positions selected from the group consisting of positions: 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, wherein said positions correspond to amino acid positions of SEQ ID NO: 2 (e.g., using the numbering of SEQ ID NO: 2), ix) region 18 corresponding to amino acids 829 to 838 of SEQ ID NO: 2, e.g., said alteration at one or more positions selected from the group consisting of positions:

829, 830, 831, 832, 833, 834, 835, 836, 837, 838, wherein said positions correspond to amino acid positions of SEQ ID NO: 2 (e.g., using the numbering of SEQ ID NO: 2) x) region 19 corresponding to amino acids 1043 to 1055 of SEQ ID NO: 2, e.g., said alteration at one or more positions selected from the group consisting of positions 1043, 1044, 1045, 1046, 1047, 1048, 1049, 1050, 1051, 1052, 1053, 1054, 1055, wherein said positions correspond to amino acid positions of SEQ ID NO: 2 (e.g., using the numbering of SEQ ID NO: 2).

In one embodiment a detergent composition may include an endoglucanase variant, comprising an alteration (e.g., a substitution, deletion or insertion) at one or more positions in one or more regions selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2, wherein said variant has at least 60% and less than 100% sequence identity to SEQ ID NO: 2; said endoglucanase variant has activity on xanthan gum pre-treated with xanthan lyase, said activity is a xanthan gum degrading activity.

In one embodiment a detergent composition may include an endoglucanase variant as described herein having multiple alterations (such as 2, 3, 4, 5, 6, 7, 8, 9 or 10) in one region (e.g., of SEQ ID NO: 2 or another parent endoglucanase) selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2, wherein said variant has at least 60% and less than 100% sequence identity to SEQ ID NO: 2, said endoglucanase variant has activity on xanthan gum pre-treated with xanthan lyase, said activity is a xanthan gum degrading activity.

In one embodiment a detergent composition may include an endoglucanase variant as described herein having multiple alterations (e.g., 2, 3, 4, 5, 6, 7, 8, 9 or 10) in multiple regions (e.g., 2, 3, 4, 5, 6, 7, 8, 9 or 10) (e.g., of SEQ ID NO: 2 or another parent endoglucanase) selected from the group consisting of: region 10 corresponding to amino acids 1 to 94 of SEQ ID NO: 2, region 11 corresponding to amino acids 106 to 114 of SEQ ID NO: 2, region 12 corresponding to amino acids 139 to 209 of SEQ ID NO: 2, region 13 corresponding to amino acids 252 to 266 of SEQ ID NO: 2, region 14 corresponding to amino acids 302 to 338 of SEQ ID NO: 2, region 15 corresponding to amino acids 362 to 546 of SEQ ID NO: 2, region 16 corresponding to amino acids 596 to 611 of SEQ ID NO: 2, region 17 corresponding to amino acids 661 to 805 of SEQ ID NO: 2, region 18 corresponding to amino acids 829 to 838 of SEQ ID NO: 2, and region 19 corresponding to amino acids 1043 to 1055 of SEQ ID NO: 2, said endoglucanase variant has activity on xanthan gum pre-treated with xanthan lyase, said activity is a xanthan gum degrading activity.

In one embodiment, detergent compositions may include endoglucanase variants, comprising an alteration (e.g., a substitution, deletion or insertion) at one or more (e.g., several) positions of the mature parent polypeptide (e.g., SEQ ID NO: 2), wherein each alteration is independently a substitution, insertion or deletion, wherein the variant has endoglucanase activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent endoglucanase.

In one embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

In one embodiment a detergent composition may include an endoglucanase variant, wherein said variant has at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

In another aspect, a variant comprises an alteration at one or more (e.g., several) positions corresponding to positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2, wherein numbering is according to SEQ ID NO: 2.

In one embodiment, the endoglucanase variant comprised in the detergent compositions further comprises an alteration at one or more positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999 and 1037 of SEQ ID NO: 2.

In another aspect, a variant comprises an alteration at two positions corresponding to any of positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2, wherein numbering is according to SEQ ID NO: 2.

In one embodiment, the endoglucanase variant comprised in the detergent compositions further comprises an alteration at one or more positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999 and 1037 of SEQ ID NO: 2.

In another aspect, a variant comprises an alteration at three positions corresponding to any of positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2, wherein numbering is according to SEQ ID NO: 2.

In one embodiment, the endoglucanase variant comprised in the detergent compositions further comprises an alteration at one or more positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999 and 1037 of SEQ ID NO: 2.

Thus, in one embodiment, the variant comprises an alteration in the positions corresponding to: 17+20, 17+51, 17+53, 17+55, 17+56, 17+60, 17+63, 17+79, 17+87, 17+192, 17+302, 7+387, 17+388, 17+390, 17+403, 17+408, 17+410, 17+416, 17+448, 17+451, 17+471, 17+472, 17+507, 17+512, 17+515, 17+538, 17+598, 17+602, 17+605, 17+609, 17+676, 17+694, 17+698, 17+699, 17+711, 17+754, 17+760, 17+781, 17+786, 17+797, 17+834, 17+835, 20+51, 20+53, 20+55, 20+56, 20+60, 20+63, 20+79, 20+87, 20+192, 20+302, 20+387, 20+388, 20+390, 20+403, 20+408, 20+410, 20+416, 20+448, 20+451, 20+471, 20+472, 20+507, 20+512, 20+515, 20+538, 20+598, 20+602, 20+605, 20+609, 20+676, 20+694, 20+698, 20+699, 20+711, 20+754, 20+760, 20+781, 20+786, 20+797, 20+834, 20+835, 51+53, 51+55, 51+56, 51+60, 51+63, 51+79, 51+87, 51+192, 51+302, 51+387, 51+388, 51+390, 51+403, 51+408, 51+410, 51+416, 51+448, 51+451, 51+471, 51+472, 51+507, 51+512, 51+515, 51+538, 51+598, 51+602, 51+605, 51+609, 51+676, 51+694, 51+698, 51+699, 51+711, 51+754, 51+760, 51+781, 51+786, 51+797, 51+834, 51+835, 53+55, 53+56, 53+60, 53+63, 53+79, 53+87, 53+192, 53+302, 53+387, 53+388, 53+390, 53+403, 53+408, 53+410, 53+416, 53+448, 53+451, 53+471, 53+472, 53+507, 53+512, 53+515, 53+538, 53+598, 53+602, 53+605, 53+609, 3+676, 53+694, 53+698, 53+699, 53+711, 53+754, 53+760, 53+781, 53+786, 53+797, 53+834, 53+835, 55+56, 55+60, 55+63, 55+79, 55+87, 55+192, 55+302, 55+387, 55+388, 55+390, 55+403, 55+408, 55+410, 55+416, 55+448, 55+451, 55+471, 55+472, 55+507, 55+512, 55+515, 55+538, 55+598, 55+602, 55+605, 55+609, 55+676, 55+694, 55+698, 55+699, 55+711, 55+754, 55+760, 55+781, 55+786, 55+797, 55+834, 55+835, 56+60, 56+63, 56+79, 56+87, 56+192, 56+302, 56+387, 56+388, 56+390, 56+403, 56+408, 56+410, 56+416, 56+448, 56+451, 56+471, 56+472, 56+507, 56+512, 56+515, 56+538, 56+598, 56+602, 56+605, 56+609, 56+676, 56+694, 56+698, 56+699, 56+711, 56+754, 56+760, 56+781, 56+786, 56+797, 56+834, 56+835, 60+63, 60+79, 60+87, 60+192, 60+302, 60+387, 60+388, 60+390, 60+403, 60+408, 60+410, 60+416, 60+448, 60+451, 60+471, 60+472, 60+507, 60+512, 60+515, 60+538, 60+598, 60+602, 60+605, 60+609, 60+676, 60+694, 60+698, 60+699, 60+711, 60+754, 60+760, 60+781, 60+786, 60+797, 60+834, 60+835, 63+79, 63+87, 63+192, 63+302, 63+387, 63+388, 63+390, 63+403, 63+408, 63+410, 63+416, 63+448, 63+451, 63+471, 63+472, 63+507, 63+512, 63+515, 63+538, 63+598, 63+602, 63+605, 63+609, 63+676, 63+694, 63+698, 63+699, 63+711, 63+754, 63+760, 63+781, 63+786, 63+797, 63+834, 63+835, 79+87, 79+192, 79+302, 79+387, 79+388, 79+390, 79+403, 79+408, 79+410, 79+416, 79+448, 79+451, 79+471, 79+472, 79+507, 79+512, 79+515, 79+538, 79+598, 79+602, 79+605, 79+609, 79+676, 79+694, 79+698, 79+699, 79+711, 79+754, 79+760, 79+781, 79+786, 79+797, 79+834, 79+835, 87+192, 87+302, 87+387, 87+388, 87+390, 87+403, 87+408, 87+410, 87+416, 87+448, 87+451, 87+471, 87+472, 87+507, 87+512, 87+515, 87+538, 87+598, 87+602, 87+605, 87+609, 87+676, 87+694, 87+698, 87+699, 87+711, 87+754, 87+760, 87+781, 87+786, 87+797, 87+834, 87+835, 192+302, 192+387, 192+388, 192+390, 192+403, 192+408, 192+410, 192+416, 192+448, 192+451, 192+471, 192+472, 192+507, 192+512, 192+515, 192+538, 192+598, 192+602, 192+605, 192+609, 192+676, 192+694, 192+698, 192+699, 192+711, 192+754, 192+760, 192+781, 192+786, 192+797, 192+834, 192+835, 302+387, 302+388, 302+390, 302+403, 302+408, 302+410, 302+416, 302+448, 302+451, 302+471, 302+472, 302+507, 302+512, 302+515, 302+538, 302+598, 302+602, 302+605, 302+609, 302+676, 302+694, 302+698, 302+699, 302+711, 302+754, 302+760, 302+781, 302+786, 302+797, 302+834, 302+835, 387+388, 387+390, 387+403, 387+408, 387+410, 387+416, 387+448, 387+451, 387+471, 387+472, 387+507, 387+512, 387+515, 387+538, 387+598, 387+602, 387+605, 87+609, 387+676, 387+694, 387+698, 387+699, 387+711, 387+754, 387+760, 387+781, 387+786, 387+797, 387+834, 387+835, 388+390, 388+403, 388+408, 388+410, 388+416, 388+448, 388+451, 388+471, 388+472, 388+507, 388+512, 388+515, 388+538, 388+598, 388+602, 388+605, 388+609, 388+676, 388+694, 388+698, 388+699, 388+711, 388+754, 388+760, 388+781, 388+786, 388+797, 388+834, 388+835, 390+403, 390+408, 390+410, 390+416, 390+448, 390+451, 390+471, 390+472, 390+507, 390+512, 390+515, 390+538, 390+598, 390+602, 390+605, 390+609, 390+676, 390+694, 390+698, 390+699, 390+711, 390+754, 390+760, 390+781, 390+786, 390+797, 390+834, 390+835, 403+408, 403+410, 403+416, 403+448, 403+451, 403+471, 403+472, 403+507, 403+512, 403+515, 403+538, 403+598, 403+602, 403+605, 403+609, 403+676, 403+694, 403+698, 403+699, 403+711, 403+754, 403+760, 403+781, 403+786, 403+797, 403+834, 403+835, 408+410, 408+416, 408+448, 408+451, 408+471, 408+472, 408+507, 408+512, 408+515, 408+538, 408+598, 408+602, 408+605, 408+609, 408+676, 408+694, 408+698, 408+699, 408+711, 408+754, 408+760, 408+781, 408+786, 408+797, 408+834, 408+835, 410+416, 410+448, 410+451, 410+471, 410+472, 410+507, 410+512, 410+515, 410+538, 410+598, 410+602, 410+605, 410+609, 410+676, 410+694, 410+698, 410+699, 410+711, 410+754, 410+760, 410+781, 410+786, 410+797, 410+834, 410+835, 416+448, 416+451, 416+471, 416+472, 416+507, 416+512, 416+515, 416+538, 416+598, 416+602, 416+605, 416+609, 416+676, 416+694, 416+698, 416+699, 416+711, 416+754, 416+760, 416+781, 416+786, 416+797, 416+834, 416+835, 448+451, 448+471, 448+472, 448+507, 448+512, 448+515, 448+538, 448+598, 448+602, 448+605, 448+609, 448+676, 448+694, 448+698, 448+699, 448+711, 448+754, 448+760, 448+781, 448+786, 448+797, 448+834, 448+835, 451+471, 451+472, 451+507, 451+512, 451+515, 451+538, 451+598, 451+602, 451+605, 451+609, 451+676, 451+694, 451+698, 451+699, 451+711, 451+754, 451+760, 451+781, 451+786, 451+797, 451+834, 451+835, 471+472, 471+507, 471+512, 471+515, 471+538, 471+598, 471+602, 471+605, 471+609, 471+676, 471+694, 471+698, 471+699, 471+711, 471+754, 471+760, 471+781, 471+786, 471+797, 471+834, 471+835, 472+507, 472+512, 472+515, 472+538, 472+598, 472+602, 472+605, 472+609, 472+676, 472+694, 472+698, 472+699, 472+711, 472+754, 472+760, 472+781, 472+786, 472+797, 472+834, 472+835, 507+512, 507+515, 507+538, 507+598, 507+602, 507+605, 507+609, 507+676, 507+694, 507+698, 507+699, 507+711, 507+754, 507+760, 507+781, 507+786, 507+797, 507+834, 507+835, 512+515, 512+538, 512+598, 512+602, 512+605, 512+609, 512+676, 512+694, 512+698, 512+699, 512+711, 512+754, 512+760, 512+781, 512+786, 512+797, 512+834, 512+835, 515+538, 515+598, 515+602, 515+605, 515+609, 515+676, 515+694, 515+698, 515+699, 515+711, 515+754, 515+760, 515+781, 515+786, 515+797, 515+834, 515+835, 538+598, 538+602, 538+605, 538+609, 538+676, 538+694, 538+698, 538+699, 538+711, 538+754, 538+760, 538+781, 538+786, 538+797, 538+834, 538+835, 598+602, 598+605, 598+609, 598+676, 598+694, 598+698, 598+699, 598+711, 598+754, 598+760, 598+781, 598+786, 598+797, 598+834, 598+835, 602+605, 602+609, 602+676, 602+694, 602+698, 602+699, 602+711, 602+754, 602+760, 602+781, 602+786, 602+797, 602+834, 602+835, 605+609, 605+676, 605+694, 605+698, 605+699, 605+711, 605+754, 605+760, 605+781, 605+786, 605+797, 605+834, 605+835, 609+676, 609+694, 609+698, 609+699, 609+711, 609+754, 609+760, 609+781, 609+786, 609+797, 609+834, 609+835, 676+694, 676+698, 676+699, 676+711, 676+754, 676+760, 676+781, 676+786, 676+797, 676+834, 676+835, 694+698, 694+699, 694+711, 694+754, 694+760, 694+781, 694+786, 694+797, 694+834, 694+835, 698+699, 698+711, 698+754, 698+760, 698+781, 698+786, 698+797, 698+834, 698+835, 699+711, 699+754, 699+760, 699+781, 699+786, 699+797, 699+834, 699+835, 711+754, 711+760, 711+781, 711+786, 711+797, 711+834, 711+835, 754+760, 754+781, 754+786, 754+797, 754+834, 754+835 760+781, 760+786, 760+797, 760+834, 760+835, 781+786, 781+797, 781+834, 781+835,786+797,786+834,786+835,797+834,797+835, 834+835, 17+20+51, 17+20+53, 17+20+55, 17+20+56,17+20+60,17+20+63,17+20+79,17+20+87,17+20+192,17+20+302,17+20+387,17+20+388, 17+20+390, 17+20+403, 17+20+408, 17+20+410, 17+20+416, 17+20+448, 17+20+451, 17+20+471, 7+20+472, 17+20+507, 17+20+512, 17+20+515, 17+20+538, 17+20+598, 17+20+602, 17+20+605, 17+20+609, 17+20+676, 17+20+694, 17+20+698, 17+20+699, 17+20+711, 17+20+754, 17+20+760, 17+20+781, 17+20+786, 17+20+797, 17+20+834, 17+20+835, 17+51+53, 17+51+55, 17+51+56, 17+51+60, 17+51+63, 17+51+79, 17+51+87, 17+51+192, 17+51+302, 17+51+387, 17+51+388, 17+51+390, 17+51+403, 17+51+408, 17+51+410, 17+51+416, 17+51+448, 17+51+451, 17+51+471, 17+51+472, 17+51+507, 17+51+512, 17+51+515, 17+51+538, 17+51+598, 17+51+602, 17+51+605, 17+51+609, 17+51+676, 17+51+694, 17+51+698, 17+51+699, 17+51+711, 17+51+754, 17+51+760, 17+51+781, 17+51+786, 17+51+797, 17+51+834, 17+51+835, 17+53+55, 17+53+56, 17+53+60, 17+53+63, 17+53+79, 17+53+87, 17+53+192, 17+53+302, 17+53+387, 17+53+388, 17+53+390, 17+53+403, 17+53+408, 17+53+410, 17+53+416, 17+53+448, 17+53+451, 17+53+471, 17+53+472, 17+53+507, 17+53+512, 17+53+515, 17+53+538, 17+53+598, 17+53+602, 17+53+605, 17+53+609, 17+53+676, 17+53+694, 17+53+698, 17+53+699, 17+53+711, 17+53+754, 17+53+760, 17+53+781, 17+53+786,17+53+797,17+53+834,17+53+835,17+55+56,17+55+60,17+55+63,17+55+79, 17+55+87, 17+55+192, 17+55+302, 17+55+387, 17+55+388, 17+55+390, 17+55+403, 17+55+408, 17+55+410, 17+55+416, 17+55+448, 17+55+451, 17+55+471, 17+55+472, 17+55+507, 17+55+512, 17+55+515, 17+55+538, 17+55+598, 17+55+602, 17+55+605, 17+55+609, 17+55+676, 17+55+694, 17+55+698, 17+55+699, 17+55+711, 17+55+754, 17+55+760, 17+55+781, 17+55+786, 17+55+797, 17+55+834, 17+55+835, 17+56+60, 17+56+63, 17+56+79, 17+56+87, 17+56+192, 17+56+302, 17+56+387, 17+56+388, 17+56+390, 17+56+403, 17+56+408, 17+56+410, 17+56+416, 17+56+448, 17+56+451, 17+56+471, 17+56+472, 17+56+507, 17+56+512, 17+56+515, 17+56+538, 17+56+598, 17+56+602, 17+56+605, 17+56+609, 17+56+676, 17+56+694, 17+56+698, 17+56+699, 17+56+711, 17+56+754, 17+56+760, 17+56+781, 17+56+786, 17+56+797, 17+56+834, 17+56+835, 17+60+63, 17+60+79, 17+60+87, 17+60+192, 17+60+302, 17+60+387, 17+60+388, 17+60+390, 17+60+403, 17+60+408, 17+60+410, 17+60+416, 17+60+448, 17+60+451, 17+60+471, 17+60+472, 17+60+507, 17+60+512, 17+60+515, 17+60+538, 17+60+598, 17+60+602, 17+60+605, 17+60+609, 17+60+676, 17+60+694, 17+60+698, 17+60+699, 17+60+711, 17+60+754, 17+60+760, 17+60+781, 17+60+786, 17+60+797, 17+60+834, 17+60+835, 17+63+79, 17+63+87, 17+63+192, 17+63+302, 17+63+387, 17+63+388, 17+63+390, 17+63+403, 17+63+408, 17+63+410, 17+63+416, 17+63+448, 17+63+451, 17+63+471, 17+63+472, 17+63+507, 17+63+512, 17+63+515, 17+63+538, 17+63+598, 17+63+602, 17+63+605, 17+63+609, 17+63+676, 17+63+694, 17+63+698, 17+63+699, 17+63+711, 17+63+754, 17+63+760, 17+63+781, 17+63+786, 17+63+797, 17+63+834, 17+63+835, 17+79+87, 17+79+192, 17+79+302, 17+79+387, 17+79+388, 17+79+390, 17+79+403, 17+79+408, 17+79+410, 17+79+416, 17+79+448, 17+79+451, 17+79+471, 17+79+472, 17+79+507, 17+79+512, 17+79+515, 17+79+538, 17+79+598, 17+79+602, 17+79+605, 17+79+609, 17+79+676, 17+79+694, 17+79+698, 17+79+699, 17+79+711, 17+79+754, 17+79+760, 17+79+781, 17+79+786, 17+79+797, 17+79+834, 17+79+835, 17+87+192, 17+87+302, 17+87+387, 17+87+388, 17+87+390, 17+87+403, 17+87+408, 17+87+410, 17+87+416, 17+87+448, 17+87+451, 17+87+471, 17+87+472, 17+87+507, 17+87+512, 17+87+515, 17+87+538, 17+87+598, 17+87+602, 17+87+605, 17+87+609, 17+87+676, 17+87+694, 17+87+698, 17+87+699, 17+87+711, 17+87+754, 17+87+760, 17+87+781, 17+87+786, 17+87+797, 17+87+834, 17+87+835, 17+192+302, 17+192+387, 17+192+388, 17+192+390, 17+192+403, 17+192+408, 17+192+410, 17+192+416, 17+192+448, 17+192+451, 17+192+471, 17+192+472, 17+192+507, 17+192+512, 17+192+515, 17+192+538, 17+192+598, 17+192+602, 17+192+605, 17+192+609, 17+192+676, 17+192+694, 17+192+698, 17+192+699, 17+192+711, 17+192+754, 17+192+760, 17+192+781, 17+192+786, 17+192+797, 17+192+834, 17+192+835, 17+302+387, 17+302+388, 17+302+390, 17+302+403, 17+302+408, 17+302+410, 17+302+416, 17+302+448, 17+302+451, 17+302+471, 17+302+472, 17+302+507, 17+302+512, 17+302+515, 17+302+538, 17+302+598, 17+302+602, 17+302+605, 17+302+609, 17+302+676, 17+302+694, 17+302+698, 17+302+699, 17+302+711, 17+302+754, 17+302+760, 17+302+781, 17+302+786, 17+302+797, 17+302+834, 17+302+835, 17+387+388, 17+387+390, 17+387+403, 17+387+408, 17+387+410, 17+387+416, 17+387+448, 17+387+451, 17+387+471, 17+387+472, 17+387+507, 17+387+512, 17+387+515, 17+387+538, 17+387+598, 17+387+602, 17+387+605, 17+387+609, 17+387+676, 17+387+694, 17+387+698, 17+387+699, 17+387+711, 17+387+754, 17+387+760, 17+387+781, 17+387+786, 17+387+797, 17+387+834, 17+387+835, 17+388+390, 17+388+403, 17+388+408, 17+388+410, 17+388+416, 17+388+448, 17+388+451, 17+388+471, 17+388+472, 17+388+507, 17+388+512, 17+388+515, 17+388+538, 17+388+598, 17+388+602, 17+388+605, 17+388+609, 17+388+676, 17+388+694, 17+388+698, 17+388+699, 17+388+711, 17+388+754, 17+388+760, 17+388+781, 17+388+786, 17+388+797, 17+388+834, 17+388+835, 17+390+403, 17+390+408, 17+390+410, 17+390+416, 17+390+448, 17+390+451, 17+390+471, 17+390+472, 17+390+507, 17+390+512, 17+390+515, 17+390+538, 17+390+598, 17+390+602, 17+390+605, 17+390+609, 17+390+676, 17+390+694, 17+390+698, 17+390+699, 17+390+711, 17+390+754, 17+390+760, 17+390+781, 17+390+786, 17+390+797, 17+390+834, 17+390+835, 17+403+408, 17+403+410, 17+403+416, 17+403+448, 17+403+451, 17+403+471, 17+403+472, 17+403+507, 17+403+512, 17+403+515, 17+403+538, 17+403+598, 17+403+602, 17+403+605, 17+403+609, 17+403+676, 17+403+694, 17+403+698, 17+403+699, 17+403+711, 17+403+754, 17+403+760, 17+403+781, 17+403+786, 17+403+797, 17+403+834, 17+403+835, 17+408+410, 17+408+416, 17+408+448, 17+408+451, 17+408+471, 17+408+472, 17+408+507, 17+408+512, 17+408+515, 17+408+538, 17+408+598, 17+408+602, 17+408+605, 17+408+609, 17+408+676, 17+408+694, 17+408+698, 17+408+699, 17+408+711, 17+408+754, 17+408+760, 17+408+781, 17+408+786, 17+408+797, 17+408+834, 17+408+835, 17+410+416, 17+410+448, 17+410+451, 17+410+471, 17+410+472, 17+410+507, 17+410+512, 17+410+515, 17+410+538, 17+410+598, 17+410+602, 17+410+605, 17+410+609, 17+410+676, 17+410+694, 17+410+698, 17+410+699, 17+410+711, 17+410+754, 17+410+760, 17+410+781, 17+410+786, 17+410+797, 17+410+834, 17+410+835, 17+416+448, 17+416+451, 17+416+471, 17+416+472, 17+416+507, 17+416+512, 17+416+515, 17+416+538, 17+416+598, 17+416+602, 17+416+605, 17+416+609, 17+416+676, 17+416+694, 17+416+698, 17+416+699, 7+416+711, 17+416+754, 17+416+760, 17+416+781, 17+416+786, 17+416+797, 17+416+834, 17+416+835, 17+448+451, 17+448+471, 17+448+472, 17+448+507, 17+448+512, 17+448+515, 17+448+538, 17+448+598, 17+448+602, 17+448+605, 17+448+609, 17+448+676, 17+448+694, 17+448+698, 17+448+699, 17+448+711, 17+448+754, 17+448+760, 17+448+781, 17+448+786, 17+448+797, 17+448+834, 17+448+835, 17+451+471, 17+451+472, 17+451+507, 17+451+512, 17+451+515, 17+451+538, 17+451+598, 17+451+602, 17+451+605, 17+451+609, 17+451+676, 17+451+694, 17+451+698, 17+451+699, 17+451+711, 17+451+754, 17+451+760, 17+451+781, 17+451+786, 17+451+797, 17+451+834, 17+451+835, 17+471+472, 17+471+507, 17+471+512, 17+471+515, 17+471+538, 17+471+598, 17+471+602, 17+471+605, 17+471+609, 17+471+676, 17+471+694, 17+471+698, 17+471+699, 17+471+711, 17+471+754, 17+471+760, 17+471+781, 17+471+786, 17+471+797, 17+471+834, 17+471+835, 17+472+507, 17+472+512, 17+472+515, 17+472+538, 17+472+598, 17+472+602, 17+472+605, 17+472+609, 17+472+676, 17+472+694, 17+472+698, 17+472+699, 17+472+711, 17+472+754, 17+472+760, 17+472+781, 17+472+786, 17+472+797, 17+472+834, 17+472+835, 17+507+512, 17+507+515, 17+507+538, 17+507+598, 17+507+602, 17+507+605, 17+507+609, 17+507+676, 17+507+694, 17+507+698, 17+507+699, 17+507+711, 17+507+754, 17+507+760, 17+507+781, 17+507+786, 17+507+797, 17+507+834, 17+507+835, 17+512+515, 17+512+538, 17+512+598, 17+512+602, 17+512+605, 17+512+609, 17+512+676, 17+512+694, 17+512+698, 17+512+699, 17+512+711, 17+512+754, 17+512+760, 17+512+781, 17+512+786, 17+512+797, 17+512+834, 17+512+835, 17+515+538, 17+515+598, 17+515+602, 17+515+605, 17+515+609, 17+515+676, 17+515+694, 17+515+698, 17+515+699, 17+515+711, 17+515+754, 17+515+760, 17+515+781, 17+515+786, 17+515+797, 17+515+834, 17+515+835, 17+538+598, 17+538+602, 17+538+605, 17+538+609, 17+538+676, 17+538+694, 17+538+698, 17+538+699, 17+538+711, 17+538+754, 17+538+760, 17+538+781, 17+538+786, 17+538+797, 17+538+834, 17+538+835, 17+598+602, 17+598+605, 17+598+609, 17+598+676, 17+598+694, 17+598+698, 17+598+699, 17+598+711, 17+598+754, 17+598+760, 17+598+781, 17+598+786, 17+598+797, 17+598+834, 17+598+835, 17+602+605, 17+602+609, 17+602+676, 17+602+694, 17+602+698, 17+602+699, 17+602+711, 17+602+754, 17+602+760, 17+602+781, 17+602+786, 17+602+797, 17+602+834, 17+602+835, 17+605+609, 17+605+676, 17+605+694, 17+605+698, 17+605+699, 17+605+711, 17+605+754, 17+605+760, 17+605+781, 17+605+786, 17+605+797, 17+605+834, 17+605+835, 17+609+676, 17+609+694, 17+609+698, 17+609+699, 17+609+711, 17+609+754, 17+609+760, 17+609+781, 17+609+786, 17+609+797, 17+609+834, 17+609+835, 17+676+694, 17+676+698, 17+676+699, 17+676+711, 17+676+754, 17+676+760, 17+676+781, 17+676+786, 17+676+797, 17+676+834, 17+676+835, 17+694+698, 17+694+699, 17+694+711, 17+694+754, 17+694+760, 17+694+781, 17+694+786, 17+694+797, 17+694+834, 17+694+835, 17+698+699, 17+698+711, 17+698+754, 17+698+760, 17+698+781, 17+698+786, 17+698+797, 17+698+834, 17+698+835, 17+699+711, 17+699+754, 17+699+760, 17+699+781, 17+699+786, 17+699+797, 17+699+834, 17+699+835, 17+711+754, 17+711+760, 17+711+781, 17+711+786, 17+711+797, 17+711+834, 17+711+835, 17+754+760, 17+754+781, 17+754+786, 17+754+797, 17+754+834, 17+754+835, 17+760+781, 17+760+786, 17+760+797, 17+760+834, 17+760+835, 17+781+786, 17+781+797, 17+781+834, 17+781+835, 17+786+797, 17+786+834, 17+786+835, 17+797+834, 17+797+835, 17+834+835, 20+51+53, 20+51+55, 20+51+56, 20+51+60, 20+51+63, 20+51+79, 20+51+87, 20+51+192, 20+51+302, 20+51+387, 20+51+388, 20+51+390, 20+51+403, 20+51+408, 20+51+410, 20+51+416, 20+51+448, 20+51+451, 20+51+471, 20+51+472, 20+51+507, 20+51+512 20+51+515, 20+51+538, 20+51+598, 20+51+602, 20+51+605, 20+51+609, 20+51+676, 20+51+694, 20+51+698, 20+51+699, 20+51+711, 20+51+754, 20+51+760, 20+51+781, 20+51+786, 20+51+797,20+51+834,20+51+835,20+53+55,20+53+56,20+53+60,20+53+63,20+53+79,20+53+87, 20+53+192, 20+53+302, 20+53+387, 20+53+388, 20+53+390, 20+53+403, 20+53+408, 20+53+410, 20+53+416, 20+53+448, 20+53+451, 20+53+471, 20+53+472, 20+53+507, 20+53+512, 20+53+515, 20+53+538, 20+53+598, 20+53+602, 20+53+605, 20+53+609, 20+53+676, 20+53+694, 20+53+698, 20+53+699, 20+53+711, 20+53+754, 20+53+760, 20+53+781, 20+53+786, 20+53+797, 20+53+834, 20+53+835,20+55+56,20+55+60, 20+55+63,20+55+79,20+55+87,20+55+192,20+55+302, 20+55+387, 20+55+388, 20+55+390, 20+55+403, 20+55+408, 20+55+410, 20+55+416, 20+55+448, 20+55+451 20+55+471, 20+55+472, 20+55+507, 20+55+512, 20+55+515, 20+55+538, 20+55+598, 20+55+602, 20+55+605, 20+55+609, 20+55+676, 20+55+694, 20+55+698, 20+55+699, 20+55+711, 20+55+754, 20+55+760, 20+55+781, 20+55+786, 20+55+797, 20+55+834, 20+55+835, 20+56+60, 20+56+63, 20+56+79, 20+56+87, 20+56+192, 20+56+302, 20+56+387, 20+56+388, 20+56+390, 20+56+403, 20+56+408, 20+56+410, 20+56+416, 20+56+448, 20+56+451, 20+56+471, 20+56+472, 20+56+507, 20+56+512, 20+56+515, 20+56+538, 20+56+598, 20+56+602, 20+56+605, 20+56+609, 20+56+676, 20+56+694, 20+56+698, 20+56+699, 20+56+711, 20+56+754, 20+56+760, 20+56+

781, +56+786, 20+56+797, 20+56+834, 20+56+835, 20+60+63, 20+60+79, 20+60+87, 20+60+192, 20+60+302, 20+60+387, 20+60+388, 20+60+390, 20+60+403, 20+60+408, 20+60+410, 20+60+416, 20+60+448, 20+60+451, 20+60+471, 20+60+472, 20+60+507, 20+60+512, 20+60+515, 20+60+538, 20+60+598, 20+60+602, 20+60+605, 20+60+609, 20+60+676, 20+60+694, 20+60+698, 20+60+699, 20+60+711, 20+60+754, 20+60+760, 20+60+781, 20+60+786, 20+60+797, 20+60+834, 20+60+835, 20+63+79, 20+63+87, 20+63+192, 20+63+302, 20+63+387, 20+63+388, 20+63+390, 20+63+403, 20+63+408, 20+63+410, 20+63+416, 20+63+448, 20+63+451, 20+63+471, 20+63+472, 20+63+507, 20+63+512, 20+63+515, 20+63+538, 20+63+598, 20+63+602, 20+63+605, 20+63+609, 20+63+676, 20+63+694, 20+63+698, 20+63+699, 20+63+711, 20+63+754, 20+63+760, 20+63+781, 20+63+786, 20+63+797, 20+63+834, 20+63+835, 20+79+87, 20+79+192, 20+79+302, 20+79+387, 20+79+388, 20+79+390, 20+79+403, 20+79+408, 20+79+410, 20+79+416, 20+79+448, 20+79+451, 20+79+471, 20+79+472, 20+79+507, 20+79+512, 20+79+515, 20+79+538, 20+79+598, 20+79+602, 20+79+605, 20+79+609, 20+79+676, 20+79+694, 20+79+698, 20+79+699, 20+79+711, 20+79+754, 20+79+760, 20+79+781, 20+79+786, 20+79+797, 20+79+834, 20+79+835, 20+87+192, 20+87+302, 20+87+387, 20+87+388, 20+87+390, 20+87+403, 20+87+408, 20+87+410, 20+87+416, 20+87+448, 20+87+451, 20+87+471, 20+87+472, 20+87+507, 20+87+512, 20+87+515, 20+87+538, 20+87+598, 20+87+602, 20+87+605, 20+87+609, 20+87+676, 20+87+694, 20+87+698, 20+87+699, 20+87+711, 20+87+754, 20+87+760, 20+87+781, 20+87+786, 20+87+797, 20+87+834, 20+87+835, 20+192+302, 20+192+387, 20+192+388, 20+192+390, 20+192+403, 20+192+408, 20+192+410, 20+192+416, 20+192+448, 20+192+451, 20+192+471, 20+192+472, 20+192+507, 20+192+512, 20+192+515, 20+192+538, 20+192+598, 20+192+602, 20+192+605, 20+192+609, 20+192+676, 20+192+694, 20+192+698, 20+192+699 20+192+711, 20+192+754, 20+192+760, 20+192+781, 20+192+786, 20+192+797, 20+192+834, 20+192+835, 20+302+387, 20+302+388, 20+302+390, 20+302+403, 20+302+408, 20+302+410, 20+302+416, 20+302+448, 20+302+451, 20+302+471, 20+302+472, 20+302+507, 20+302+512, 20+302+515, 20+302+538, 20+302+598, 20+302+602, 20+302+605, 20+302+609, 20+302+676, 20+302+694, 20+302+698, 20+302+699, 20+302+711, 20+302+754, 20+302+760, 20+302+781, 20+302+786, 20+302+797, 20+302+834, 20+302+835, 20+387+388, 20+387+390, 20+387+403, 20+387+408, 20+387+410, 20+387+416, 20+387+448, 20+387+451, 20+387+471, 20+387+472, 20+387+507, 20+387+512, 20+387+515, 20+387+538, 20+387+598, 20+387+602, 20+387+605, 20+387+609, 20+387+676, 20+387+694, 20+387+698, 20+387+699, 20+387+711, 20+387+754, 20+387+760, 20+387+781, 20+387+786, 20+387+797, 20+387+834, 20+387+835, 20+388+390, 20+388+403, 20+388+408, 20+388+410, 20+388+416, 20+388+448, 20+388+451, 20+388+471, 20+388+472, 20+388+507, 20+388+512, 20+388+515, 20+388+538, 20+388+598, 20+388+602, 20+388+605, 20+388+609, 20+388+676, 20+388+694, 20+388+698, 20+388+699, 20+388+711, 20+388+754, 20+388+760, 20+388+781, 20+388+786, 20+388+797, 20+388+834, 20+388+835, 20+390+403, 20+390+408, 20+390+410, 20+390+416, 20+390+448, 20+390+451, 20+390+471, 20+390+472, 20+390+507, 20+390+512, 20+390+515, 20+390+538, 20+390+598, 20+390+602, 20+390+605, 20+390+609, 20+390+676, 20+390+694, 20+390+698, 20+390+699, 20+390+711, 20+390+754, 20+390+760, 20+390+781, 20+390+786, 20+390+797, 20+390+834, 20+390+835, 20+403+408, 20+403+410, 20+403+416, 20+403+448, 20+403+451, 20+403+471, 20+403+472, 20+403+507, 20+403+512, 20+403+515, 20+403+538, 20+403+598, 20+403+602, 20+403+605, 20+403+609, 20+403+676, 20+403+694, 20+403+698, 20+403+699, 20+403+711, 20+403+754, 20+403+760, 20+403+781, 20+403+786, 20+403+797, 20+403+834, 20+403+835, 20+408+410, 20+408+416, 20+408+448, 20+408+451, 20+408+471, 20+408+472, 20+408+507, 20+408+512, 20+408+515, 20+408+538, 20+408+598, 20+408+602, 20+408+605, 20+408+609, 20+408+676, 20+408+694, 20+408+698, 20+408+699, 20+408+711, 20+408+754, 20+408+760, 20+408+781, 20+408+786, 20+408+797, 20+408+834, 20+408+835, 20+410+416, 20+410+448, 20+410+451, 20+410+471, 20+410+472, 20+410+507, 20+410+512, 20+410+515, 20+410+538, 20+410+598, 20+410+602, 20+410+605, 20+410+609, 20+410+676, 20+410+694, 20+410+698, 20+410+699, 20+410+711, 20+410+754, 20+410+760, 20+410+781, 20+410+786, 20+410+797, 20+410+834, 20+410+835, 20+416+448, 20+416+451, 20+416+471, 20+416+472, 20+416+507, 20+416+512, 20+416+515, 20+416+538, 20+416+598, 20+416+602, 20+416+605, 20+416+609, 20+416+676, 20+416+694, 20+416+698, 20+416+699, 20+416+711, 20+416+754, 20+416+760, 20+416+781, 20+416+786, 20+416+797, 20+416+834, 20+416+835, 20+448+451, 20+448+471, 20+448+472, 20+448+507, 20+448+512, 20+448+515, 20+448+538, 20+448+598, 20+448+602, 20+448+605, 20+448+609, 20+448+676, 20+448+694, 20+448+698, 20+448+699, 20+448+711, 20+448+754, 20+448+760, 20+448+781, 20+448+786, 20+448+797, 20+448+834, 20+448+835, 20+451+471, 20+451+472, 20+451+507, 20+451+512, 20+451+515, 20+451+538, 20+451+598, 20+451+602, 20+451+605, 20+451+609, 20+451+676, 20+451+694, 20+451+698, 20+451+699, 20+451+711, 20+451+754, 20+451+760, 20+451+781, 20+451+786, 20+451+797, 20+451+834, 20+451+835, 20+471+472, 20+471+507, 20+471+512, 20+471+515, 20+471+538, 20+471+598, 20+471+602, 20+471+605, 20+471+609, 20+471+676, 20+471+694, 20+471+698, 20+471+699, 20+471+711, 20+471+754, 20+471+760, 20+471+781, 20+471+786, 20+471+797, 20+471+834, 20+471+835, 20+472+507, 20+472+512, 20+472+515, 20+472+538, 20+472+598, 20+472+602, 20+472+605, 20+472+609, 20+472+676, 20+472+694, 20+472+698, 20+472+699, 20+472+711, 20+472+754, 20+472+760, 20+472+781, 20+472+786, 20+472+797, 20+472+834, 20+472+835, 20+507+512, 20+507+515, 20+507+538, 20+507+598, 20+507+602, 20+507+605, 20+507+609, 20+507+676, 20+507+694, 20+507+698, 20+507+699, 20+507+711, 20+507+754, 20+507+760, 20+507+781, 20+507+786, 20+507+797, 20+507+834, 20+507+835, 20+512+515, 20+512+538, 20+512+598, 20+512+602, 20+512+605, 20+512+609, 20+512+676, 20+512+694, 20+512+698, 20+512+699, 20+512+711, 20+512+754, 20+512+760, 20+512+781, 20+512+786, 20+512+797, 20+512+834, 20+512+835, 20+515+538, 20+515+598, 20+515+602, 20+515+605, 20+515+609, 20+515+676, 20+515+694, 20+515+698, 20+515+699, 20+515+711, 20+515+754, 20+515+760, 20+515+781, 20+515+786, 20+515+797, 20+515+834, 20+515+835, 20+538+598, 20+538+602, 20+538+605, 20+538+609, 20+538+676, 20+538+694, 20+538+698, 20+538+699, 20+538+711, 20+538+754, 20+538+760, 20+538+781, 20+538+786, 20+538+797, 20+538+834, 20+538+835, 20+598+602, 20+598+605,

20+598+609, 20+598+676, 20+598+694, 20+598+698, 20+598+699, 20+598+711, 20+598+754, 20+598+760, 20+598+781, 20+598+786, 20+598+797, 20+598+834, 20+598+835, 20+602+605, 20+602+609, 20+602+676, 20+602+694, 20+602+698, 20+602+699, 20+602+711, 20+602+754, 20+602+760, 20+602+781, 20+602+786, 20+602+797, 20+602+834, 20+602+835, 20+605+609, 20+605+676, 20+605+694, 20+605+698, 20+605+699, 20+605+711, 20+605+754, 20+605+760, 20+605+781, 20+605+786, 20+605+797, 20+605+834, 20+605+835, 20+609+676, 20+609+694, 20+609+698, 20+609+699, 20+609+711, 20+609+754, 20+609+760, 20+609+781, 20+609+786, 20+609+797, 20+609+834, 20+609+835, 20+676+694, 20+676+698, 20+676+699, 20+676+711, 20+676+754, 20+676+760, 20+676+781, 20+676+786, 20+676+797, 20+676+834, 20+676+835, 20+694+698, 20+694+699, 20+694+711, 20+694+754, 20+694+760, 20+694+781, 20+694+786, 20+694+797, 20+694+834, 20+694+835, 20+698+699, 20+698+711, 20+698+754, 20+698+760, 20+698+781, 20+698+786, 20+698+797, 20+698+834, 20+698+835, 20+699+711, 20+699+754, 20+699+760, 20+699+781, 20+699+786, 20+699+797, 20+699+834, 20+699+835, 20+711+754, 20+711+760, 20+711+781, 20+711+786, 20+711+797, 20+711+834, 20+711+835, 20+754+760, 20+754+781, 20+754+786, 20+754+797, 20+754+834, 20+754+835, 20+760+781, 20+760+786, 20+760+797, 20+760+834, 20+760+835, 20+781+786, 20+781+797, 20+781+834, 20+781+835, 20+786+797, 20+786+834, 20+786+835, 20+797+834, 20+797+835, 20+834+835, 51+53+55, 51+53+56, 51+53+60, 51+53+63, 51+53+79 51+53+87, 51+53+192, 51+53+302, 51+53+387, 51+53+388, 51+53+390, 51+53+403, 51+53+408, 51+53+410, 51+53+416, 51+53+448, 51+53+451, 51+53+471, 51+53+472, 51+53+507, 51+53+512, 51+53+515, 51+53+538, 51+53+598, 51+53+602, 51+53+605, 51+53+609, 51+53+676, 51+53+694, 51+53+698, 51+53+699, 51+53+711, 51+53+754, 51+53+760, 51+53+781, 51+53+786, 51+53+797, 51+53+834, 51+53+835, 51+55+56, 51+55+60, 51+55+63, 51+55+79, 51+55+87, 51+55+192, 51+55+302, 51+55+387, 51+55+388, 51+55+390, 51+55+403, 51+55+408, 51+55+410, 51+55+416, 51+55+448, 51+55+451, 51+55+471, 51+55+472, 51+55+507, 51+55+512, 51+55+515, 51+55+538, 51+55+598, 51+55+602, 51+55+605, 51+55+609, 51+55+676, 51+55+694, 51+55+698, 51+55+699, 51+55+711, 51+55+754, 51+55+760, 51+55+781, 51+55+786, 51+55+797, 51+55+834, 51+55+835, 51+56+60, 51+56+63, 51+56+79, 51+56+87, 51+56+192, 51+56+302, 51+56+387, 51+56+388, 51+56+390, 51+56+403, 51+56+408, 51+56+410, 51+56+416, 51+56+448, 51+56+451, 51+56+471, 51+56+472, 51+56+507, 51+56+512, 51+56+515, 51+56+538, 51+56+598, 51+56+602, 51+56+605, 51+56+609, 51+56+676, 51+56+694, 51+56+698, 51+56+699, 51+56+711, 51+56+754, 51+56+760, 51+56+781, 51+56+786, 51+56+797, 51+56+834, 51+56+835, 51+60+63, 51+60+79, 51+60+87, 51+60+192, 51+60+302, 51+60+387, 51+60+388, 51+60+390, 51+60+403, 51+60+408, 51+60+410, 51+60+416, 51+60+448, 51+60+451, 51+60+471, 51+60+472, 51+60+507, 51+60+512, 51+60+515, 51+60+538, 51+60+598, 51+60+602, 51+60+605, 51+60+609, 51+60+676, 51+60+694, 51+60+698, 51+60+699, 51+60+711, 51+60+754, 51+60+760, 51+60+781, 51+60+786, 51+60+797, 51+60+834, 51+60+835, 51+63+79, 51+63+87, 51+63+192, 51+63+302, 51+63+387, 51+63+388, 51+63+390, 51+63+403, 51+63+408, 51+63+410, 51+63+416, 51+63+448, 51+63+451, 51+63+471, 51+63+472, 51+63+507, 51+63+512, 51+63+515, 51+63+538, 51+63+598, 51+63+602, 51+63+605, 51+63+609, 51+63+676, 51+63+694, 51+63+698, 51+63+699, 51+63+711, 51+63+754, 51+63+760, 51+63+781, 51+63+786, 51+63+797, 51+63+834, 51+63+835, 51+79+87, 51+79+192, 51+79+302, 51+79+387, 51+79+388, 51+79+390, 51+79+403, 51+79+408, 51+79+410, 51+79+416, 51+79+448, 51+79+451, 51+79+471, 51+79+472, 51+79+507, 51+79+512, 51+79+515, 51+79+538, 51+79+598, 51+79+602, 51+79+605, 51+79+609, 51+79+676, 51+79+694, 51+79+698, 51+79+699, 51+79+711, 51+79+754, 51+79+760, 51+79+781, 51+79+786, 51+79+797, 51+79+834, 51+79+835, 51+87+192, 51+87+302, 51+87+387, 51+87+388, 51+87+390, 51+87+403, 51+87+408, 51+87+410, 51+87+416, 51+87+448, 51+87+451, 51+87+471, 51+87+472, 51+87+507, 51+87+512, 51+87+515, 51+87+538, 51+87+598, 51+87+602, 51+87+605, 51+87+609, 51+87+676, 51+87+694, 51+87+698, 51+87+699, 51+87+711, 51+87+754, 51+87+760, 51+87+781, 51+87+786, 51+87+797, 51+87+834, 51+87+835, 51+192+302, 51+192+387, 51+192+388, 51+192+390, 51+192+403, 51+192+408, 51+192+410, 51+192+416, 51+192+448, 51+192+451, 51+192+471, 51+192+472, 51+192+507, 51+192+512, 51+192+515, 51+192+538, 51+192+598, 51+192+602, 51+192+605, 51+192+609, 51+192+676, 51+192+694, 51+192+698, 51+192+699, 51+192+711, 51+192+754, 51+192+760, 51+192+781, 51+192+786, 51+192+797, 51+192+834, 51+192+835, 51+302+387, 51+302+388, 51+302+390, 51+302+403, 51+302+408, 51+302+410, 51+302+416, 51+302+448, 51+302+451, 51+302+471, 51+302+472, 51+302+507, 51+302+512, 51+302+515, 51+302+538, 51+302+598, 51+302+602, 51+302+605, 51+302+609, 51+302+676, 51+302+694, 51+302+698, 51+302+699, 51+302+711, 51+302+754, 51+302+760, 51+302+781, 51+302+786, 51+302+797, 51+302+834, 51+302+835, 51+387+388, 51+387+390, 51+387+403, 51+387+408, 51+387+410, 51+387+416, 51+387+448, 51+387+451, 51+387+471, 51+387+472, 51+387+507, 51+387+512, 51+387+515, 51+387+538, 51+387+598, 51+387+602, 51+387+605, 51+387+609, 51+387+676, 51+387+694, 51+387+698, 51+387+699, 51+387+711, 51+387+754, 51+387+760, 51+387+781, 51+387+786, 51+387+797, 51+387+834, 51+387+835, 51+388+390, 51+388+403, 51+388+408, 51+388+410, 51+388+416, 51+388+448, 51+388+451, 51+388+471, 51+388+472, 51+388+507, 51+388+512, 51+388+515, 51+388+538, 51+388+598, 51+388+602, 51+388+605, 51+388+609, 51+388+676, 51+388+694, 51+388+698, 51+388+699, 51+388+711, 51+388+754, 51+388+760, 51+388+781, 51+388+786, 51+388+797, 51+388+834, 51+388+835, 51+390+403, 51+390+408, 51+390+410, 51+390+416, 51+390+448, 51+390+451, 51+390+471, 51+390+472, 51+390+507, 51+390+512, 51+390+515, 51+390+538, 51+390+598, 51+390+602, 51+390+605, 51+390+609, 51+390+676, 51+390+694, 51+390+698, 51+390+699, 51+390+711, 51+390+754, 51+390+760, 51+390+781, 51+390+786, 51+390+797, 51+390+834, 51+390+835, 51+403+408, 51+403+410, 51+403+416, 51+403+448, 51+403+451, 51+403+471, 51+403+472, 51+403+507, 51+403+512, 51+403+515, 51+403+538, 51+403+598, 51+403+602, 51+403+605, 51+403+609, 51+403+676, 51+403+694, 51+403+698, 51+403+699, 51+403+711, 51+403+754, 51+403+760, 51+403+781, 51+403+786, 51+403+797, 51+403+834, 51+403+835, 51+408+410, 51+408+416, 51+408+448, 51+408+451, 51+408+471, 51+408+472, 51+408+507, 51+408+512, 51+408+515, 51+408+538, 51+408+598, 51+408+602, 51+408+605, 51+408+609, 51+408+676, 51+408+694, 51+408+698, 51+408+699, 51+408+711, 51+408+754,

51+408+760, 51+408+781, 51+408+786, 51+408+797,
51+408+834, 51+408+835, 51+410+416, 51+410+448,
51+410+451, 51+410+471, 51+410+472, 51+410+507,
51+410+512, 51+410+515, 51+410+538, 51+410+598,
51+410+602, 51+410+605, 51+410+609, 51+410+676,
51+410+694, 51+410+698, 51+410+699, 51+410+711,
51+410+754, 51+410+760, 51+410+781, 51+410+786,
51+410+797, 51+410+834, 51+410+835, 51+416+448,
51+416+451, 51+416+471, 51+416+472, 51+416+507,
51+416+512, 51+416+515, 51+416+538, 51+416+598,
51+416+602, 51+416+605, 51+416+609, 51+416+676,
51+416+694, 51+416+698, 51+416+699, 51+416+711,
51+416+754, 51+416+760, 51+416+781, 51+416+786,
51+416+797, 51+416+834, 51+416+835, 51+448+451,
51+448+471, 51+448+472, 51+448+507, 51+448+512,
51+448+515, 51+448+538, 51+448+598, 51+448+602,
51+448+605, 51+448+609, 51+448+676, 51+448+694,
51+448+698, 51+448+699, 51+448+711, 51+448+754,
51+448+760, 51+448+781, 51+448+786, 51+448+797,
51+448+834, 51+448+835, 51+451+471, 51+451+472,
51+451+507, 51+451+512, 51+451+515, 51+451+538,
51+451+598, 51+451+602, 51+451+605, 51+451+609,
51+451+676, 51+451+694, 51+451+698, 51+451+699,
51+451+711, 51+451+754, 51+451+760, 51+451+781,
51+451+786, 51+451+797, 51+451+834, 51+451+835,
51+471+472, 51+471+507, 51+471+512, 51+471+515,
51+471+538, 51+471+598, 51+471+602, 51+471+605,
51+471+609, 51+471+676, 51+471+694, 51+471+698,
51+471+699, 51+471+711, 51+471+754, 51+471+760,
51+471+781, 51+471+786, 51+471+797, 51+471+834,
51+471+835, 51+472+507, 51+472+512, 51+472+515,
51+472+538, 51+472+598, 51+472+602, 51+472+605,
51+472+609, 51+472+676, 51+472+694, 51+472+698,
51+472+699, 51+472+711, 51+472+754, 51+472+760,
51+472+781, 51+472+786, 51+472+797, 51+472+834,
51+472+835, 51+507+512, 51+507+515, 51+507+538,
51+507+598, 51+507+602, 51+507+605, 51+507+609,
51+507+676, 51+507+694, 51+507+698, 51+507+699,
51+507+711, 51+507+754, 51+507+760, 51+507+781,
51+507+786, 51+507+797, 51+507+834, 51+507+835,
51+512+515, 51+512+538, 51+512+598, 51+512+602,
51+512+605, 51+512+609, 51+512+676, 51+512+694,
51+512+698, 51+512+699, 51+512+711, 51+512+754,
51+512+760, 51+512+781, 51+512+786, 51+512+797,
51+512+834, 51+512+835, 51+515+538, 51+515+598,
51+515+602, 51+515+605, 51+515+609, 51+515+676,
51+515+694, 51+515+698, 51+515+699, 51+515+711,
51+515+754, 51+515+760, 51+515+781, 51+515+786,
51+515+797, 51+515+834, 51+515+835, 51+538+598,
51+538+602, 51+538+605, 51+538+609, 51+538+676,
51+538+694, 51+538+698, 51+538+699, 51+538+711,
51+538+754, 51+538+760, 51+538+781, 51+538+786,
51+538+797, 51+538+834, 51+538+835, 51+598+602,
51+598+605 51+598+609, 51+598+676, 51+598+694,
51+598+698, 51+598+699, 51+598+711, 51+598+754,
51+598+760, 51+598+781 51+598+786, 51+598+797,
51+598+834, 51+598+835, 51+602+605, 51+602+609,
51+602+676, 51+602+694, 51+602+698, 51+602+699,
51+602+711, 51+602+754, 51+602+760, 51+602+781,
51+602+786, 51+602+797, 51+602+834, 51+602+835,
51+605+609, 51+605+676, 51+605+694, 51+605+698,
51+605+699, 51+605+711, 51+605+754, 51+605+760,
51+605+781, 51+605+786, 51+605+797, 51+605+834,
51+605+835, 51+609+676, 51+609+694, 51+609+698,
51+609+699, 51+609+711, 51+609+754, 51+609+760,
51+609+781, 51+609+786, 51+609+797, 51+609+834,
51+609+835, 51+676+694, 51+676+698, 51+676+699,
51+676+711, 51+676+754, 51+676+760, 51+676+781,
51+676+786, 51+676+797, 51+676+834, 51+676+835,
51+694+698, 51+694+699, 51+694+711, 51+694+754,
51+694+760, 51+694+781, 51+694+786, 51+694+797,
51+694+834, 51+694+835, 51+698+699, 51+698+711,
51+698+754, 51+698+760, 51+698+781, 51+698+786,
51+698+797, 51+698+834, 51+698+835, 51+699+711,
51+699+754, 51+699+760, 51+699+781, 51+699+786,
51+699+797, 51+699+834, 51+699+835, 51+711+754,
51+711+760, 51+711+781, 51+711+786, 51+711+797,
51+711+834, 51+711+835, 51+754+760, 51+754+781,
51+754+786, 51+754+797, 51+754+834, 51+754+835,
51+760+781, 51+760+786, 51+760+797, 51+760+834,
51+760+835, 51+781+786, 51+781+797, 51+781+834,
51+781+835, 51+786+797, 51+786+834, 51+786+835,
51+797+834, 51+797+835, 51+834+835, 53+55+56,
53+55+60, 53+55+63, 53+55+79, 53+55+87, 53+55+192,
53+55+302, 53+55+387, 53+55+388, 53+55+390, 53+55+
403, 53+55+408, 53+55+410, 53+55+416, 53+55+448,
53+55+451, 53+55+471, 53+55+472, 53+55+507, 53+55+
512, 53+55+515, 53+55+538, 53+55+598, 53+55+602,
53+55+605, 53+55+609, 53+55+676, 53+55+694, 53+55+
698, 53+55+699, 53+55+711, 53+55+754, 53+55+760,
53+55+781, 53+55+786, 53+55+797, 53+55+834, 53+55+
835, 53+56+60, 53+56+63, 53+56+79, 53+56+87, 53+56+
192, 53+56+302, 53+56+387, 53+56+388, 53+56+390,
53+56+403, 53+56+408, 53+56+410, 53+56+416, 53+56+
448, 53+56+451, 53+56+471, 53+56+472, 53+56+507,
53+56+512, 53+56+515, 53+56+538, 53+56+598, 53+56+
602, 53+56+605, 53+56+609, 53+56+676, 53+56+694,
53+56+698, 53+56+699, 53+56+711, 53+56+754, 53+56+
760, 53+56+781, 53+56+786, 53+56+797, 53+56+834,
53+56+835, 53+60+63, 53+60+79, 53+60+87, 53+60+192,
53+60+302, 53+60+387, 53+60+388, 53+60+390, 53+60+
403, 53+60+408, 53+60+410, 53+60+416, 53+60+448,
53+60+451, 53+60+471, 53+60+472, 53+60+507, 53+60+
512, 53+60+515, 53+60+538, 53+60+598, 53+60+602,
53+60+605, 53+60+609, 53+60+676, 53+60+694, 53+60+
698, 53+60+699, 53+60+711, 53+60+754, 53+60+760,
53+60+781, 53+60+786, 53+60+797, 53+60+834, 53+60+
835, 53+63+79, 53+63+87, 53+63+192, 53+63+302,
53+63+387, 53+63+388, 53+63+390, 53+63+403, 53+63+
408, 53+63+410, 53+63+416, 53+63+448, 53+63+451,
53+63+471, 53+63+472, 53+63+507, 53+63+512, 53+63+
515, 53+63+538, 53+63+598, 53+63+602, 53+63+605,
53+63+609, 53+63+676, 53+63+694, 53+63+698, 53+63+
699, 53+63+711, 53+63+754, 53+63+760, 53+63+781,
53+63+786, 53+63+797, 53+63+834, 53+63+835, 53+79+
87, 53+79+192, 53+79+302, 53+79+387, 53+79+388,
53+79+390, 53+79+403, 53+79+408, 53+79+410, 53+79+
416, 53+79+448, 53+79+451, 53+79+471, 53+79+472,
53+79+507, 53+79+512, 53+79+515, 53+79+538, 53+79+
598, 53+79+602, 53+79+605, 53+79+609, 53+79+676,
53+79+694, 53+79+698, 53+79+699, 53+79+711, 53+79+
754, 53+79+760, 53+79+781, 53+79+786, 53+79+797,
53+79+834, 53+79+835, 53+87+192, 53+87+302, 53+87+
387, 53+87+388, 53+87+390, 53+87+403, 53+87+408,
53+87+410, 53+87+416, 53+87+448, 53+87+451, 53+87+
471, 53+87+472, 53+87+507, 53+87+512, 53+87+515,
53+87+538, 53+87+598, 53+87+602, 53+87+605, 53+87+
609, 53+87+676, 53+87+694, 53+87+698, 53+87+699,
53+87+711, 53+87+754, 53+87+760, 53+87+781, 53+87+
786, 53+87+797, 53+87+834, 53+87+835, 53+192+302,
53+192+387, 53+192+388, 53+192+390, 53+192+403,
53+192+408, 53+192+410, 53+192+416, 53+192+448,
53+192+451, 53+192+471, 53+192+472, 53+192+507,
53+192+512, 53+192+515, 53+192+538, 53+192+598,

53+192+602, 53+192+605, 53+192+609, 53+192+676, 53+192+694, 53+192+698, 53+192+699, 53+192+711, 53+192+754, 53+192+760, 53+192+781, 53+192+786, 53+192+797, 53+192+834, 53+192+835, 53+302+387, 53+302+388, 53+302+390, 53+302+403, 53+302+408, 53+302+410, 53+302+416, 53+302+448, 53+302+451, 53+302+471, 53+302+472, 53+302+507, 53+302+512, 53+302+515, 53+302+538, 53+302+598, 53+302+602, 53+302+605, 53+302+609, 53+302+676, 53+302+694, 53+302+698, 53+302+699, 53+302+711, 53+302+754, 53+302+760, 53+302+781, 53+302+786, 53+302+797, 53+302+834, 53+302+835, 53+387+388, 53+387+390, 53+387+403, 53+387+408, 53+387+410, 53+387+416, 53+387+448, 53+387+451, 53+387+471, 53+387+472, 53+387+507, 53+387+512, 53+387+515, 53+387+538, 53+387+598, 53+387+602, 53+387+605, 53+387+609, 53+387+676, 53+387+694, 53+387+698, 53+387+699, 53+387+711, 53+387+754, 53+387+760, 53+387+781, 53+387+786, 53+387+797, 53+387+834, 53+387+835, 53+388+390, 53+388+403, 53+388+408, 53+388+410, 53+388+416, 53+388+448, 53+388+451, 53+388+471, 53+388+472, 53+388+507, 53+388+512, 53+388+515, 53+388+538, 53+388+598, 53+388+602, 53+388+605, 53+388+609, 53+388+676, 53+388+694, 53+388+698, 53+388+699, 53+388+711, 53+388+754, 53+388+760, 53+388+781, 53+388+786, 53+388+797, 53+388+834, 53+388+835, 53+390+403, 53+390+408, 53+390+410, 53+390+416, 53+390+448, 53+390+451, 53+390+471, 53+390+472, 53+390+507, 53+390+512, 53+390+515, 53+390+538, 53+390+598, 53+390+602, 53+390+605, 53+390+609, 53+390+676, 53+390+694, 53+390+698, 53+390+699, 53+390+711, 53+390+754, 53+390+760, 53+390+781, 53+390+786, 53+390+797, 53+390+834, 53+390+835, 53+403+408, 53+403+410, 53+403+416, 53+403+448, 53+403+451, 53+403+471, 53+403+472, 53+403+507, 53+403+512, 53+403+515, 53+403+538, 53+403+598, 53+403+602, 53+403+605, 53+403+609, 53+403+676, 53+403+694, 53+403+698, 53+403+699, 53+403+711, 53+403+754, 53+403+760, 53+403+781, 53+403+786, 53+403+797, 53+403+834, 53+403+835, 53+408+410, 53+408+416, 53+408+448, 53+408+451, 53+408+471, 53+408+472, 53+408+507, 53+408+512, 53+408+515, 53+408+538, 53+408+598, 53+408+602, 53+408+605, 53+408+609, 53+408+676, 53+408+694, 53+408+698 53+408+699, 53+408+711, 53+408+754, 53+408+760, 53+408+781, 53+408+786, 53+408+797, 53+408+834, 53+408+835, 53+410+416, 53+410+448, 53+410+451, 53+410+471, 53+410+472, 53+410+507, 53+410+512, 53+410+515, 53+410+538, 53+410+598, 53+410+602, 53+410+605, 53+410+609, 53+410+676, 53+410+694, 53+410+698, 53+410+699, 53+410+711, 53+410+754, 53+410+760, 53+410+781, 53+410+786, 53+410+797, 53+410+834, 53+410+835, 53+416+448, 53+416+451, 53+416+471, 53+416+472, 53+416+507, 53+416+512, 53+416+515, 53+416+538, 53+416+598, 53+416+602, 53+416+605, 53+416+609, 53+416+676, 53+416+694, 53+416+698, 53+416+699, 53+416+711, 53+416+754, 53+416+760, 53+416+781, 53+416+786, 53+416+797, 53+416+834, 53+416+835, 53+448+451, 53+448+471, 53+448+472, 53+448+507, 53+448+512, 53+448+515, 53+448+538, 53+448+598, 53+448+602, 53+448+605, 53+448+609, 53+448+676, 53+448+694, 53+448+698, 53+448+699, 53+448+711, 53+448+754, 53+448+760, 53+448+781, 53+448+786, 53+448+797, 53+448+834, 53+448+835, 53+451+471, 53+451+472, 53+451+507, 53+451+512, 53+451+515, 53+451+538, 53+451+598, 53+451+602, 53+451+605, 53+451+609, 53+451+676, 53+451+694, 53+451+698, 53+451+699, 53+451+711, 53+451+754, 53+451+760, 53+451+781, 53+451+786, 53+451+797, 53+451+834, 53+451+835, 53+471+472, 53+471+507, 53+471+512, 53+471+515, 53+471+538, 53+471+598, 53+471+602, 53+471+605, 53+471+609, 53+471+676, 53+471+694, 53+471+698, 53+471+699, 53+471+711, 53+471+754, 53+471+760, 53+471+781, 53+471+786, 53+471+797, 53+471+834, 53+471+835, 53+472+507, 53+472+512, 53+472+515, 53+472+538, 53+472+598, 53+472+602, 53+472+605, 53+472+609, 53+472+676, 53+472+694, 53+472+698, 53+472+699, 53+472+711, 53+472+754, 53+472+760, 53+472+781, 53+472+786, 53+472+797, 53+472+834, 53+472+835, 53+507+512, 53+507+515, 53+507+538, 53+507+598, 53+507+602, 53+507+605, 53+507+609, 53+507+676, 53+507+694, 53+507+698, 53+507+699, 53+507+711, 53+507+754, 53+507+760, 53+507+781, 53+507+786, 53+507+797, 53+507+834, 53+507+835, 53+512+515, 53+512+538, 53+512+598, 53+512+602, 53+512+605, 53+512+609, 53+512+676, 53+512+694, 53+512+698, 53+512+699, 53+512+711, 53+512+754, 53+512+760, 53+512+781, 53+512+786, 53+512+797, 53+512+834, 53+512+835, 53+515+538, 53+515+598, 53+515+602, 53+515+605, 53+515+609, 53+515+676, 53+515+694, 53+515+698, 53+515+699, 53+515+711, 53+515+754, 53+515+760, 53+515+781, 53+515+786, 53+515+797, 53+515+834, 53+515+835, 53+538+598, 53+538+602, 53+538+605, 53+538+609, 53+538+676, 53+538+694, 53+538+698, 53+538+699, 53+538+711, 53+538+754, 53+538+760, 53+538+781, 53+538+786, 53+538+797, 53+538+834, 53+538+835, 53+598+602, 53+598+605, 53+598+609, 53+598+676, 53+598+694, 53+598+698, 53+598+699, 53+598+711, 53+598+754, 53+598+760, 53+598+781, 53+598+786, 53+598+797, 53+598+834, 53+598+835, 53+602+605, 53+602+609, 53+602+676, 53+602+694, 53+602+698, 53+602+699, 53+602+711, 53+602+754, 53+602+760, 53+602+781, 53+602+786, 53+602+797, 53+602+834, 53+602+835, 53+605+609, 53+605+676, 53+605+694, 53+605+698, 53+605+699, 53+605+711, 53+605+754, 53+605+760, 53+605+781, 53+605+786, 53+605+797, 53+605+834, 53+605+835, 53+609+676, 53+609+694, 53+609+698, 53+609+699, 53+609+711, 53+609+754, 53+609+760, 53+609+781, 53+609+786, 53+609+797, 53+609+834, 53+609+835, 53+676+694, 53+676+698, 53+676+699, 53+676+711, 53+676+754, 53+676+760, 53+676+781, 53+676+786, 53+676+797, 53+676+834, 53+676+835, 53+694+698, 53+694+699, 53+694+711, 53+694+754, 53+694+760, 53+694+781, 53+694+786, 53+694+797, 53+694+834, 53+694+835, 53+698+699, 53+698+711, 53+698+754, 53+698+760, 53+698+781, 53+698+786, 53+698+797, 53+698+834, 53+698+835, 53+699+711, 53+699+754, 53+699+760, 53+699+781, 53+699+786, 53+699+797, 53+699+834, 53+699+835, 53+711+754, 53+711+760, 53+711+781, 53+711+786, 53+711+797, 53+711+834, 53+711+835, 53+754+760, 53+754+781, 53+754+786, 53+754+797, 53+754+834, 53+754+835, 53+760+781, 53+760+786, 53+760+797, 53+760+834, 53+760+835, 53+781+786, 53+781+797, 53+781+834, 53+781+835, 53+786+797, 53+786+834, 53+786+835, 53+797+834, 53+797+835, 53+834+835, 55+56+60, 55+56+63, 55+56+79, 55+56+87, 55+56+192, 55+56+302, 55+56+387, 55+56+388, 55+56+390, 55+56+403, 55+56+408, 55+56+410, 55+56+416, 55+56+448, 55+56+451, 55+56+471, 55+56+472, 55+56+507, 55+56+512, 55+56+515, 55+56+538, 55+56+598, 55+56+602, 55+56+605, 55+56+609, 55+56+676, 55+56+694, 55+56+698, 55+56+

699, 55+56+711, 55+56+754, 55+56+760, 55+56+781, 55+56+786, 55+56+797, 55+56+834, 55+56+835, 55+60+63, 55+60+79, 55+60+87, 55+60+192, 55+60+302, 55+60+387, 55+60+388, 55+60+390, 55+60+403, 55+60+408, 55+60+410, 55+60+416, 55+60+448, 55+60+451, 55+60+471, 55+60+472, 55+60+507, 55+60+512, 55+60+515, 55+60+538, 55+60+598, 55+60+602, 55+60+605, 55+60+609, 5+60+676, 55+60+694, 55+60+698, 55+60+699, 55+60+711, 55+60+754, 55+60+760, 55+60+781, 55+60+786, 55+60+797, 55+60+834, 55+60+835, 55+63+79, 55+63+87, 55+63+192, 55+63+302, 55+63+387, 55+63+388, 55+63+390, 55+63+403, 55+63+408, 55+63+410, 55+63+416, 55+63+448, 55+63+451, 55+63+471, 55+63+472, 55+63+507, 55+63+512, 55+63+515, 55+63+538, 55+63+598, 55+63+602, 55+63+605, 55+63+609, 55+63+676, 55+63+694, 55+63+698, 55+63+699, 55+63+711, 55+63+754, 55+63+760, 55+63+781, 55+63+786, 55+63+797, 55+63+834, 55+63+835, 55+79+87, 55+79+192, 55+79+302, 55+79+387, 55+79+388, 55+79+390, 55+79+403, 55+79+408, 55+79+410, 55+79+416, 55+79+448, 55+79+451, 55+79+471, 55+79+472, 55+79+507, 55+79+512, 55+79+515, 55+79+538, 55+79+598, 55+79+602, 55+79+605, 55+79+609, 55+79+676, 55+79+694, 55+79+698, 55+79+699, 55+79+711, 55+79+754, 55+79+760, 55+79+781, 55+79+786, 55+79+797, 55+79+834, 55+79+835, 55+87+192, 55+87+302, 55+87+387, 55+87+388, 55+87+390, 55+87+403, 55+87+408, 55+87+410, 55+87+416, 55+87+448, 55+87+451, 55+87+471, 55+87+472, 55+87+507, 55+87+512, 55+87+515, 55+87+538, 55+87+598, 55+87+602, 55+87+605, 55+87+609, 55+87+676, 55+87+694, 55+87+698, 55+87+699, 55+87+711, 55+87+754, 55+87+760, 55+87+781, 55+87+786, 55+87+797, 55+87+834, 55+87+835, 55+192+302, 55+192+387, 55+192+388, 55+192+390, 55+192+403, 55+192+408, 55+192+410, 55+192+416, 55+192+448, 55+192+451, 55+192+471, 55+192+472, 55+192+507, 55+192+512, 55+192+515, 55+192+538, 55+192+598, 55+192+602, 55+192+605, 55+192+609, 55+192+676, 55+192+694, 55+192+698, 55+192+699, 55+192+711, 55+192+754, 55+192+760, 55+192+781, 55+192+786, 55+192+797, 55+192+834, 55+192+835, 55+302+387, 55+302+388, 55+302+390, 55+302+403, 55+302+408, 55+302+410, 55+302+416, 55+302+448, 55+302+451, 55+302+471, 55+302+472, 55+302+507, 55+302+512, 55+302+515, 55+302+538, 55+302+598, 55+302+602, 55+302+605, 55+302+609, 55+302+676, 55+302+694, 55+302+698, 55+302+699, 55+302+711, 55+302+754, 55+302+760, 55+302+781, 55+302+786, 55+302+797, 55+302+834, 55+302+835, 55+387+388, 55+387+390, 55+387+403, 55+387+408, 55+387+410, 55+387+416, 55+387+448, 55+387+451, 55+387+471, 55+387+472, 55+387+507, 55+387+512, 55+387+515, 55+387+538, 55+387+598, 55+387+602, 55+387+605, 55+387+609, 55+387+676, 55+387+694, 55+387+698, 55+387+699, 55+387+711, 55+387+754, 55+387+760, 55+387+781, 55+387+786, 55+387+797, 55+387+834, 55+387+835, 55+388+390, 55+388+403, 55+388+408, 55+388+410, 55+388+416, 55+388+448, 55+388+451, 55+388+471, 55+388+472, 55+388+507, 55+388+512, 55+388+515, 55+388+538, 55+388+598, 55+388+602, 55+388+605, 55+388+609, 55+388+676, 55+388+694, 55+388+698, 55+388+699, 55+388+711, 55+388+754, 55+388+760, 55+388+781, 55+388+786, 55+388+797, 55+388+834, 55+388+835, 55+390+403, 55+390+408, 55+390+410, 55+390+416, 55+390+448, 55+390+451, 55+390+471, 55+390+472, 55+390+507, 55+390+512, 55+390+515, 55+390+538, 55+390+598, 55+390+602, 55+390+605, 55+390+609, 55+390+676, 55+390+694, 55+390+698, 55+390+699, 55+390+711, 55+390+754, 55+390+760, 55+390+781, 55+390+786, 55+390+797, 55+390+834, 55+390+835, 55+403+408, 55+403+410, 55+403+416, 55+403+448, 55+403+451, 55+403+471, 55+403+472, 55+403+507, 55+403+512, 55+403+515, 55+403+538, 55+403+598, 55+403+602, 55+403+605, 55+403+609, 55+403+676, 55+403+694, 55+403+698, 55+403+699, 55+403+711, 55+403+754, 55+403+760, 55+403+781, 55+403+786, 55+403+797, 55+403+834, 55+403+835, 55+408+410, 55+408+416, 55+408+448, 55+408+451, 55+408+471, 55+408+472, 55+408+507, 55+408+512, 55+408+515, 55+408+538, 55+408+598, 55+408+602, 55+408+605, 55+408+609, 55+408+676, 55+408+694, 55+408+698, 55+408+699, 55+408+711, 55+408+754, 55+408+760, 55+408+781, 55+408+786, 55+408+797, 55+408+834, 55+408+835, 55+410+416, 55+410+448, 55+410+451, 55+410+471, 55+410+472, 55+410+507, 55+410+512, 55+410+515, 55+410+538, 55+410+598, 55+410+602, 55+410+605, 55+410+609, 55+410+676, 55+410+694, 55+410+698, 55+410+699, 55+410+711, 55+410+754, 55+410+760, 55+410+781, 55+410+786, 55+410+797, 55+410+834, 55+410+835, 55+416+448, 55+416+451, 55+416+471, 55+416+472, 55+416+507, 55+416+512, 55+416+515, 55+416+538, 55+416+598, 55+416+602, 55+416+605, 55+416+609, 55+416+676, 55+416+694, 55+416+698, 55+416+699, 55+416+711, 55+416+754, 55+416+760, 55+416+781, 55+416+786, 55+416+797, 55+416+834, 55+416+835, 55+448+451, 55+448+471, 55+448+472, 55+448+507, 55+448+512, 55+448+515, 55+448+538, 55+448+598, 55+448+602, 55+448+605, 55+448+609, 55+448+676, 55+448+694, 55+448+698, 55+448+699, 55+448+711, 55+448+754, 55+448+760, 55+448+781, 55+448+786, 55+448+797, 55+448+834, 55+448+835, 55+451+471, 55+451+472, 55+451+507, 55+451+512, 55+451+515, 55+451+538, 55+451+598, 55+451+602, 55+451+605, 55+451+609, 55+451+676, 55+451+694, 55+451+698, 55+451+699, 55+451+711, 55+451+754, 55+451+760, 55+451+781, 55+451+786, 55+451+797, 55+451+834, 55+451+835, 55+471+472, 55+471+507, 55+471+512, 55+471+515, 55+471+538, 55+471+598, 55+471+602, 55+471+605, 55+471+609, 55+471+676, 55+471+694, 55+471+698, 55+471+699, 55+471+711, 55+471+754, 55+471+760, 55+471+781, 55+471+786, 55+471+797, 55+471+834, 55+471+835, 55+472+507, 55+472+512, 55+472+515, 55+472+538, 55+472+598, 55+472+602, 55+472+605, 55+472+609, 55+472+676, 55+472+694, 55+472+698, 55+472+699, 55+472+711, 55+472+754, 55+472+760, 55+472+781, 55+472+786, 55+472+797, 55+472+834, 55+472+835, 55+507+512, 55+507+515, 55+507+538, 55+507+598, 55+507+602, 55+507+605, 55+507+609, 55+507+676, 55+507+694, 55+507+698, 55+507+699, 55+507+711, 55+507+754, 55+507+760, 55+507+781, 55+507+786, 55+507+797, 55+507+834, 55+507+835, 55+512+515, 55+512+538, 55+512+598, 55+512+602, 55+512+605, 55+512+609, 55+512+676, 55+512+694, 55+512+698, 55+512+699, 55+512+711, 55+512+754, 55+512+760, 55+512+781, 55+512+786, 55+512+797, 55+512+834, 55+512+835, 55+515+538, 55+515+598, 55+515+602, 55+515+605, 55+515+609, 55+515+676, 55+515+694, 55+515+698, 55+515+699, 55+515+711, 55+515+754, 55+515+760, 55+515+781, 55+515+786, 55+515+797, 55+515+834, 55+515+835, 55+538+598, 55+538+602, 55+538+605, 55+538+609, 55+538+676, 55+538+694, 55+538+698, 55+538+699, 55+538+711, 55+538+754, 55+538+760, 55+538+781, 55+538+786, 55+538+797, 55+538+834,

55+538+835, 55+598+602, 55+598+605, 55+598+609, 55+598+676, 55+598+694, 55+598+698, 55+598+699, 55+598+711, 55+598+754, 55+598+760, 55+598+781, 55+598+786, 55+598+797, 55+598+834, 55+598+835, 55+602+605, 55+602+609, 55+602+676, 55+602+694, 55+602+698, 55+602+699, 55+602+711, 55+602+754, 55+602+760, 55+602+781, 55+602+786, 55+602+797, 55+602+834, 55+602+835, 55+605+609, 55+605+676, 55+605+694, 55+605+698, 55+605+699, 55+605+711, 55+605+754, 55+605+760, 55+605+781, 55+605+786, 55+605+797, 55+605+834, 55+605+835, 55+609+676, 55+609+694, 55+609+698, 55+609+699, 55+609+711, 55+609+754, 55+609+760, 55+609+781, 55+609+786, 55+609+797, 55+609+834, 55+609+835, 55+676+694, 55+676+698, 55+676+699, 55+676+711, 55+676+754, 55+676+760, 55+676+781, 55+676+786, 55+676+797, 55+676+834, 55+676+835, 55+694+698, 55+694+699, 55+694+711, 55+694+754, 55+694+760, 55+694+781, 55+694+786, 55+694+797, 55+694+834, 55+694+835, 55+698+699, 55+698+711, 55+698+754, 55+698+760, 55+698+781, 55+698+786, 55+698+797, 55+698+834, 55+698+835, 55+699+711, 55+699+754, 55+699+760, 55+699+781, 55+699+786, 55+699+797, 55+699+834, 55+699+835, 55+711+754, 55+711+760, 55+711+781, 55+711+786, 55+711+797, 55+711+834, 55+711+835, 55+754+760, 55+754+781, 55+754+786, 55+754+797, 55+754+834, 55+754+835, 55+760+781, 55+760+786, 55+760+797, 55+760+834, 55+760+835, 55+781+786, 55+781+797, 55+781+834, 55+781+835, 55+786+797, 55+786+834, 55+786+835, 55+797+834, 55+797+835, 55+834+835, 56+60+63, 56+60+79, 56+60+87, 56+60+192, 56+60+302, 56+60+387, 56+60+388, 56+60+390, 56+60+403, 56+60+408, 56+60+410, 56+60+416, 56+60+448, 56+60+451, 56+60+471, 56+60+472, 56+60+507, 56+60+512, 56+60+515, 56+60+538, 56+60+598, 56+60+602, 56+60+605, 56+60+609, 56+60+676, 56+60+694, 56+60+698, 56+60+699, 56+60+711, 56+60+754, 56+60+760, 56+60+781, 56+60+786, 56+60+797, 56+60+834, 56+60+835, 56+63+79, 56+63+87, 56+63+192, 56+63+302, 56+63+387, 56+63+388, 56+63+390, 56+63+403, 56+63+408, 56+63+410, 56+63+416, 56+63+448, 56+63+451, 56+63+471, 56+63+472, 56+63+507, 56+63+512, 56+63+515, 56+63+538, 56+63+598, 56+63+602, 56+63+605, 56+63+609, 56+63+676, 56+63+694, 56+63+698, 56+63+699, 56+63+711, 56+63+754, 56+63+760, 56+63+781, 56+63+786, 56+63+797, 56+63+834, 56+63+835, 56+79+87, 56+79+192, 56+79+302, 56+79+387, 56+79+388, 56+79+390, 56+79+403, 56+79+408, 56+79+410, 56+79+416, 56+79+448, 56+79+451, 56+79+471, 56+79+472, 56+79+507, 56+79+512, 56+79+515, 56+79+538, 56+79+598, 56+79+602, 56+79+605, 56+79+609, 56+79+676, 56+79+694, 56+79+698, 56+79+699, 56+79+711, 56+79+754, 56+79+760, 56+79+781, 56+79+786, 56+79+797, 56+79+834, 56+79+835, 56+87+192, 56+87+302, 56+87+387, 56+87+388, 56+87+390, 56+87+403, 56+87+408, 56+87+410, 56+87+416, 56+87+448, 56+87+451, 56+87+471, 56+87+472, 56+87+507, 56+87+512, 56+87+515, 56+87+538, 56+87+598, 56+87+602, 56+87+605, 56+87+609, 56+87+676, 56+87+694, 56+87+698, 56+87+699, 56+87+711, 56+87+754, 56+87+760, 56+87+781, 56+87+786, 56+87+797, 56+87+834, 56+87+835, 56+192+302, 56+192+387, 56+192+388, 56+192+390, 56+192+403, 56+192+408, 56+192+410, 56+192+416, 56+192+448, 56+192+451, 56+192+471, 56+192+472, 56+192+507, 56+192+512, 56+192+515, 56+192+538, 56+192+598, 56+192+602, 56+192+605, 56+192+609, 56+192+676, 56+192+694, 56+192+698, 56+192+699, 56+192+711, 56+192+754, 56+192+760, 56+192+781, 56+192+786, 56+192+797, 56+192+834, 56+192+835, 56+302+387, 56+302+388, 56+302+390, 56+302+403, 56+302+408, 56+302+410, 56+302+416, 56+302+448, 56+302+451, 56+302+471, 56+302+472, 56+302+507, 56+302+512, 56+302+515, 56+302+538, 56+302+598, 56+302+602, 56+302+605, 56+302+609, 56+302+676, 56+302+694, 56+302+698, 56+302+699, 56+302+711, 56+302+754, 56+302+760, 56+302+781, 56+302+786, 56+302+797, 56+302+834, 56+302+835, 56+387+388, 56+387+390, 56+387+403, 56+387+408, 56+387+410, 56+387+416, 56+387+448, 56+387+451, 56+387+471, 56+387+472, 56+387+507, 56+387+512, 56+387+515, 56+387+538, 56+387+598, 56+387+602, 56+387+605, 56+387+609, 56+387+676, 56+387+694, 56+387+698, 56+387+699, 56+387+711, 56+387+754, 56+387+760, 56+387+781, 56+387+786, 56+387+797, 56+387+834, 56+387+835, 56+388+390, 56+388+403, 56+388+408, 56+388+410, 56+388+416, 56+388+448, 56+388+451, 56+388+471, 56+388+472, 56+388+507, 56+388+512, 56+388+515, 56+388+538, 56+388+598, 56+388+602, 56+388+605, 56+388+609, 56+388+676, 56+388+694, 56+388+698, 56+388+699, 56+388+711, 56+388+754, 56+388+760, 56+388+781, 56+388+786, 56+388+797, 56+388+834, 56+388+835, 56+390+403, 56+390+408, 56+390+410, 56+390+416, 56+390+448, 56+390+451, 56+390+471, 56+390+472, 56+390+507, 56+390+512, 56+390+515, 56+390+538, 56+390+598, 56+390+602, 56+390+605, 56+390+609, 56+390+676, 56+390+694, 56+390+698, 56+390+699, 56+390+711, 56+390+754, 56+390+760, 56+390+781, 56+390+786, 56+390+797, 56+390+834, 56+390+835, 56+403+408, 56+403+410, 56+403+416, 56+403+448, 56+403+451, 56+403+471, 56+403+472, 56+403+507, 56+403+512, 56+403+515, 56+403+538, 56+403+598, 56+403+602, 56+403+605, 56+403+609, 56+403+676, 56+403+694, 56+403+698, 56+403+699, 56+403+711, 56+403+754, 56+403+760, 56+403+781, 56+403+786, 56+403+797, 56+403+834, 56+403+835, 56+408+410, 56+408+416, 56+408+448, 56+408+451, 56+408+471, 56+408+472, 56+408+507, 56+408+512, 56+408+515, 56+408+538, 56+408+598, 56+408+602, 56+408+605, 56+408+609, 56+408+676, 56+408+694, 56+408+698, 56+408+699, 56+408+711, 56+408+754, 56+408+760, 56+408+781, 56+408+786, 56+408+797, 56+408+834, 56+408+835, 56+410+416, 56+410+448, 56+410+451, 56+410+471, 56+410+472, 56+410+507, 56+410+512, 56+410+515, 56+410+538, 56+410+598, 56+410+602, 56+410+605, 56+410+609, 56+410+676, 56+410+694, 56+410+698, 56+410+699, 56+410+711, 56+410+754, 56+410+760, 56+410+781, 56+410+786, 56+410+797, 56+410+834, 56+410+835, 56+416+448, 56+416+451, 56+416+471, 56+416+472, 56+416+507, 56+416+512, 56+416+515, 56+416+538, 56+416+598, 56+416+602, 56+416+605, 56+416+609, 56+416+676, 56+416+694, 56+416+698, 56+416+699, 56+416+711, 56+416+754, 56+416+760, 56+416+781, 56+416+786, 56+416+797, 56+416+834, 56+416+835, 56+448+451, 56+448+471, 56+448+472, 56+448+507, 56+448+512, 56+448+515, 56+448+538, 56+448+598, 56+448+602, 56+448+605, 56+448+609, 56+448+676, 56+448+694, 56+448+698, 56+448+699, 56+448+711, 56+448+754, 56+448+760, 56+448+781, 56+448+786, 56+448+797, 56+448+834, 56+448+835, 56+451+471, 56+451+472, 56+451+507, 56+451+512, 56+451+515, 56+451+538, 56+451+598, 56+451+602, 56+451+605, 56+451+609, 56+451+676, 56+451+694, 56+451+698, 56+451+699, 56+451+711, 56+451+754, 56+451+760, 56+451+781,

56+451+786, 56+451+797, 56+451+834, 56+451+835, 56+471+472, 56+471+507, 56+471+512, 56+471+515, 56+471+538, 56+471+598, 56+471+602, 56+471+605, 56+471+609, 56+471+676, 56+471+694, 56+471+698, 56+471+699, 6+471+711, 56+471+754, 56+471+760, 56+471+781, 56+471+786, 56+471+797, 56+471+834, 56+471+835, 56+472+507, 56+472+512, 56+472+515, 56+472+538, 56+472+598, 56+472+602, 56+472+605, 56+472+609, 56+472+676, 56+472+694, 56+472+698, 56+472+699, 56+472+711, 56+472+754, 56+472+760, 56+472+781, 56+472+786, 56+472+797, 56+472+834, 56+472+835, 56+507+512, 56+507+515, 56+507+538, 56+507+598, 56+507+602, 56+507+605, 56+507+609, 56+507+676, 56+507+694, 56+507+698, 56+507+699, 56+507+711, 56+507+754, 56+507+760, 56+507+781, 56+507+786, 56+507+797, 56+507+834, 56+507+835, 56+512+515, 56+512+538, 56+512+598, 56+512+602, 56+512+605, 56+512+609, 56+512+676, 56+512+694, 56+512+698, 56+512+699, 56+512+711, 56+512+754, 56+512+760, 56+512+781, 56+512+786, 56+512+797, 56+512+834, 56+512+835, 56+515+538, 56+515+598, 56+515+602, 56+515+605, 56+515+609, 56+515+676, 56+515+694, 56+515+698, 56+515+699, 56+515+711, 56+515+754, 56+515+760, 56+515+781, 56+515+786, 56+515+797, 56+515+834, 56+515+835, 56+538+598, 56+538+602, 56+538+605, 56+538+609, 56+538+676, 56+538+694, 56+538+698, 56+538+699, 56+538+711, 56+538+754, 56+538+760, 56+538+781, 56+538+786, 56+538+797, 56+538+834, 56+538+835, 56+598+602, 56+598+605, 56+598+609, 56+598+676, 56+598+694, 56+598+698, 56+598+699, 56+598+711, 56+598+754, 56+598+760, 56+598+781, 56+598+786, 56+598+797, 56+598+834, 56+598+835, 56+602+605, 56+602+609, 56+602+676, 56+602+694, 56+602+698, 56+602+699, 56+602+711, 56+602+754, 56+602+760, 56+602+781, 56+602+786, 56+602+797, 56+602+834, 56+602+835, 56+605+609, 56+605+676, 56+605+694, 56+605+698, 56+605+699, 56+605+711, 56+605+754, 56+605+760, 56+605+781, 56+605+786, 56+605+797, 56+605+834, 56+605+835, 56+609+676, 56+609+694, 56+609+698, 56+609+699, 56+609+711, 56+609+754, 56+609+760, 56+609+781, 56+609+786, 56+609+797, 56+609+834, 56+609+835, 56+676+694, 56+676+698, 56+676+699, 56+676+711, 56+676+754, 56+676+760, 56+676+781, 56+676+786, 56+676+797, 56+676+834, 56+676+835, 56+694+698, 56+694+699, 56+694+711, 56+694+754, 56+694+760, 56+694+781, 56+694+786, 56+694+797, 56+694+834, 56+694+835, 56+698+699, 56+698+711, 56+698+754, 56+698+760, 56+698+781, 56+698+786, 56+698+797, 56+698+834, 56+698+835, 56+699+711, 56+699+754, 56+699+760, 56+699+781, 56+699+786, 56+699+797, 56+699+834, 56+699+835, 56+711+754, 56+711+760, 56+711+781, 56+711+786, 56+711+797, 56+711+834, 56+711+835, 56+754+760, 56+754+781, 56+754+786, 56+754+797, 56+754+834, 56+754+835, 56+760+781, 56+760+786, 56+760+797, 56+760+834, 56+760+835, 56+781+786, 56+781+797, 56+781+834, 56+781+835, 56+786+797, 56+786+834, 56+786+835, 56+797+834, 56+797+835, 56+834+835, 60+63+79, 60+63+87, 60+63+192, 60+63+302, 60+63+387, 60+63+388, 60+63+390, 60+63+403, 60+63+408, 60+63+410, 60+63+416, 60+63+448, 60+63+451, 60+63+471, 60+63+472, 60+63+507, 60+63+512, 60+63+515, 60+63+538, 60+63+598, 60+63+602, 60+63+605, 60+63+609, 60+63+676, 60+63+694, 60+63+698, 60+63+699, 60+63+711, 60+63+754, 60+63+760, 60+63+781, 60+63+786, 60+63+797, 60+63+834, 60+63+835, 60+79+87, 60+79+192, 60+79+302, 60+79+387, 60+79+388, 60+79+390, 60+79+403, 60+79+408, 60+79+410, 60+79+416, 60+79+448, 60+79+451, 60+79+471, 60+79+472, 60+79+507, 60+79+512, 60+79+515, 60+79+538, 60+79+598, 60+79+602, 60+79+605, 60+79+609, 60+79+676, 60+79+694, 60+79+698, 60+79+699, 60+79+711, 60+79+754, 60+79+760, 60+79+781, 60+79+786, 60+79+797, 60+79+834, 60+79+835, 60+87+192, 60+87+302, 60+87+387, 60+87+388, 60+87+390, 60+87+403, 60+87+408, 60+87+410, 60+87+416, 60+87+448, 60+87+451, 60+87+471, 60+87+472, 60+87+507, 60+87+512, 60+87+515, 60+87+538, 60+87+598, 60+87+602, 60+87+605, 60+87+609, 60+87+676, 60+87+694, 60+87+698, 60+87+699, 60+87+711, 60+87+754, 60+87+760, 60+87+781, 60+87+786, 60+87+797, 60+87+834, 60+87+835, 60+192+302, 60+192+387, 60+192+388, 60+192+390, 60+192+403, 60+192+408, 60+192+410, 60+192+416, 60+192+448, 60+192+451, 60+192+471, 60+192+472, 60+192+507, 60+192+512, 60+192+515, 60+192+538, 60+192+598, 60+192+602, 60+192+605, 60+192+609, 60+192+676, 60+192+694, 60+192+698, 60+192+699, 60+192+711, 60+192+754, 60+192+760, 60+192+781, 60+192+786, 60+192+797, 60+192+834, 60+192+835, 60+302+387, 60+302+388, 60+302+390, 60+302+403, 60+302+408, 60+302+410, 60+302+416, 60+302+448, 60+302+451, 60+302+471, 60+302+472, 60+302+507, 60+302+512, 60+302+515, 60+302+538, 60+302+598, 60+302+602, 60+302+605, 60+302+609, 60+302+676, 60+302+694, 60+302+698, 60+302+699, 60+302+711, 60+302+754, 60+302+760, 60+302+781, 60+302+786, 60+302+797, 60+302+834, 60+302+835, 60+387+388, 60+387+390, 60+387+403, 60+387+408, 60+387+410, 60+387+416, 60+387+448, 60+387+451, 60+387+471, 60+387+472, 60+387+507, 60+387+512, 60+387+515, 60+387+538, 60+387+598, 60+387+602, 60+387+605, 60+387+609, 60+387+676, 60+387+694, 60+387+698, 60+387+699, 60+387+711, 60+387+754, 60+387+760, 60+387+781, 60+387+786, 60+387+797, 60+387+834, 60+387+835, 60+388+390, 60+388+403, 60+388+408, 60+388+410, 60+388+416, 60+388+448, 60+388+451, 60+388+471, 60+388+472, 60+388+507, 60+388+512, 60+388+515, 60+388+538, 60+388+598, 60+388+602, 60+388+605, 60+388+609, 60+388+676, 60+388+694, 60+388+698, 60+388+699, 60+388+711, 60+388+754, 60+388+760, 60+388+781, 60+388+786, 60+388+797, 60+388+834, 60+388+835, 60+390+403, 60+390+408, 60+390+410, 60+390+416, 60+390+448, 60+390+451, 60+390+471, 60+390+472, 60+390+507, 60+390+512, 60+390+515, 60+390+538, 60+390+598, 60+390+602, 60+390+605, 60+390+609, 60+390+676, 60+390+694, 60+390+698, 60+390+699, 60+390+711, 60+390+754, 60+390+760, 60+390+781, 60+390+786, 60+390+797, 60+390+834, 60+390+835, 60+403+408, 60+403+410, 60+403+416, 60+403+448, 60+403+451, 60+403+471, 60+403+472, 60+403+507, 60+403+512, 60+403+515, 60+403+538, 60+403+598, 60+403+602, 60+403+605, 60+403+609, 60+403+676, 60+403+694, 60+403+698, 60+403+699, 60+403+711, 60+403+754, 60+403+760, 60+403+781, 60+403+786, 60+403+797, 60+403+834, 60+403+835, 60+408+410, 60+408+416, 60+408+448, 60+408+451, 60+408+471, 60+408+472, 60+408+507, 60+408+512, 60+408+515, 60+408+538, 60+408+598, 60+408+602, 60+408+605, 60+408+609, 60+408+676, 60+408+694, 60+408+698, 60+408+699, 60+408+711, 60+408+754, 60+408+760, 60+408+781, 60+408+786, 60+408+797, 60+408+834, 60+408+835, 60+410+416, 60+410+448, 60+410+451, 60+410+471, 60+410+472, 60+410+507, 60+410+512,

60+410+515, 60+410+538, 60+410+598, 60+410+602, 60+410+605, 60+410+609, 60+410+676, 60+410+694, 60+410+698, 60+410+699, 60+410+711, 60+410+754, 60+410+760, 60+410+781, 60+410+786, 60+410+797, 60+410+834, 60+410+835, 60+416+448, 60+416+451, 60+416+471, 60+416+472, 60+416+507, 60+416+512, 60+416+515, 60+416+538, 60+416+598, 60+416+602, 60+416+605, 60+416+609, 60+416+676, 60+416+694, 60+416+698, 60+416+699, 60+416+711, 60+416+754, 60+416+760, 60+416+781, 60+416+786, 60+416+797, 60+416+834, 60+416+835, 60+448+451, 60+448+471, 60+448+472, 60+448+507, 60+448+512, 60+448+515, 60+448+538, 60+448+598, 60+448+602, 60+448+605, 60+448+609, 60+448+676, 60+448+694, 60+448+698, 60+448+699, 60+448+711, 60+448+754, 60+448+760, 60+448+781, 60+448+786, 60+448+797, 60+448+834, 60+448+835, 60+451+471, 60+451+472, 60+451+507, 60+451+512, 60+451+515, 60+451+538, 60+451+598, 60+451+602, 60+451+605, 60+451+609, 60+451+676, 60+451+694, 60+451+698, 60+451+699, 60+451+711, 60+451+754, 60+451+760, 60+451+781, 60+451+786, 60+451+797, 60+451+834, 60+451+835, 60+471+472, 60+471+507, 60+471+512, 60+471+515, 60+471+538, 60+471+598, 60+471+602, 60+471+605, 60+471+609, 60+471+676, 60+471+694, 60+471+698, 60+471+699, 60+471+711, 60+471+754, 60+471+760, 60+471+781, 60+471+786, 60+471+797, 60+471+834, 60+471+835, 60+472+507, 60+472+512, 60+472+515, 60+472+538, 60+472+598, 60+472+602, 60+472+605, 60+472+609, 60+472+676, 60+472+694, 60+472+698, 60+472+699, 60+472+711, 60+472+754, 60+472+760, 60+472+781, 60+472+786, 60+472+797, 60+472+834, 60+472+835, 60+507+512, 60+507+515, 60+507+538, 60+507+598, 60+507+602, 60+507+605, 60+507+609, 60+507+676, 60+507+694, 60+507+698, 60+507+699, 60+507+711, 60+507+754, 60+507+760, 60+507+781, 60+507+786, 60+507+797, 60+507+834, 60+507+835, 60+512+515, 60+512+538, 60+512+598, 60+512+602, 60+512+605, 60+512+609, 60+512+676, 60+512+694, 60+512+698, 60+512+699, 60+512+711, 60+512+754, 60+512+760, 60+512+781, 60+512+786, 60+512+797, 60+512+834, 60+512+835, 60+515+538, 60+515+598, 60+515+602, 60+515+605, 60+515+609, 60+515+676, 60+515+694, 60+515+698, 60+515+699, 60+515+711, 60+515+754, 60+515+760, 60+515+781, 60+515+786, 60+515+797, 60+515+834, 60+515+835, 60+538+598, 60+538+602, 60+538+605, 60+538+609, 60+538+676, 60+538+694, 60+538+698, 60+538+699, 60+538+711, 60+538+754, 60+538+760, 60+538+781, 60+538+786, 60+538+797, 60+538+834, 60+538+835, 60+598+602, 60+598+605, 60+598+609, 60+598+676, 60+598+694, 60+598+698, 60+598+699, 60+598+711, 60+598+754, 60+598+760, 60+598+781, 60+598+786, 60+598+797, 60+598+834, 60+598+835, 60+602+605, 60+602+609, 60+602+676, 60+602+694, 60+602+698, 60+602+699, 60+602+711, 60+602+754, 60+602+760, 60+602+781, 60+602+786, 60+602+797, 60+602+834, 60+602+835, 60+605+609, 60+605+676, 60+605+694, 60+605+698, 60+605+699, 60+605+711, 60+605+754, 60+605+760, 60+605+781, 60+605+786, 60+605+797, 60+605+834, 60+605+835, 60+609+676, 60+609+694, 60+609+698, 60+609+699, 60+609+711, 60+609+754, 60+609+760, 60+609+781, 60+609+786, 60+609+797, 60+609+834, 60+609+835, 60+676+694, 60+676+698, 60+676+699, 60+676+711, 60+676+754, 60+676+760, 60+676+781, 60+676+786, 60+676+797, 60+676+834, 60+676+835, 60+694+698, 60+694+699, 60+694+711, 60+694+754, 60+694+760, 60+694+781, 60+694+786, 60+694+797, 60+694+834, 60+694+835, 60+698+699, 60+698+711, 60+698+754, 60+698+760, 60+698+781, 60+698+786, 60+698+797, 60+698+834, 60+698+835, 60+699+711, 60+699+754, 60+699+760, 60+699+781, 60+699+786, 60+699+797, 60+699+834, 60+699+835, 60+711+754, 60+711+760, 60+711+781, 60+711+786, 60+711+797, 60+711+834, 60+711+835, 60+754+760, 60+754+781, 60+754+786, 60+754+797, 60+754+834, 60+754+835, 60+760+781, 60+760+786, 60+760+797, 60+760+834, 60+760+835, 60+781+786, 60+781+797, 60+781+834, 60+781+835, 60+786+797, 60+786+834, 60+786+835, 60+797+834, 60+797+835, 60+834+835, 63+79+87, 63+79+192, 63+79+302, 63+79+387, 63+79+388, 63+79+390, 63+79+403, 63+79+408, 63+79+410, 63+79+416, 63+79+448, 63+79+451, 63+79+471, 63+79+472, 63+79+507, 63+79+512, 63+79+515, 63+79+538, 63+79+598, 63+79+602, 63+79+605, 63+79+609, 63+79+676, 63+79+694, 63+79+698, 63+79+699, 63+79+711, 63+79+754, 63+79+760, 63+79+781, 63+79+786, 63+79+797, 63+79+834, 63+79+835, 63+87+192, 63+87+302, 63+87+387, 63+87+388, 63+87+390, 63+87+403, 63+87+408, 63+87+410, 63+87+416, 63+87+448, 63+87+451, 63+87+471, 63+87+472, 63+87+507, 63+87+512, 63+87+515, 63+87+538, 63+87+598, 63+87+602, 63+87+605, 63+87+609, 63+87+676, 63+87+694, 63+87+698, 63+87+699, 63+87+711, 63+87+754, 63+87+760, 63+87+781, 63+87+786, 63+87+797, 63+87+834, 63+87+835, 63+192+302, 63+192+387, 63+192+388, 63+192+390, 63+192+403, 63+192+408, 63+192+410, 63+192+416, 63+192+448, 63+192+451, 63+192+471, 63+192+472, 63+192+507, 63+192+512, 63+192+515, 63+192+538, 63+192+598, 63+192+602, 63+192+605, 63+192+609, 63+192+676, 63+192+694, 63+192+698, 63+192+699, 63+192+711, 63+192+754, 63+192+760, 63+192+781, 63+192+786, 63+192+797, 63+192+834, 63+192+835, 63+302+387, 63+302+388, 63+302+390, 63+302+403, 63+302+408, 63+302+410, 63+302+416, 63+302+448, 63+302+451, 63+302+471, 63+302+472, 63+302+507, 63+302+512, 63+302+515, 63+302+538, 63+302+598, 63+302+602, 63+302+605 63+302+609, 63+302+676, 63+302+694, 63+302+698, 63+302+699, 63+302+711, 63+302+754, 63+302+760, 63+302+781, 63+302+786, 63+302+797, 63+302+834, 63+302+835, 63+387+388, 63+387+390, 63+387+403, 63+387+408, 63+387+410, 63+387+416, 63+387+448, 63+387+451, 63+387+471, 63+387+472, 63+387+507, 63+387+512, 63+387+515, 63+387+538, 63+387+598, 63+387+602, 63+387+605, 63+387+609, 63+387+676, 63+387+694, 63+387+698, 63+387+699, 63+387+711, 63+387+754, 63+387+760, 63+387+781, 63+387+786, 63+387+797, 63+387+834, 63+387+835, 63+388+390, 63+388+403, 63+388+408, 63+388+410, 63+388+416, 63+388+448, 63+388+451, 63+388+471, 63+388+472, 63+388+507, 63+388+512, 63+388+515, 63+388+538, 63+388+598, 63+388+602, 63+388+605, 63+388+609, 63+388+676, 63+388+694, 63+388+698, 63+388+699, 63+388+711, 63+388+754, 63+388+760, 63+388+781, 63+388+786, 63+388+797, 63+388+834, 63+388+835, 63+390+403, 63+390+408, 63+390+410, 63+390+416, 63+390+448, 63+390+451, 63+390+471, 63+390+472, 63+390+507, 63+390+512, 63+390+515, 63+390+538, 63+390+598, 63+390+602, 63+390+605, 63+390+609, 63+390+676, 63+390+694, 63+390+698, 63+390+699, 63+390+711, 63+390+754, 63+390+760, 63+390+781, 63+390+786, 63+390+797, 63+390+834, 63+390+835, 63+403+408, 63+403+410, 63+403+416, 63+403+448, 63+403+451, 63+403+471, 63+403+472, 63+403+507, 63+403+512,

63+403+515, 63+403+538, 63+403+598, 63+403+602, 63+403+605, 63+403+609, 63+403+676, 63+403+694, 63+403+698, 63+403+699, 63+403+711, 63+403+754, 63+403+760, 63+403+781, 63+403+786, 63+403+797, 63+403+834, 63+403+835, 63+408+410, 63+408+416, 63+408+448, 63+408+451, 63+408+471, 63+408+472, 63+408+507, 63+408+512, 63+408+515, 63+408+538, 63+408+598, 63+408+602, 63+408+605, 63+408+609, 63+408+676, 63+408+694, 63+408+698, 63+408+699, 63+408+711, 63+408+754, 63+408+760, 63+408+781, 63+408+786, 63+408+797, 63+408+834, 63+408+835, 63+410+416, 63+410+448, 63+410+451, 63+410+471, 63+410+472, 63+410+507, 63+410+512, 63+410+515, 63+410+538, 63+410+598, 63+410+602, 63+410+605, 63+410+609, 63+410+676, 63+410+694, 63+410+698, 63+410+699, 63+410+711, 63+410+754, 63+410+760, 63+410+781, 63+410+786, 63+410+797, 63+410+834, 63+410+835, 63+416+448, 63+416+451, 63+416+471, 63+416+472, 63+416+507, 63+416+512, 63+416+515, 63+416+538, 63+416+598, 63+416+602, 63+416+605, 63+416+609, 63+416+676, 63+416+694, 63+416+698, 63+416+699, 63+416+711, 63+416+754, 63+416+760, 63+416+781, 63+416+786, 63+416+797, 63+416+834, 63+416+835, 63+448+451, 63+448+471, 63+448+472, 63+448+507, 63+448+512, 63+448+515, 63+448+538, 63+448+598, 63+448+602, 63+448+605, 63+448+609, 63+448+676, 63+448+694, 63+448+698, 63+448+699, 63+448+711, 63+448+754, 63+448+760, 63+448+781, 63+448+786, 63+448+797, 63+448+834, 63+448+835, 63+451+471, 63+451+472, 63+451+507, 63+451+512, 63+451+515, 63+451+538, 63+451+598, 63+451+602, 63+451+605, 63+451+609, 63+451+676, 63+451+694, 63+451+698, 63+451+699, 63+451+711, 63+451+754, 63+451+760, 63+451+781, 63+451+786, 63+451+797, 63+451+834, 63+451+835, 63+471+472, 63+471+507, 63+471+512, 63+471+515, 63+471+538, 63+471+598, 63+471+602, 63+471+605, 63+471+609, 63+471+676, 63+471+694, 63+471+698, 63+471+699, 63+471+711, 63+471+754, 63+471+760, 63+471+781, 63+471+786, 63+471+797, 63+471+834, 63+471+835, 63+472+507, 63+472+512, 63+472+515, 63+472+538, 63+472+598, 63+472+602, 63+472+605, 63+472+609, 63+472+676, 63+472+694, 63+472+698, 63+472+699, 63+472+711, 63+472+754, 63+472+760, 63+472+781, 63+472+786, 63+472+797, 63+472+834, 63+472+835, 63+507+512, 63+507+515, 63+507+538, 63+507+598, 63+507+602, 63+507+605, 63+507+609, 63+507+676, 63+507+694, 63+507+698, 63+507+699, 63+507+711, 63+507+754, 63+507+760, 63+507+781, 63+507+786, 63+507+797, 63+507+834, 63+507+835, 63+512+515, 63+512+538, 63+512+598, 63+512+602, 63+512+605, 63+512+609, 63+512+676, 63+512+694, 63+512+698, 63+512+699, 63+512+711, 63+512+754, 63+512+760, 63+512+781, 63+512+786, 63+512+797, 63+512+834, 63+512+835, 63+515+538, 63+515+598, 63+515+602, 63+515+605, 63+515+609, 63+515+676, 63+515+694, 63+515+698, 63+515+699, 63+515+711, 63+515+754, 63+515+760, 63+515+781, 63+515+786, 63+515+797, 63+515+834, 63+515+835, 63+538+598, 63+538+602, 63+538+605, 63+538+609, 63+538+676, 63+538+694, 63+538+698, 63+538+699, 63+538+711, 63+538+754, 63+538+760, 63+538+781, 63+538+786, 63+538+797, 63+538+834, 63+538+835, 63+598+602, 63+598+605, 63+598+609, 63+598+676, 63+598+694, 63+598+698, 63+598+699, 63+598+711, 63+598+754, 63+598+760, 63+598+781, 63+598+786, 63+598+797, 63+598+834, 63+598+835, 63+602+605, 63+602+609, 63+602+676, 63+602+694, 63+602+698, 63+602+699, 63+602+711, 63+602+754, 63+602+760, 63+602+781, 63+602+786, 63+602+797, 63+602+834, 63+602+835, 63+605+609, 63+605+676, 63+605+694, 63+605+698, 63+605+699, 63+605+711, 63+605+754, 63+605+760, 63+605+781, 63+605+786, 63+605+797, 63+605+834, 63+605+835, 63+609+676, 63+609+694, 63+609+698, 63+609+699, 63+609+711, 63+609+754, 63+609+760, 63+609+781, 63+609+786, 63+609+797, 63+609+834, 63+609+835, 63+676+694, 63+676+698, 63+676+699, 63+676+711, 63+676+754, 63+676+760, 63+676+781, 63+676+786, 63+676+797, 63+676+834, 63+676+835, 63+694+698, 63+694+699, 63+694+711, 63+694+754, 63+694+760, 63+694+781, 63+694+786, 63+694+797, 63+694+834, 63+694+835, 63+698+699, 63+698+711, 63+698+754, 63+698+760, 63+698+781, 63+698+786, 63+698+797, 63+698+834, 63+698+835, 63+699+711, 63+699+754, 63+699+760, 63+699+781, 63+699+786, 63+699+797, 63+699+834, 63+699+835, 63+711+754, 63+711+760, 63+711+781, 63+711+786, 63+711+797, 63+711+834, 63+711+835, 63+754+760, 63+754+781, 63+754+786, 63+754+797, 63+754+834, 63+754+835, 63+760+781, 63+760+786, 63+760+797, 63+760+834, 63+760+835, 63+781+786, 63+781+797, 63+781+834, 63+781+835, 63+786+797, 63+786+834, 63+786+835, 63+797+834, 63+797+835, 63+834+835, 79+87+192, 79+87+302, 79+87+387, 79+87+388, 79+87+390, 79+87+403, 79+87+408, 79+87+410, 79+87+416, 79+87+448, 79+87+451, 79+87+471, 79+87+472, 79+87+507, 79+87+512, 79+87+515, 79+87+538, 79+87+598, 79+87+602, 79+87+605, 79+87+609, 79+87+676, 79+87+694, 79+87+698, 79+87+699, 79+87+711, 79+87+754, 79+87+760, 79+87+781, 79+87+786, 79+87+797, 79+87+834, 79+87+835, 79+192+302, 79+192+387, 79+192+388, 79+192+390, 79+192+403, 79+192+408, 79+192+410, 79+192+416, 79+192+448, 79+192+451, 79+192+471, 79+192+472, 79+192+507, 79+192+512, 79+192+515, 79+192+538, 79+192+598, 79+192+602, 79+192+605, 79+192+609, 79+192+676, 79+192+694, 79+192+698, 79+192+699, 79+192+711, 79+192+754, 79+192+760, 79+192+781, 79+192+786, 79+192+797, 79+192+834, 79+192+835, 79+302+387, 79+302+388, 79+302+390, 79+302+403, 79+302+408, 79+302+410, 79+302+416, 79+302+448, 79+302+451, 79+302+471, 79+302+472, 79+302+507, 79+302+512, 79+302+515, 79+302+538, 79+302+598, 79+302+602, 79+302+605, 79+302+609, 79+302+676, 79+302+694, 79+302+698, 79+302+699, 79+302+711, 79+302+754, 79+302+760, 79+302+781, 79+302+786, 79+302+797, 79+302+834, 79+302+835, 79+387+388, 79+387+390, 79+387+403, 79+387+408, 79+387+410, 79+387+416, 79+387+448, 79+387+451, 79+387+471, 79+387+472, 79+387+507, 79+387+512, 79+387+515, 79+387+538, 79+387+598, 79+387+602, 79+387+605, 79+387+609, 79+387+676, 79+387+694, 79+387+698, 79+387+699, 79+387+711, 79+387+754, 79+387+760, 79+387+781, 79+387+786, 79+387+797, 79+387+834, 79+387+835, 79+388+390, 79+388+403, 79+388+408, 79+388+410, 79+388+416, 79+388+448, 79+388+451, 79+388+471, 79+388+472, 79+388+507, 79+388+512, 79+388+515, 79+388+538, 79+388+598, 79+388+602, 79+388+605, 79+388+609, 79+388+676, 79+388+694, 79+388+698, 79+388+699, 79+388+711, 79+388+754, 79+388+760, 79+388+781, 79+388+786, 79+388+797, 79+388+834, 79+388+835, 79+390+403, 79+390+408, 79+390+410, 79+390+416, 79+390+448, 79+390+451, 79+390+471, 79+390+472, 79+390+507, 79+390+512, 79+390+515, 79+390+538, 79+390+598, 79+390+602, 79+390+605, 79+390+609, 79+390+676,

79+390+694, 79+390+698, 79+390+699, 79+390+711, 79+390+754, 79+390+760, 79+390+781, 79+390+786, 79+390+797, 79+390+834, 79+390+835, 79+403+408, 79+403+410, 79+403+416, 79+403+448, 79+403+451, 79+403+471, 79+403+472, 79+403+507, 79+403+512, 79+403+515, 79+403+538, 79+403+598, 79+403+602, 79+403+605, 79+403+609, 79+403+676, 79+403+694, 79+403+698, 79+403+699, 79+403+711, 79+403+754, 79+403+760, 79+403+781, 79+403+786, 79+403+797, 79+403+834, 79+403+835, 79+408+410, 79+408+416, 79+408+448, 79+408+451, 79+408+471, 79+408+472, 79+408+507, 79+408+512, 79+408+515, 79+408+538, 79+408+598, 79+408+602, 79+408+605, 79+408+609, 79+408+676, 79+408+694, 79+408+698, 79+408+699, 79+408+711, 79+408+754, 79+408+760, 79+408+781, 79+408+786, 79+408+797, 79+408+834, 79+408+835, 79+410+416, 79+410+448, 79+410+451, 79+410+471, 79+410+472, 79+410+507, 79+410+512, 79+410+515, 79+410+538, 79+410+598, 79+410+602, 79+410+605, 79+410+609, 79+410+676, 79+410+694, 79+410+698, 79+410+699, 79+410+711, 79+410+754, 79+410+760, 79+410+781, 79+410+786, 79+410+797, 79+410+834, 79+410+835, 9+416+448, 79+416+451, 79+416+471, 79+416+472, 79+416+507, 79+416+512, 79+416+515, 79+416+538, 79+416+598, 79+416+602, 79+416+605, 79+416+609, 79+416+676, 79+416+694, 79+416+698, 79+416+699, 79+416+711, 79+416+754, 79+416+760, 79+416+781, 79+416+786, 79+416+797, 79+416+834, 79+416+835, 79+448+451, 79+448+471, 79+448+472, 79+448+507, 79+448+512, 79+448+515, 79+448+538, 79+448+598, 79+448+602, 79+448+605, 79+448+609, 79+448+676, 79+448+694, 79+448+698, 79+448+699, 79+448+711, 79+448+754, 79+448+760, 79+448+781, 79+448+786, 79+448+797, 79+448+834, 79+448+835, 79+451+471, 79+451+472, 79+451+507, 79+451+512, 79+451+515, 79+451+538, 79+451+598, 79+451+602, 79+451+605, 79+451+609, 79+451+676, 79+451+694, 79+451+698, 79+451+699, 79+451+711, 79+451+754, 79+451+760, 79+451+781, 79+451+786, 79+451+797, 79+451+834, 79+451+835, 79+471+472, 79+471+507, 79+471+512, 79+471+515, 79+471+538, 79+471+598, 79+471+602, 79+471+605, 79+471+609, 79+471+676, 79+471+694, 79+471+698, 79+471+699, 79+471+711, 79+471+754, 79+471+760, 79+471+781, 79+471+786, 79+471+797, 79+471+834, 79+471+835, 79+472+507, 79+472+512, 79+472+515, 79+472+538, 79+472+598, 79+472+602, 79+472+605, 79+472+609, 79+472+676, 79+472+694, 79+472+698, 79+472+699, 79+472+711, 79+472+754, 79+472+760, 79+472+781, 79+472+786, 79+472+797, 79+472+834, 79+472+835, 79+507+512, 79+507+515, 79+507+538, 79+507+598, 79+507+602, 79+507+605, 79+507+609, 79+507+676, 79+507+694, 79+507+698, 79+507+699, 79+507+711, 79+507+754, 79+507+760, 79+507+781, 79+507+786, 79+507+797, 79+507+834, 79+507+835, 79+512+515, 79+512+538, 79+512+598, 79+512+602, 79+512+605, 79+512+609, 79+512+676, 79+512+694, 79+512+698, 79+512+699, 79+512+711, 79+512+754, 79+512+760, 79+512+781, 79+512+786, 79+512+797, 79+512+834, 79+512+835, 79+515+538, 79+515+598, 79+515+602, 79+515+605, 79+515+609, 79+515+676, 79+515+694, 79+515+698, 79+515+699, 79+515+711, 79+515+754, 79+515+760, 79+515+781, 79+515+786, 79+515+797, 79+515+834, 79+515+835, 79+538+598, 79+538+602, 79+538+605, 79+538+609, 79+538+676, 79+538+694, 79+538+698, 79+538+699, 79+538+711, 79+538+754, 79+538+760, 79+538+781, 79+538+786, 79+538+797, 79+538+834, 79+538+835, 79+598+602, 79+598+605, 79+598+609, 79+598+676, 79+598+694, 79+598+698, 79+598+699, 79+598+711, 79+598+754, 79+598+760, 79+598+781, 79+598+786, 79+598+797, 79+598+834, 79+598+835, 79+602+605, 79+602+609, 79+602+676, 79+602+694, 79+602+698, 79+602+699, 79+602+711, 79+602+754, 79+602+760, 79+602+781, 79+602+786, 79+602+797, 79+602+834, 79+602+835, 79+605+609, 79+605+676, 79+605+694, 79+605+698, 79+605+699, 79+605+711, 79+605+754, 79+605+760, 79+605+781, 79+605+786, 79+605+797, 79+605+834, 79+605+835, 79+609+676, 79+609+694, 79+609+698, 79+609+699, 9+609+711, 79+609+754, 79+609+760, 79+609+781, 79+609+786, 79+609+797, 79+609+834, 79+609+835, 79+676+694, 79+676+698, 79+676+699, 79+676+711, 79+676+754, 79+676+760, 79+676+781, 79+676+786, 79+676+797, 79+676+834, 79+676+835, 79+694+698, 79+694+699, 79+694+711, 79+694+754, 79+694+760, 79+694+781, 79+694+786, 79+694+797, 79+694+834, 79+694+835, 79+698+699, 79+698+711, 79+698+754, 79+698+760, 79+698+781, 79+698+786, 79+698+797, 79+698+834, 79+698+835, 79+699+711, 79+699+754, 79+699+760, 79+699+781, 79+699+786, 79+699+797, 79+699+834, 79+699+835, 79+711+754, 79+711+760, 79+711+781, 79+711+786, 79+711+797, 79+711+834, 79+711+835, 79+754+760, 79+754+781, 79+754+786, 79+754+797, 79+754+834, 79+754+835, 79+760+781, 79+760+786, 79+760+797, 79+760+834, 79+760+835, 79+781+786, 79+781+797, 79+781+834, 79+781+835, 79+786+797, 79+786+834, 79+786+835, 79+797+834, 79+797+835, 79+834+835, 87+192+302, 87+192+387, 87+192+388, 87+192+390, 87+192+403, 87+192+408, 87+192+410, 87+192+416, 87+192+448, 87+192+451, 87+192+471, 87+192+472, 87+192+507, 87+192+512, 87+192+515, 87+192+538, 87+192+598, 87+192+602, 87+192+605, 87+192+609, 87+192+676, 87+192+694, 87+192+698, 87+192+699, 87+192+711, 87+192+754, 87+192+760, 87+192+781, 87+192+786, 87+192+797, 87+192+834, 87+192+835, 87+302+387, 87+302+388, 87+302+390, 87+302+403, 87+302+408, 87+302+410, 87+302+416, 87+302+448, 87+302+451, 87+302+471, 87+302+472, 87+302+507, 87+302+512, 87+302+515, 87+302+538, 87+302+598, 87+302+602, 87+302+605, 87+302+609, 87+302+676, 87+302+694, 87+302+698, 87+302+699, 87+302+711, 87+302+754, 87+302+760, 87+302+781, 87+302+786, 87+302+797, 87+302+834, 87+302+835, 87+387+388, 87+387+390, 87+387+403, 87+387+408, 87+387+410, 87+387+416, 87+387+448, 87+387+451, 87+387+471, 87+387+472, 87+387+507, 87+387+512, 87+387+515, 87+387+538, 87+387+598, 87+387+602, 87+387+605, 87+387+609, 87+387+676, 87+387+694, 87+387+698, 87+387+699, 87+387+711, 87+387+754, 87+387+760, 87+387+781, 87+387+786, 87+387+797, 87+387+834, 87+387+835, 87+388+390, 87+388+403, 87+388+408, 87+388+410, 87+388+416, 87+388+448, 87+388+451, 87+388+471, 87+388+472, 87+388+507, 87+388+512, 87+388+515, 87+388+538, 87+388+598, 87+388+602, 87+388+605, 87+388+609, 87+388+676, 87+388+694, 87+388+698, 87+388+699, 87+388+711, 87+388+754, 87+388+760, 87+388+781, 87+388+786, 87+388+797, 87+388+834, 87+388+835, 87+390+403, 87+390+408, 87+390+410, 87+390+416, 87+390+448, 87+390+451, 87+390+471, 87+390+472, 87+390+507, 87+390+512, 87+390+515, 87+390+538, 87+390+598, 87+390+602, 87+390+605, 87+390+609, 87+390+676, 87+390+694, 87+390+698, 87+390+699, 87+390+711, 87+390+754, 87+390+760, 87+390+781, 87+390+786,

87+390+797, 87+390+834, 87+390+835, 87+403+408, 87+403+410, 87+403+416, 87+403+448, 87+403+451, 87+403+471, 87+403+472, 87+403+507, 87+403+512, 87+403+515, 87+403+538, 87+403+598, 87+403+602, 87+403+605, 87+403+609, 87+403+676, 87+403+694, 87+403+698, 87+403+699, 87+403+711, 87+403+754, 87+403+760, 87+403+781, 87+403+786, 87+403+797, 87+403+834, 87+403+835, 87+408+410, 87+408+416, 87+408+448, 87+408+451, 87+408+471, 87+408+472, 87+408+507, 87+408+512, 87+408+515, 87+408+538, 87+408+598, 87+408+602, 87+408+605, 87+408+609, 87+408+676, 87+408+694, 87+408+698, 87+408+699, 87+408+711, 87+408+754, 87+408+760, 87+408+781, 87+408+786, 87+408+797, 87+408+834, 87+408+835, 87+410+416, 87+410+448, 87+410+451, 87+410+471, 87+410+472, 87+410+507, 87+410+512, 87+410+515, 87+410+538, 87+410+598, 87+410+602, 87+410+605, 87+410+609, 87+410+676, 87+410+694, 87+410+698, 87+410+699, 87+410+711, 87+410+754, 87+410+760, 87+410+781, 87+410+786, 87+410+797, 87+410+834, 87+410+835, 87+416+448, 87+416+451, 87+416+471, 87+416+472, 87+416+507, 87+416+512, 87+416+515, 87+416+538, 87+416+598, 87+416+602, 87+416+605, 87+416+609, 87+416+676, 87+416+694, 87+416+698, 87+416+699, 87+416+711, 87+416+754, 87+416+760, 87+416+781, 87+416+786, 87+416+797, 87+416+834, 87+416+835, 87+448+451, 87+448+471, 87+448+472, 87+448+507, 87+448+512, 87+448+515, 87+448+538, 87+448+598, 87+448+602, 87+448+605, 87+448+609, 87+448+676, 87+448+694, 87+448+698, 87+448+699, 87+448+711, 87+448+754, 87+448+760, 87+448+781, 87+448+786, 87+448+797, 87+448+834, 87+448+835, 87+451+471, 87+451+472, 87+451+507, 87+451+512, 87+451+515, 87+451+538, 87+451+598, 87+451+602, 87+451+605, 87+451+609, 87+451+676, 87+451+694, 87+451+698, 87+451+699, 87+451+711, 87+451+754, 87+451+760, 87+451+781, 87+451+786, 87+451+797, 87+451+834, 87+451+835, 87+471+472, 87+471+507, 87+471+512, 87+471+515, 87+471+538, 87+471+598, 87+471+602, 87+471+605, 87+471+609, 87+471+676, 87+471+694, 87+471+698, 87+471+699, 87+471+711, 87+471+754, 87+471+760, 87+471+781, 87+471+786, 87+471+797, 87+471+834, 87+471+835, 87+472+507, 87+472+512, 87+472+515, 87+472+538, 87+472+598, 87+472+602, 87+472+605, 87+472+609, 87+472+676, 87+472+694, 87+472+698, 87+472+699, 87+472+711, 87+472+754, 87+472+760, 87+472+781, 87+472+786, 87+472+797, 87+472+834, 87+472+835, 87+507+512, 87+507+515, 87+507+538, 87+507+598, 87+507+602, 87+507+605, 87+507+609, 87+507+676, 87+507+694, 87+507+698, 87+507+699, 87+507+711, 87+507+754, 87+507+760, 87+507+781, 87+507+786, 87+507+797, 87+507+834, 87+507+835, 87+512+515, 87+512+538, 87+512+598, 87+512+602, 87+512+605, 87+512+609, 87+512+676, 87+512+694, 87+512+698, 87+512+699, 87+512+711, 87+512+754, 87+512+760, 87+512+781, 87+512+786, 87+512+797, 87+512+834, 87+512+835, 87+515+538, 87+515+598, 87+515+602, 87+515+605, 87+515+609, 87+515+676, 87+515+694, 87+515+698, 87+515+699, 87+515+711, 87+515+754, 87+515+760, 87+515+781, 87+515+786, 87+515+797, 87+515+834, 87+515+835, 87+538+598, 87+538+602, 87+538+605, 87+538+609, 87+538+676, 87+538+694, 87+538+698, 87+538+699, 87+538+711, 87+538+754, 87+538+760, 87+538+781, 87+538+786, 87+538+797, 87+538+834, 87+538+835, 87+598+602, 87+598+605, 87+598+609, 87+598+676, 87+598+694, 87+598+698, 87+598+699, 87+598+711, 87+598+754, 87+598+760, 87+598+781, 87+598+786, 87+598+797, 87+598+834, 87+598+835, 87+602+605, 87+602+609, 87+602+676, 87+602+694, 87+602+698, 87+602+699, 87+602+711, 87+602+754, 87+602+760, 87+602+781, 87+602+786, 87+602+797, 87+602+834, 87+602+835, 87+605+609, 87+605+676, 87+605+694, 87+605+698, 87+605+699, 87+605+711, 87+605+754, 87+605+760, 87+605+781, 87+605+786, 87+605+797, 87+605+834, 87+605+835, 87+609+676, 87+609+694, 87+609+698, 87+609+699, 87+609+711, 87+609+754, 87+609+760, 87+609+781, 87+609+786, 87+609+797, 87+609+834, 87+609+835, 87+676+694, 87+676+698, 87+676+699, 87+676+711, 87+676+754, 87+676+760, 87+676+781, 87+676+786, 87+676+797, 87+676+834, 87+676+835, 87+694+698, 87+694+699, 87+694+711, 87+694+754, 87+694+760, 87+694+781, 87+694+786, 87+694+797, 87+694+834, 87+694+835, 87+698+699, 87+698+711, 87+698+754, 87+698+760, 87+698+781, 87+698+786, 87+698+797, 87+698+834, 87+698+835, 87+699+711, 87+699+754, 87+699+760, 87+699+781, 87+699+786, 87+699+797, 87+699+834, 87+699+835, 87+711+754, 87+711+760, 87+711+781, 87+711+786, 87+711+797, 87+711+834, 87+711+835, 87+754+760, 87+754+781, 87+754+786, 87+754+797, 87+754+834, 87+754+835, 87+760+781, 87+760+786, 87+760+797, 87+760+834, 87+760+835, 87+781+786, 87+781+797, 87+781+834, 87+781+835, 87+786+797, 87+786+834, 87+786+835, 87+797+834, 87+797+835, 87+834+835, 192+302+387, 192+302+388, 192+302+390, 192+302+403, 192+302+408, 192+302+410, 192+302+416, 192+302+448, 192+302+451, 192+302+471, 192+302+472, 192+302+507, 192+302+512, 192+302+515, 192+302+538, 192+302+598, 192+302+602, 192+302+605, 192+302+609, 192+302+676, 192+302+694, 192+302+698, 192+302+699, 192+302+711, 192+302+754, 192+302+760, 192+302+781, 192+302+786, 192+302+797, 192+302+834, 192+302+835, 192+387+388, 192+387+390, 192+387+403, 192+387+408, 192+387+410, 192+387+416, 192+387+448, 192+387+451, 192+387+471, 192+387+472, 192+387+507, 192+387+512, 192+387+515, 192+387+538, 192+387+598, 192+387+602, 192+387+605, 192+387+609, 192+387+676, 192+387+694, 192+387+698, 192+387+699, 192+387+711, 192+387+754, 192+387+760, 192+387+781, 192+387+786, 192+387+797, 192+387+834, 192+387+835, 192+388+390, 192+388+403, 192+388+408, 192+388+410, 192+388+416, 192+388+448, 192+388+451, 192+388+471, 192+388+472, 192+388+507, 192+388+512, 192+388+515, 192+388+538, 192+388+598, 192+388+602, 192+388+605, 192+388+609, 192+388+676, 192+388+694, 192+388+698, 192+388+699, 192+388+711, 192+388+754, 192+388+760, 192+388+781, 192+388+786, 192+388+797, 192+388+834, 192+388+835, 192+390+403, 192+390+408, 192+390+410, 192+390+416, 192+390+448, 192+390+451, 192+390+471, 192+390+472, 192+390+507, 192+390+512, 192+390+515, 192+390+538, 192+390+598, 192+390+602, 192+390+605, 192+390+609, 192+390+676, 192+390+694, 192+390+698, 192+390+699, 192+390+711, 192+390+754, 192+390+760, 192+390+781, 192+390+786, 192+390+797, 192+390+834, 192+390+835, 192+403+408, 192+403+410, 192+403+416, 192+403+448, 192+403+451, 192+403+471, 192+403+472, 192+403+507, 192+403+512, 192+403+515, 192+403+538, 192+403+598, 192+403+602, 192+403+605, 192+403+609, 192+403+676, 192+403+694, 192+403+698, 192+403+699, 192+403+711, 192+403+754, 192+403+760, 192+403+781, 192+403+786, 192+403+797, 192+403+834, 192+403+835, 192+408+410, 192+408+416, 192+408+448, 192+408+451, 192+408+471, 192+408+472, 192+408+507, 192+408+512, 192+408+515, 192+408+538,

192+408+598, 192+408+602, 192+408+605, 192+408+609, 192+408+676, 192+408+694, 192+408+698, 192+408+699, 192+408+711, 192+408+754, 192+408+760, 192+408+781, 192+408+786, 192+408+797, 192+408+834, 192+408+835, 192+410+416, 192+410+448, 192+410+451, 192+410+471, 192+410+472, 192+410+507, 192+410+512, 192+410+515, 192+410+538, 192+410+598, 192+410+602, 192+410+605, 192+410+609, 192+410+676, 192+410+694, 192+410+698, 192+410+699, 192+410+711, 192+410+754, 192+410+760, 192+410+781, 192+410+786, 192+410+797, 192+410+834, 192+410+835, 192+416+448, 192+416+451, 192+416+471, 192+416+472, 192+416+507, 192+416+512, 192+416+515, 192+416+538, 192+416+598, 192+416+602, 192+416+605, 192+416+609, 192+416+676, 192+416+694, 192+416+698, 192+416+699, 192+416+711, 192+416+754, 192+416+760, 192+416+781, 192+416+786, 192+416+797, 192+416+834, 192+416+835, 192+448+451, 192+448+471, 192+448+472, 192+448+507, 192+448+512, 192+448+515, 192+448+538, 192+448+598, 192+448+602, 192+448+605, 192+448+609, 192+448+676, 192+448+694, 192+448+698, 192+448+699, 192+448+711, 192+448+754, 192+448+760, 192+448+781, 192+448+786, 192+448+797, 192+448+834, 192+448+835, 192+451+471, 192+451+472, 192+451+507, 192+451+512, 192+451+515, 192+451+538, 192+451+598, 192+451+602, 192+451+605, 192+451+609, 192+451+676, 192+451+694, 192+451+698, 192+451+699, 192+451+711, 192+451+754, 192+451+760, 192+451+781, 192+451+786, 192+451+797, 192+451+834, 192+451+835, 192+471+472, 192+471+507, 192+471+512, 192+471+515, 192+471+538, 192+471+598, 192+471+602, 192+471+605, 192+471+609, 192+471+676, 192+471+694, 192+471+698, 192+471+699, 192+471+711, 192+471+754, 192+471+760, 192+471+781, 192+471+786, 192+471+797, 192+471+834, 192+471+835, 192+472+507, 192+472+512, 192+472+515, 192+472+538, 192+472+598, 192+472+602, 192+472+605, 192+472+609, 192+472+676, 192+472+694, 192+472+698, 192+472+699, 192+472+711, 192+472+754, 192+472+760, 192+472+781, 192+472+786, 192+472+797, 192+472+834, 192+472+835, 192+507+512, 192+507+515, 192+507+538, 192+507+598, 192+507+602, 192+507+605, 192+507+609, 192+507+676, 192+507+694, 192+507+698, 192+507+699, 192+507+711, 192+507+754, 192+507+760, 192+507+781, 192+507+786, 192+507+797, 192+507+834, 192+507+835, 192+512+515, 192+512+538, 192+512+598, 192+512+602, 192+512+605, 192+512+609, 192+512+676, 192+512+694, 192+512+698, 192+512+699, 192+512+711, 192+512+754, 192+512+760, 192+512+781, 192+512+786, 192+512+797, 192+512+834, 192+512+835, 192+515+538, 192+515+598 192+515+602, 192+515+605, 192+515+609, 192+515+676, 192+515+694, 192+515+698, 192+515+699, 192+515+711, 192+515+754, 192+515+760, 192+515+781, 192+515+786, 192+515+797, 192+515+834, 192+515+835, 192+538+598, 192+538+602, 192+538+605, 192+538+609, 192+538+676, 192+538+694, 192+538+698, 192+538+699, 192+538+711, 192+538+754, 192+538+760, 192+538+781, 192+538+786, 192+538+797, 192+538+834, 192+538+835, 192+598+602, 192+598+605, 192+598+609, 192+598+676, 192+598+694, 192+598+698, 192+598+699, 192+598+711, 192+598+754, 192+598+760, 192+598+781, 192+598+786, 192+598+797, 192+598+834, 192+598+835, 192+602+605, 192+602+609, 192+602+676, 192+602+694, 192+602+698, 192+602+699, 192+602+711, 192+602+754, 192+602+760, 192+602+781, 192+602+786, 192+602+797, 192+602+834, 192+602+835, 192+605+609, 192+605+676, 192+605+694, 192+605+698, 192+605+699, 192+605+711, 192+605+754, 192+605+760, 192+605+781, 192+605+786, 192+605+797, 192+605+834, 192+605+835, 192+609+676, 192+609+694, 192+609+698, 192+609+699, 192+609+711, 192+609+754, 192+609+760, 192+609+781, 192+609+786, 192+609+797, 192+609+834, 192+609+835, 192+676+694, 192+676+698, 192+676+699, 192+676+711, 192+676+754, 192+676+760, 192+676+781, 192+676+786, 192+676+797, 192+676+834, 192+676+835, 192+694+698, 192+694+699, 192+694+711, 192+694+754, 192+694+760, 192+694+781, 192+694+786, 192+694+797, 192+694+834, 192+694+835, 192+698+699, 192+698+711, 192+698+754, 192+698+760, 192+698+781, 192+698+786, 192+698+797, 192+698+834, 192+698+835, 192+699+711, 192+699+754, 192+699+760, 192+699+781, 192+699+786, 192+699+797, 192+699+834, 192+699+835, 192+711+754, 192+711+760, 192+711+781, 192+711+786, 192+711+797, 192+711+834, 192+711+835, 192+754+760, 192+754+781, 192+754+786, 192+754+797, 192+754+834, 192+754+835, 192+760+781, 192+760+786, 192+760+797, 192+760+834, 192+760+835, 192+781+786, 192+781+797, 192+781+834, 192+781+835, 192+786+797, 192+786+834, 192+786+835, 192+797+834, 192+797+835, 192+834+835, 302+387+388, 302+387+390, 302+387+403, 302+387+408, 302+387+410, 302+387+416, 302+387+448, 302+387+451, 302+387+471, 302+387+472, 302+387+507, 302+387+512, 302+387+515, 302+387+538, 302+387+598, 302+387+602, 302+387+605, 302+387+609, 302+387+676, 302+387+694, 302+387+698, 302+387+699, 302+387+711, 302+387+754, 302+387+760, 302+387+781, 302+387+786, 302+387+797, 302+387+834, 302+387+835, 302+388+390, 302+388+403, 302+388+408, 302+388+410, 302+388+416, 302+388+448, 302+388+451, 302+388+471, 302+388+472, 302+388+507, 302+388+512, 302+388+515, 302+388+538, 302+388+598, 302+388+602, 302+388+605, 302+388+609, 302+388+676, 302+388+694, 302+388+698, 302+388+699, 302+388+711, 302+388+754, 302+388+760, 302+388+781, 302+388+786, 302+388+797, 302+388+834, 302+388+835, 302+390+403, 302+390+408, 302+390+410, 302+390+416, 302+390+448, 302+390+451, 302+390+471, 302+390+472, 302+390+507, 302+390+512, 302+390+515, 302+390+538, 302+390+598, 302+390+602, 302+390+605, 302+390+609, 302+390+676, 302+390+694, 302+390+698, 302+390+699, 302+390+711, 302+390+754, 302+390+760, 302+390+781, 302+390+786, 302+390+797, 302+390+834, 302+390+835, 302+403+408, 302+403+410, 302+403+416, 302+403+448, 302+403+451, 302+403+471, 302+403+472, 302+403+507, 302+403+512, 302+403+515, 302+403+538, 302+403+598, 302+403+602, 302+403+605, 302+403+609, 302+403+676, 302+403+694, 302+403+698, 302+403+699, 302+403+711, 302+403+754, 302+403+760, 302+403+781, 302+403+786, 302+403+797, 302+403+834, 302+403+835, 302+408+410, 302+408+416, 302+408+448, 302+408+451, 302+408+471, 302+408+472, 302+408+507, 302+408+512, 302+408+515, 302+408+538, 302+408+598, 302+408+602, 302+408+605, 302+408+609, 302+408+676, 302+408+694, 302+408+698, 302+408+699, 302+408+711, 302+408+754, 302+408+760, 302+408+781, 302+408+786, 302+408+797, 302+408+834, 302+408+835, 302+410+416, 302+410+448, 302+410+451, 302+410+471, 302+410+472, 302+410+507, 302+410+512, 302+410+515, 302+410+538, 302+410+598, 302+410+602, 302+410+605, 302+410+609, 302+410+676, 302+410+694, 302+410+698, 302+410+699, 302+410+711, 302+410+754, 302+410+760, 302+410+781, 302+410+786, 302+410+797, 302+410+834, 302+410+835, 302+416+448, 302+416+451, 302+416+471, 302+416+472, 302+416+507, 302+416+512, 302+416+515, 302+416+538, 302+416+598, 302+416+602, 302+416+605, 302+416+609, 302+416+676, 302+416+694, 302+416+698, 302+416+699, 302+416+711, 302+416+754, 302+416+760, 302+416+781, 302+416+786, 302+416+797, 302+416+834, 302+416+835, 302+448+451, 302+448+471, 302+448+472, 302+448+507, 302+448+512, 302+448+515,

302+448+538, 302+448+598, 302+448+602, 302+448+605,
302+448+609, 302+448+676, 302+448+694, 302+448+698,
302+448+699, 302+448+711, 302+448+754, 302+448+760,
302+448+781, 302+448+786, 302+448+797, 302+448+834,
302+448+835, 302+451+471, 302+451+472, 302+451+507,
302+451+512, 302+451+515, 302+451+538, 302+451+598,
302+451+602, 302+451+605, 302+451+609, 302+451+676,
302+451+694, 302+451+698, 302+451+699, 302+451+711,
302+451+754, 302+451+760, 302+451+781, 302+451+786,
302+451+797, 302+451+834, 302+451+835 302+471+472,
302+471+507, 302+471+512, 302+471+515, 302+471+538,
302+471+598, 302+471+602, 302+471+605, 302+471+609,
302+471+676, 302+471+694, 302+471+698, 302+471+699,
302+471+711, 302+471+754, 302+471+760, 302+471+781,
302+471+786, 302+471+797, 302+471+834, 302+471+835,
302+472+507, 302+472+512, 302+472+515, 302+472+538,
302+472+598, 302+472+602, 302+472+605, 302+472+609,
302+472+676, 302+472+694, 302+472+698, 302+472+699,
302+472+711, 302+472+754, 302+472+760, 302+472+781,
302+472+786, 302+472+797, 302+472+834, 302+472+835,
302+507+512, 302+507+515, 302+507+538, 302+507+598,
302+507+602, 302+507+605, 302+507+609, 302+507+676,
302+507+694, 302+507+698, 302+507+699, 302+507+711,
302+507+754, 302+507+760, 302+507+781, 302+507+786,
302+507+797, 302+507+834, 302+507+835, 302+512+515,
302+512+538, 302+512+598, 302+512+602, 302+512+605,
302+512+609, 302+512+676, 302+512+694, 302+512+698,
302+512+699, 302+512+711, 302+512+754, 302+512+760,
302+512+781, 302+512+786, 302+512+797, 302+512+834,
302+512+835, 302+515+538, 302+515+598, 302+515+602,
302+515+605, 302+515+609, 302+515+676, 302+515+694,
302+515+698, 302+515+699, 302+515+711, 302+515+754,
302+515+760, 302+515+781, 302+515+786, 302+515+797,
302+515+834, 302+515+835, 302+538+598, 302+538+602,
302+538+605, 302+538+609, 302+538+676, 302+538+694,
302+538+698, 302+538+699, 302+538+711, 302+538+754,
302+538+760, 302+538+781, 302+538+786, 302+538+797,
302+538+834, 302+538+835, 302+598+602, 302+598+605,
302+598+609, 302+598+676, 302+598+694, 302+598+698,
302+598+699, 302+598+711, 302+598+754, 302+598+760,
302+598+781, 302+598+786, 302+598+797, 302+598+834,
302+598+835, 302+602+605, 302+602+609, 302+602+676,
302+602+694, 302+602+698, 302+602+699, 302+602+711,
302+602+754, 302+602+760, 302+602+781, 302+602+786,
302+602+797, 302+602+834, 302+602+835, 302+605+609,
302+605+676, 202+605+694, 302+605+698, 302+605+699,
302+605+711, 302+605+754, 302+605+760, 302+605+781,
302+605+786, 302+605+797, 302+605+834, 302+605+835,
302+609+676, 302+609+694, 302+609+698, 302+609+699,
302+609+711, 302+609+754, 302+609+760, 302+609+781,
302+609+786, 302+609+797, 302+609+834, 302+609+835,
302+676+694, 302+676+698, 302+676+699, 302+676+711,
302+676+754, 302+676+760, 302+676+781, 302+676+786,
302+676+797, 302+676+834, 302+676+835, 302+694+698,
302+694+699, 302+694+711, 302+694+754, 302+694+760,
302+694+781, 302+694+786, 302+694+797, 302+694+834,
302+694+835, 302+698+699, 302+698+711, 302+698+754,
302+698+760, 302+698+781, 302+698+786, 302+698+797,
302+698+834, 302+698+835, 302+699+711, 302+699+754,
302+699+760, 302+699+781, 302+699+786, 302+699+797,
302+699+834, 302+699+835, 302+711+754, 302+711+760,
302+711+781, 302+711+786, 302+711+797, 302+711+834,
302+711+835, 302+754+760, 302+754+781, 302+754+786,
302+754+797, 302+754+834, 302+754+835, 302+760+781,
302+760+786, 302+760+797, 302+760+834, 302+760+835,
302+781+786, 302+781+797, 302+781+834, 302+781+835,
302+786+797, 302+786+834, 302+786+835, 302+797+834,
302+797+835, 302+834+835, 387+388+390, 387+388+403,
387+388+408, 387+388+410, 387+388+416, 387+388+448,
387+388+451, 387+388+471, 387+388+472, 387+388+507,
387+388+512, 387+388+515, 387+388+538, 387+388+598,
387+388+602, 387+388+605, 387+388+609, 387+388+676,
387+388+694, 387+388+698, 387+388+699, 387+388+711,
387+388+754, 387+388+760, 387+388+781, 387+388+786,
387+388+797, 387+388+834, 387+388+835, 387+390+403,
387+390+408, 387+390+410, 387+390+416, 387+390+448,
387+390+451, 387+390+471, 387+390+472, 387+390+507,
387+390+512, 387+390+515, 387+390+538, 387+390+598,
387+390+602, 387+390+605, 387+390+609, 387+390+676,
387+390+694, 387+390+698, 387+390+699, 387+390+711,
387+390+754, 87+390+760, 387+390+781, 387+390+786,
387+390+797, 387+390+834, 387+390+835, 387+403+408,
387+403+410, 387+403+416, 387+403+448, 387+403+451,
387+403+471, 387+403+472, 387+403+507, 387+403+512,
387+403+515, 387+403+538, 387+403+598, 387+403+602,
387+403+605, 387+403+609, 387+403+676, 387+403+694,
387+403+698, 387+403+699, 387+403+711, 387+403+754,
387+403+760, 387+403+781, 387+403+786, 387+403+797,
387+403+834, 387+403+835, 387+408+410, 387+408+416,
387+408+448, 387+408+451, 387+408+471, 387+408+472,
387+408+507, 387+408+512, 387+408+515, 387+408+538,
387+408+598, 387+408+602, 387+408+605, 387+408+609,
387+408+676, 387+408+694, 387+408+698, 387+408+699,
387+408+711, 387+408+754, 387+408+760, 387+408+781,
387+408+786, 387+408+797, 387+408+834, 387+408+835,
387+410+416, 387+410+448, 387+410+451, 387+410+471,
87+410+472, 387+410+507, 387+410+512, 387+410+515,
387+410+538, 387+410+598, 387+410+602, 387+410+605,
387+410+609, 387+410+676, 387+410+694, 387+410+698,
387+410+699, 387+410+711, 387+410+754, 387+410+760,
387+410+781, 387+410+786, 387+410+797, 387+410+834,
387+410+835, 387+416+448, 387+416+451, 387+416+471,
387+416+472, 387+416+507, 387+416+512, 387+416+515,
387+416+538, 387+416+598, 387+416+602, 387+416+605,
387+416+609, 387+416+676, 387+416+694, 387+416+698,
387+416+699, 387+416+711, 387+416+754, 387+416+760,
387+416+781, 387+416+786, 387+416+797, 387+416+834,
387+416+835, 387+448+451, 387+448+471, 387+448+472,
387+448+507, 387+448+512, 387+448+515, 387+448+538,
387+448+598, 387+448+602, 387+448+605, 387+448+609,
387+448+676, 387+448+694, 387+448+698, 387+448+699,
387+448+711, 387+448+754, 387+448+760, 387+448+781,
387+448+786, 387+448+797, 387+448+834, 387+448+835,
387+451+471, 387+451+472, 387+451+507, 387+451+512,
387+451+515, 387+451+538, 387+451+598, 387+451+602,
387+451+605, 387+451+609, 387+451+676, 387+451+694,
387+451+698, 387+451+699, 387+451+711, 387+451+754,
387+451+760, 387+451+781, 387+451+786, 387+451+797,
387+451+834, 387+451+835, 387+471+472, 387+471+507,
387+471+512, 387+471+515, 387+471+538, 387+471+598,
387+471+602, 387+471+605, 387+471+609, 387+471+676,
387+471+694, 387+471+698, 387+471+699, 387+471+711,
387+471+754, 387+471+760, 387+471+781, 387+471+786,
387+471+797, 387+471+834, 387+471+835, 387+472+507,
387+472+512, 387+472+515, 387+472+538, 387+472+598,
387+472+602, 387+472+605, 387+472+609, 387+472+676,
387+472+694, 387+472+698, 387+472+699, 387+472+711,
387+472+754, 387+472+760, 387+472+781, 387+472+786,
387+472+797, 387+472+834, 387+472+835, 387+507+512,
387+507+515, 387+507+538, 387+507+598, 387+507+602,
387+507+605, 387+507+609, 387+507+676, 387+507+694,
387+507+698, 387+507+699, 387+507+711, 387+507+754,
387+507+760, 387+507+781, 387+507+786, 387+507+797,
387+507+834, 387+507+835, 387+512+515, 387+512+538,

387+512+598, 387+512+602, 387+512+605, 387+512+609,
387+512+676, 387+512+694, 387+512+698, 387+512+699,
387+512+711, 387+512+754, 387+512+760, 387+512+781,
387+512+786, 387+512+797, 387+512+834, 387+512+835,
387+515+538, 387+515+598, 387+515+602, 387+515+605,
387+515+609, 387+515+676, 387+515+694, 387+515+698,
387+515+699, 387+515+711, 387+515+754, 387+515+760,
387+515+781, 387+515+786, 387+515+797, 387+515+834,
387+515+835, 387+538+598, 387+538+602, 387+538+605,
387+538+609, 387+538+676, 387+538+694, 387+538+698,
387+538+699, 387+538+711, 387+538+754, 387+538+760,
387+538+781, 387+538+786, 387+538+797, 387+538+834,
387+538+835, 387+598+602, 387+598+605, 387+598+609,
387+598+676, 387+598+694, 387+598+698, 387+598+699,
387+598+711, 387+598+754, 387+598+760, 387+598+781,
387+598+786, 387+598+797, 387+598+834, 387+598+835,
387+602+605, 387+602+609, 387+602+676, 387+602+694,
387+602+698, 387+602+699, 387+602+711, 387+602+754,
387+602+760, 387+602+781, 387+602+786, 387+602+797,
387+602+834, 387+602+835, 387+605+609, 387+605+676,
387+605+694, 387+605+698, 387+605+699, 387+605+711,
387+605+754, 387+605+760, 387+605+781, 387+605+786,
387+605+797, 387+605+834, 387+605+835, 387+609+676,
387+609+694, 387+609+698, 387+609+699, 387+609+711,
387+609+754, 387+609+760, 387+609+781, 387+609+786,
387+609+797, 387+609+834, 387+609+835, 387+676+694,
387+676+698, 387+676+699, 387+676+711, 387+676+754,
387+676+760, 387+676+781, 387+676+786, 387+676+797,
387+676+834, 387+676+835, 387+694+698, 387+694+699,
387+694+711, 387+694+754, 387+694+760, 387+694+781,
387+694+786, 387+694+797, 387+694+834, 387+694+835,
387+698+699, 387+698+711, 387+698+754, 387+698+760,
387+698+781, 387+698+786, 387+698+797, 387+698+834,
387+698+835, 387+699+711, 387+699+754, 387+699+760,
387+699+781, 387+699+786, 387+699+797, 387+699+834,
387+699+835, 387+711+754, 387+711+760, 387+711+781,
387+711+786, 387+711+797, 387+711+834, 387+711+835,
387+754+760, 387+754+781, 387+754+786, 387+754+797,
387+754+834, 387+754+835, 387+760+781, 387+760+786,
387+760+797, 387+760+834, 387+760+835, 387+781+786,
387+781+797, 387+781+834, 387+781+835, 387+786+797,
387+786+834, 387+786+835, 387+797+834, 387+797+835,
387+834+835, 388+390+403, 388+390+408, 388+390+410,
388+390+416, 388+390+448, 388+390+451, 388+390+471,
388+390+472, 388+390+507, 388+390+512, 388+390+515,
388+390+538, 388+390+598, 388+390+602, 388+390+605,
388+390+609, 388+390+676, 388+390+694, 388+390+698,
388+390+699, 388+390+711, 388+390+754, 388+390+760,
388+390+781, 388+390+786, 388+390+797, 388+390+834,
388+390+835, 388+403+408, 388+403+410, 388+403+416,
388+403+448, 388+403+451, 388+403+471, 388+403+472,
388+403+507, 388+403+512, 388+403+515, 388+403+538,
388+403+598, 388+403+602, 388+403+605, 388+403+609,
388+403+676, 388+403+694, 388+403+698, 388+403+699,
388+403+711, 388+403+754, 388+403+760, 388+403+781,
388+403+786, 388+403+797, 388+403+834, 388+403+835,
388+408+410, 388+408+416, 388+408+448, 388+408+451,
388+408+471, 388+408+472, 388+408+507, 388+408+512,
388+408+515, 388+408+538, 388+408+598, 388+408+602,
388+408+605, 388+408+609, 388+408+676, 388+408+694,
388+408+698, 388+408+699, 388+408+711, 388+408+754,
388+408+760, 388+408+781, 388+408+786, 388+408+797,
388+408+834, 388+408+835, 388+410+416, 388+410+448,
388+410+451, 388+410+471, 388+410+472, 388+410+507,
388+410+512, 388+410+515, 388+410+538, 388+410+598,
388+410+602, 388+410+605, 388+410+609, 388+410+676,
388+410+694, 388+410+698, 388+410+699, 388+410+711,
388+410+754, 388+410+760, 388+410+781, 388+410+786,
388+410+797, 388+410+834, 388+410+835, 388+416+448,
388+416+451, 388+416+471, 388+416+472, 388+416+507,
388+416+512, 388+416+515, 388+416+538, 388+416+598,
388+416+602, 388+416+605, 388+416+609, 388+416+676,
388+416+694, 388+416+698, 388+416+699, 388+416+711,
388+416+754, 388+416+760, 388+416+781, 388+416+786,
388+416+797, 388+416+834, 388+416+835, 388+448+451,
388+448+471, 388+448+472, 388+448+507, 388+448+512,
388+448+515, 388+448+538, 388+448+598, 388+448+602,
388+448+605, 388+448+609, 388+448+676, 388+448+694,
388+448+698, 388+448+699, 388+448+711, 388+448+754,
388+448+760, 388+448+781, 388+448+786, 388+448+797,
388+448+834, 388+448+835, 388+451+471, 388+451+472,
388+451+507, 388+451+512, 388+451+515, 388+451+538,
388+451+598, 388+451+602, 388+451+605, 388+451+609,
388+451+676, 388+451+694, 388+451+698, 388+451+699,
388+451+711, 388+451+754, 388+451+760, 388+451+781,
388+451+786, 388+451+797, 388+451+834, 388+451+835,
388+471+472, 388+471+507, 388+471+512, 388+471+515,
388+471+538, 388+471+598, 388+471+602, 388+471+605,
388+471+609, 388+471+676, 388+471+694, 388+471+698,
388+471+699, 388+471+711, 388+471+754, 388+471+760,
388+471+781, 388+471+786, 388+471+797, 388+471+834,
388+471+835, 388+472+507, 388+472+512, 388+472+515,
388+472+538, 388+472+598, 388+472+602, 388+472+605,
388+472+609, 388+472+676, 388+472+694, 388+472+698,
388+472+699, 388+472+711, 388+472+754, 388+472+760,
388+472+781, 388+472+786, 388+472+797, 388+472+834,
388+472+835, 388+507+512, 388+507+515, 388+507+538,
388+507+598, 388+507+602, 388+507+605, 388+507+609,
388+507+676, 388+507+694, 388+507+698, 388+507+699,
388+507+711, 388+507+754, 388+507+760, 388+507+781,
388+507+786, 388+507+797, 388+507+834, 388+507+835,
388+512+515, 388+512+538, 388+512+598, 388+512+602,
388+512+605, 388+512+609, 388+512+676, 388+512+694,
388+512+698, 388+512+699, 388+512+711, 388+512+754,
388+512+760, 388+512+781, 388+512+786, 388+512+797,
388+512+834, 388+512+835, 388+515+538, 388+515+598,
388+515+602, 388+515+605, 388+515+609, 388+515+676,
388+515+694, 388+515+698, 388+515+699, 388+515+711,
388+515+754, 388+515+760, 388+515+781, 388+515+786,
388+515+797, 388+515+834, 388+515+835, 388+538+598,
388+538+602, 388+538+605, 388+538+609, 388+538+676,
388+538+694, 388+538+698, 388+538+699, 388+538+711,
388+538+754, 388+538+760, 388+538+781, 388+538+786,
388+538+797, 388+538+834, 388+538+835, 388+598+602,
388+598+605, 388+598+609, 388+598+676, 388+598+694,
388+598+698, 388+598+699, 388+598+711, 388+598+754,
388+598+760, 388+598+781, 388+598+786, 388+598+797,
388+598+834, 388+598+835, 388+602+605, 388+602+609,
388+602+676, 388+602+694, 388+602+698, 388+602+699,
388+602+711, 388+602+754, 388+602+760, 388+602+781,
388+602+786, 388+602+797, 388+602+834, 388+602+835,
388+605+609, 388+605+676, 388+605+694, 388+605+698,
388+605+699, 388+605+711, 388+605+754, 388+605+760,
388+605+781, 388+605+786, 388+605+797, 388+605+834,
388+605+835, 388+609+676, 388+609+694, 388+609+698,
388+609+699, 388+609+711, 388+609+754, 388+609+760,
388+609+781, 388+609+786, 388+609+797, 388+609+834,
388+609+835, 388+676+694, 388+676+698, 388+676+699,
388+676+711, 388+676+754, 388+676+760, 388+676+781,
388+676+786, 388+676+797, 388+676+834, 388+676+835,
388+694+698, 388+694+699, 388+694+711, 388+694+754,
388+694+760, 388+694+781, 388+694+786, 388+694+797,
388+694+834, 388+694+835, 388+698+699, 388+698+711,
388+698+754, 388+698+760, 388+698+781, 388+698+786,

388+698+797, 388+698+834, 388+698+835, 388+699+711, 388+699+754, 388+699+760, 388+699+781, 388+699+786, 388+699+797, 388+699+834, 388+699+835, 388+711+754, 388+711+760, 388+711+781, 388+711+786, 388+711+797, 388+711+834, 388+711+835, 388+754+760, 388+754+781, 388+754+786, 388+754+797, 388+754+834, 388+754+835, 388+760+781, 388+760+786, 388+760+797, 388+760+834, 388+760+835, 388+781+786, 388+781+797, 388+781+834, 388+781+835, 388+786+797, 388+786+834, 388+786+835, 388+797+834, 388+797+835, 388+834+835, 390+403+408, 390+403+410, 390+403+416, 390+403+448, 390+403+451, 390+403+471, 390+403+472, 390+403+507, 390+403+512, 390+403+515, 390+403+538, 390+403+598, 390+403+602, 390+403+605, 390+403+609, 390+403+676, 390+403+694, 390+403+698, 390+403+699, 390+403+711, 390+403+754, 390+403+760, 390+403+781, 390+403+786, 390+403+797, 390+403+834, 390+403+835, 390+408+410, 390+408+416, 390+408+448, 390+408+451, 390+408+471, 390+408+472, 390+408+507, 390+408+512, 390+408+515, 390+408+538, 390+408+598, 390+408+602, 390+408+605, 390+408+609, 390+408+676, 390+408+694, 390+408+698, 390+408+699, 390+408+711, 390+408+754, 390+408+760, 390+408+781, 390+408+786, 390+408+797, 390+408+834, 390+408+835, 390+410+416, 390+410+448, 390+410+451, 390+410+471, 390+410+472, 390+410+507, 390+410+512, 390+410+515, 390+410+538, 390+410+598, 390+410+602, 390+410+605, 390+410+609, 390+410+676, 390+410+694, 390+410+698, 390+410+699, 390+410+711, 390+410+754, 390+410+760, 390+410+781, 390+410+786, 390+410+797, 390+410+834, 390+410+835, 390+416+448, 390+416+451, 390+416+471, 390+416+472, 390+416+507, 390+416+512, 390+416+515, 390+416+538, 390+416+598, 390+416+602, 390+416+605, 390+416+609, 390+416+676, 390+416+694, 390+416+698, 390+416+699, 390+416+711, 390+416+754, 390+416+760, 390+416+781, 390+416+786, 390+416+797, 390+416+834, 390+416+835, 390+448+451, 390+448+471, 390+448+472, 390+448+507, 390+448+512, 390+448+515, 390+448+538, 390+448+598, 390+448+602, 390+448+605, 390+448+609, 390+448+676, 390+448+694, 390+448+698, 390+448+699, 390+448+711, 390+448+754, 390+448+760, 390+448+781, 390+448+786, 390+448+797, 390+448+834, 390+448+835, 390+451+471, 390+451+472, 390+451+507, 390+451+512, 390+451+515, 390+451+538, 390+451+598, 390+451+602, 390+451+605, 390+451+609, 390+451+676, 390+451+694, 390+451+698, 390+451+699, 390+451+711, 390+451+754, 390+451+760, 390+451+781, 390+451+786, 390+451+797, 390+451+834, 390+451+835, 390+471+472, 390+471+507, 390+471+512, 390+471+515, 390+471+538, 390+471+598, 390+471+602, 390+471+605, 390+471+609, 390+471+676, 390+471+694, 390+471+698, 390+471+699, 390+471+711, 390+471+754, 390+471+760, 390+471+781, 390+471+786, 390+471+797, 390+471+834, 390+471+835, 390+472+507, 390+472+512, 390+472+515, 390+472+538, 390+472+598, 390+472+602, 390+472+605, 390+472+609, 390+472+676, 390+472+694, 390+472+698, 390+472+699, 390+472+711, 390+472+754, 390+472+760, 390+472+781, 390+472+786, 390+472+797, 390+472+834, 390+472+835, 390+507+512, 390+507+515, 390+507+538, 390+507+598, 390+507+602, 390+507+605, 390+507+609, 390+507+676, 390+507+694, 390+507+698, 390+507+699, 390+507+711, 390+507+754, 390+507+760, 390+507+781, 390+507+786, 390+507+797, 390+507+834, 390+507+835, 390+512+515, 390+512+538, 390+512+598, 390+512+602, 390+512+605, 390+512+609, 390+512+676, 390+512+694, 390+512+698, 390+512+699, 390+512+711, 390+512+754, 390+512+760, 390+512+781, 390+512+786, 390+512+797, 390+512+834, 390+512+835, 390+515+538, 390+515+598, 390+515+602, 390+515+605, 390+515+609, 390+515+676, 390+515+694, 390+515+698, 390+515+699, 390+515+711, 390+515+754, 90+515+760, 390+515+781, 390+515+786, 390+515+797, 390+515+834, 390+515+835, 390+538+598, 390+538+602, 390+538+605, 390+538+609, 390+538+676, 390+538+694, 390+538+698, 390+538+699, 390+538+711, 390+538+754, 390+538+760, 390+538+781, 390+538+786, 390+538+797, 390+538+834, 390+538+835, 390+598+602, 390+598+605, 390+598+609, 390+598+676, 390+598+694, 390+598+698, 390+598+699, 390+598+711, 390+598+754, 390+598+760, 390+598+781, 390+598+786, 390+598+797, 390+598+834, 390+598+835, 390+602+605, 390+602+609, 390+602+676, 390+602+694, 390+602+698, 390+602+699, 390+602+711, 390+602+754, 390+602+760, 390+602+781, 390+602+786, 390+602+797, 390+602+834, 390+602+835, 390+605+609, 390+605+676, 390+605+694, 390+605+698, 390+605+699, 390+605+711, 390+605+754, 390+605+760, 390+605+781, 390+605+786, 390+605+797, 390+605+834, 390+605+835, 390+609+676, 390+609+694, 390+609+698, 390+609+699, 390+609+711, 390+609+754, 390+609+760, 390+609+781, 390+609+786, 390+609+797, 390+609+834, 390+609+835, 390+676+694, 390+676+698, 390+676+699. 390+676+711, 390+676+754, 390+676+760, 390+676+781, 390+676+786, 390+676+797, 390+676+834, 390+676+835, 390+694+698, 390+694+699, 390+694+711, 390+694+754, 390+694+760, 390+694+781, 390+694+786, 390+694+797, 390+694+834, 390+694+835, 390+698+699, 390+698+711, 390+698+754, 390+698+760, 390+698+781, 390+698+786, 390+698+797, 390+698+834, 390+698+835, 390+699+711, 390+699+754, 390+699+760, 390+699+781, 390+699+786, 390+699+797, 390+699+834, 390+699+835, 390+711+754, 390+711+760, 390+711+781, 390+711+786, 390+711+797, 390+711+834, 390+711+835, 390+754+760, 390+754+781, 390+754+786, 390+754+797, 390+754+834, 390+754+835, 390+760+781, 390+760+786, 390+760+797, 390+760+834, 390+760+835, 390+781+786, 390+781+797, 390+781+834, 390+781+835, 390+786+797, 390+786+834, 390+786+835, 390+797+834, 390+797+835, 390+834+835, 403+408+410, 403+408+416, 403+408+448, 403+408+451, 403+408+471, 403+408+472, 403+408+507, 403+408+512, 403+408+515, 403+408+538, 403+408+598, 403+408+602, 403+408+605, 403+408+609, 403+408+676, 403+408+694, 403+408+698, 403+408+699, 403+408+711, 403+408+754, 403+408+760, 403+408+781, 403+408+786, 403+408+797, 403+408+834, 403+408+835, 403+410+416, 403+410+448, 403+410+451, 403+410+471, 403+410+472, 403+410+507, 403+410+512, 403+410+515, 403+410+538, 403+410+598, 403+410+602, 403+410+605, 403+410+609, 403+410+676, 403+410+694, 403+410+698, 403+410+699, 403+410+711, 403+410+754, 403+410+760, 403+410+781, 403+410+786, 403+410+797, 403+410+834, 403+410+835, 403+416+448, 403+416+451, 403+416+471, 403+416+472, 403+416+507, 403+416+512, 403+416+515, 403+416+538, 403+416+598, 403+416+602, 403+416+605, 403+416+609, 403+416+676, 403+416+694, 403+416+698, 403+416+699, 403+416+711, 403+416+754, 403+416+760, 403+416+781, 403+416+786, 403+416+797, 403+416+834, 403+416+835, 403+448+451, 403+448+471, 403+448+472, 403+448+507, 403+448+512, 403+448+515, 403+448+538, 403+448+598, 403+448+602, 403+448+605, 403+448+609, 403+448+676, 403+448+694, 403+448+698, 403+448+699, 403+448+711, 403+448+754, 403+448+760, 403+448+781, 403+448+786, 403+448+797, 403+448+834, 403+448+835, 403+451+471, 403+451+472, 403+451+507, 403+451+512, 403+451+515. 403+451+538, 403+451+598, 403+451+602, 403+451+605, 403+451+609, 403+451+676, 403+451+694, 403+451+698, 403+451+699, 403+451+711, 403+451+754, 403+451+760, 403+451+781, 403+451+786, 403+451+797, 403+451+834,

403+451+835, 403+471+472, 403+471+507, 403+471+512, 403+471+515, 403+471+538, 403+471+598, 403+471+602, 403+471+605, 403+471+609, 403+471+676, 403+471+694, 403+471+698, 403+471+699, 403+471+711, 403+471+754, 403+471+760, 403+471+781, 403+471+786, 403+471+797, 403+471+834, 403+471+835, 403+472+507, 403+472+512, 403+472+515, 403+472+538, 403+472+598, 403+472+602, 403+472+605, 403+472+609, 403+472+676, 403+472+694, 403+472+698, 403+472+699, 403+472+711, 403+472+754, 403+472+760, 403+472+781, 403+472+786, 403+472+797, 403+472+834, 403+472+835, 403+507+512, 403+507+515, 403+507+538, 403+507+598, 403+507+602, 403+507+605, 403+507+609, 403+507+676, 403+507+694, 403+507+698, 403+507+699, 403+507+711, 403+507+754, 403+507+760, 403+507+781, 403+507+786, 403+507+797, 403+507+834, 403+507+835, 403+512+515, 403+512+538, 403+512+598, 403+512+602, 403+512+605, 403+512+609, 403+512+676, 403+512+694, 403+512+698, 403+512+699, 403+512+711, 403+512+754, 403+512+760, 403+512+781, 403+512+786, 403+512+797, 403+512+834, 403+512+835, 403+515+538, 403+515+598, 403+515+602, 403+515+605, 403+515+609, 403+515+676, 403+515+694, 403+515+698, 403+515+699, 403+515+711, 403+515+754, 403+515+760, 403+515+781, 403+515+786, 403+515+797, 403+515+834, 403+515+835, 403+538+598, 403+538+602, 403+538+605, 403+538+609, 403+538+676, 403+538+694, 403+538+698, 403+538+699, 403+538+711, 403+538+754, 403+538+760, 403+538+781, 403+538+786, 403+538+797, 403+538+834, 403+538+835, 403+598+602, 403+598+605, 403+598+609, 403+598+676, 403+598+694, 403+598+698, 403+598+699, 403+598+711, 403+598+754, 403+598+760, 403+598+781, 403+598+786, 403+598+797, 403+598+834, 403+598+835, 403+602+605, 403+602+609, 403+602+676, 403+602+694, 403+602+698, 403+602+699, 403+602+711, 403+602+754, 403+602+760, 403+602+781, 403+602+786, 403+602+797, 403+602+834, 403+602+835, 403+605+609, 403+605+676, 403+605+694, 403+605+698, 403+605+699, 403+605+711, 403+605+754, 403+605+760, 403+605+781, 403+605+786, 403+605+797, 403+605+834, 403+605+835, 403+609+676, 403+609+694, 403+609+698, 403+609+699, 403+609+711, 403+609+754, 403+609+760, 403+609+781, 403+609+786, 403+609+797, 403+609+834, 403+609+835, 403+676+694, 403+676+698, 403+676+699, 403+676+711, 403+676+754, 403+676+760, 403+676+781, 403+676+786, 403+676+797, 403+676+834, 403+676+835, 403+694+698, 403+694+699, 403+694+711, 403+694+754, 403+694+760, 403+694+781, 403+694+786, 403+694+797, 403+694+834, 403+694+835, 403+698+699, 403+698+711, 403+698+754, 403+698+760, 403+698+781, 403+698+786, 403+698+797, 403+698+834, 403+698+835, 403+699+711, 403+699+754, 403+699+760, 403+699+781, 403+699+786, 403+699+797, 403+699+834, 403+699+835, 403+711+754, 403+711+760, 403+711+781, 403+711+786, 403+711+797, 403+711+834, 403+711+835, 403+754+760, 403+754+781, 403+754+786, 403+754+797, 403+754+834, 403+754+835, 403+760+781, 403+760+786, 403+760+797, 403+760+834, 403+760+835, 403+781+786, 403+781+797, 403+781+834, 403+781+835, 403+786+797, 403+786+834, 403+786+835, 403+797+834, 403+797+835, 403+834+835, 408+410+416, 408+410+448, 408+410+451, 408+410+471, 408+410+472, 408+410+507, 408+410+512, 408+410+515, 408+410+538, 408+410+598, 408+410+602, 408+410+605, 408+410+609, 408+410+676, 408+410+694, 408+410+698, 408+410+699, 408+410+711, 408+410+754, 408+410+760, 408+410+781, 408+410+786, 408+410+797, 408+410+834, 408+410+835, 408+416+448, 408+416+451, 408+416+471, 408+416+472, 408+416+507, 408+416+512, 408+416+515, 408+416+538, 408+416+598, 408+416+602, 408+416+605, 408+416+609, 408+416+676, 408+416+694, 408+416+698, 408+416+699, 408+416+711, 408+416+754, 408+416+760, 408+416+781, 408+416+786, 408+416+797, 408+416+834, 408+416+835, 408+448+451, 408+448+471, 408+448+472, 408+448+507, 408+448+512, 408+448+515, 408+448+538, 408+448+598, 408+448+602, 408+448+605, 408+448+609, 408+448+676, 408+448+694, 408+448+698, 408+448+699, 408+448+711, 408+448+754, 408+448+760, 408+448+781, 408+448+786, 408+448+797, 408+448+834, 408+448+835, 408+451+471, 408+451+472, 408+451+507, 408+451+512, 408+451+515, 408+451+538, 408+451+598, 408+451+602, 408+451+605, 408+451+609, 408+451+676, 408+451+694, 408+451+698, 408+451+699, 408+451+711, 408+451+754, 408+451+760, 408+451+781, 408+451+786, 408+451+797, 408+451+834, 408+451+835, 408+471+472, 408+471+507, 408+471+512, 408+471+515, 408+471+538, 408+471+598, 408+471+602, 408+471+605, 408+471+609, 408+471+676, 408+471+694, 408+471+698, 408+471+699, 408+471+711, 408+471+754, 408+471+760, 408+471+781, 408+471+786, 408+471+797, 408+471+834, 408+471+835, 408+472+507, 408+472+512, 408+472+515, 408+472+538, 408+472+598, 408+472+602, 408+472+605, 408+472+609, 408+472+676, 408+472+694, 408+472+698, 408+472+699, 408+472+711, 408+472+754, 408+472+760, 408+472+781, 408+472+786, 408+472+797, 408+472+834, 408+472+835, 408+507+512, 408+507+515, 408+507+538, 408+507+598, 408+507+602, 408+507+605, 408+507+609, 408+507+676, 408+507+694, 408+507+698, 408+507+699, 408+507+711, 408+507+754, 408+507+760, 408+507+781, 408+507+786, 408+507+797, 408+507+834, 408+507+835, 408+512+515, 408+512+538, 408+512+598, 408+512+602, 408+512+605, 408+512+609, 408+512+676, 408+512+694, 408+512+698, 408+512+699, 408+512+711, 408+512+754, 408+512+760, 408+512+781, 408+512+786, 408+512+797, 408+512+834, 408+512+835, 408+515+538, 408+515+598, 408+515+602, 408+515+605, 408+515+609, 408+515+676, 408+515+694, 408+515+698, 408+515+699, 408+515+711, 408+515+754, 408+515+760, 408+515+781, 408+515+786, 408+515+797, 408+515+834, 408+515+835, 408+538+598, 408+538+602, 408+538+605, 408+538+609, 408+538+676, 408+538+694, 408+538+698, 408+538+699, 408+538+711, 408+538+754, 408+538+760, 408+538+781, 408+538+786, 408+538+797, 408+538+834, 408+538+835, 408+598+602, 408+598+605, 408+598+609, 408+598+676, 408+598+694, 408+598+698, 408+598+699, 408+598+711, 408+598+754, 408+598+760, 408+598+781, 408+598+786, 408+598+797, 408+598+834, 408+598+835, 408+602+605, 408+602+609, 408+602+676, 408+602+694, 408+602+698, 408+602+699, 408+602+711, 408+602+754, 408+602+760, 408+602+781, 408+602+786, 408+602+797, 408+602+834, 408+602+835, 408+605+609, 408+605+676, 408+605+694, 408+605+698, 408+605+699, 408+605+711, 408+605+754, 408+605+760, 408+605+781, 408+605+786, 408+605+797, 408+605+834, 408+605+835, 408+609+676, 408+609+694, 408+609+698, 408+609+699, 408+609+711, 408+609+754, 408+609+760, 408+609+781, 408+609+786, 408+609+797, 408+609+834, 408+609+835, 408+676+694, 408+676+698, 408+676+699, 408+676+711, 408+676+754, 408+676+760, 408+676+781, 408+676+786, 408+676+797, 408+676+834, 408+676+835, 408+694+698, 408+694+699, 408+694+711, 408+694+754, 408+694+760, 408+694+781, 408+694+786, 408+694+797, 408+694+834, 408+694+835, 408+698+699, 408+698+711, 408+698+754, 408+698+760, 408+698+781, 408+698+786, 408+698+797, 408+698+834, 408+698+835, 408+699+711, 408+699+754, 408+699+760, 408+699+781, 408+699+786, 408+699+797, 408+699+834, 408+699+835, 408+711+754, 408+711+760, 408+711+781, 408+711+786, 408+711+797, 408+711+834, 408+711+835,

408+754+760, 408+754+781, 408+754+786, 408+754+797, 408+754+834, 408+754+835, 408+760+781, 408+760+786, 408+760+797, 408+760+834, 408+760+835, 408+781+786, 408+781+797, 408+781+834, 408+781+835, 408+786+797, 408+786+834, 408+786+835, 408+797+834, 408+797+835, 408+834+835, 410+416+448, 410+416+451, 410+416+471, 410+416+472, 410+416+507, 410+416+512, 410+416+515, 410+416+538, 410+416+598, 410+416+602, 410+416+605, 410+416+609, 410+416+676, 410+416+694, 410+416+698, 410+416+699, 410+416+711, 410+416+754, 410+416+760, 410+416+781, 410+416+786, 410+416+797, 410+416+834, 410+416+835, 410+448+451, 410+448+471, 410+448+472, 410+448+507, 410+448+512, 410+448+515, 410+448+538, 410+448+598, 410+448+602, 410+448+605, 410+448+609, 410+448+676, 410+448+694, 410+448+698, 410+448+699, 410+448+711, 410+448+754, 410+448+760, 410+448+781, 410+448+786, 410+448+797, 410+448+834, 410+448+835, 410+451+471, 410+451+472, 410+451+507, 410+451+512, 410+451+515, 410+451+538, 410+451+598, 410+451+602, 410+451+605, 410+451+609, 410+451+676, 410+451+694, 410+451+698, 410+451+699, 410+451+711, 410+451+754, 410+451+760, 410+451+781, 410+451+786, 410+451+797, 410+451+834, 410+451+835, 410+471+472, 410+471+507, 410+471+512, 410+471+515, 410+471+538, 410+471+598, 410+471+602, 410+471+605, 410+471+609, 410+471+676, 410+471+694, 410+471+698, 410+471+699, 410+471+711, 410+471+754, 410+471+760, 410+471+781, 410+471+786, 410+471+797, 410+471+834, 410+471+835, 410+472+507, 410+472+512, 410+472+515, 410+472+538, 410+472+598, 410+472+602, 410+472+605, 410+472+609, 410+472+676, 410+472+694, 410+472+698, 410+472+699, 410+472+711, 410+472+754. 410+472+760, 410+472+781, 410+472+786, 410+472+797, 410+472+834, 410+472+835, 410+507+512, 410+507+515, 410+507+538, 410+507+598, 410+507+602, 410+507+605, 410+507+609, 410+507+676, 410+507+694, 410+507+698, 410+507+699, 410+507+711, 410+507+754, 410+507+760, 410+507+781, 410+507+786, 410+507+797, 410+507+834, 410+507+835, 410+512+515, 410+512+538, 410+512+598, 410+512+602, 410+512+605, 410+512+609, 410+512+676, 410+512+694, 410+512+698, 410+512+699, 410+512+711, 410+512+754, 410+512+760, 410+512+781, 410+512+786, 410+512+797, 410+512+834, 410+512+835, 410+515+538, 410+515+598, 410+515+602, 410+515+605, 410+515+609, 410+515+676, 410+515+694, 410+515+698, 410+515+699, 410+515+711, 410+515+754, 410+515+760, 410+515+781, 410+515+786, 410+515+797, 410+515+834, 410+515+835, 410+538+598, 410+538+602, 410+538+605, 410+538+609, 410+538+676, 410+538+694, 410+538+698, 410+538+699, 410+538+711, 410+538+754, 410+538+760, 410+538+781, 410+538+786, 410+538+797, 410+538+834, 410+538+835, 410+598+602, 410+598+605, 410+598+609, 410+598+676, 410+598+694, 410+598+698, 410+598+699, 410+598+711, 410+598+754, 410+598+760, 410+598+781, 410+598+786, 410+598+797, 410+598+834, 410+598+835, 410+602+605, 410+602+609, 410+602+676, 410+602+694, 410+602+698, 410+602+699, 410+602+711, 410+602+754, 410+602+760, 410+602+781, 410+602+786, 410+602+797, 410+602+834, 410+602+835, 410+605+609, 410+605+676, 410+605+694, 410+605+698, 410+605+699, 410+605+711, 410+605+754, 410+605+760, 410+605+781, 410+605+786, 410+605+797, 410+605+834, 410+605+835, 410+609+676, 410+609+694, 410+609+698, 410+609+699, 410+609+711, 410+609+754, 410+609+760, 410+609+781, 410+609+786, 410+609+797, 410+609+834, 410+609+835, 410+676+694, 410+676+698, 410+676+699, 410+676+711, 410+676+754, 410+676+760, 410+676+781, 410+676+786, 410+676+797, 410+676+834, 410+676+835, 410+694+698, 410+694+699, 410+694+711, 410+694+754, 410+694+760, 410+694+781, 410+694+786, 410+694+797, 410+694+834, 410+694+835, 410+698+699, 410+698+711, 410+698+754, 410+698+760, 410+698+781, 410+698+786, 410+698+797, 410+698+834, 410+698+835, 410+699+711, 410+699+754, 410+699+760, 410+699+781, 410+699+786, 410+699+797, 410+699+834, 410+699+835, 410+711+754, 410+711+760, 410+711+781, 410+711+786, 410+711+797, 410+711+834, 410+711+835, 410+754+760, 410+754+781, 410+754+786, 410+754+797, 410+754+834, 410+754+835, 410+760+781, 410+760+786, 410+760+797, 410+760+834, 410+760+835, 410+781+786, 410+781+797, 410+781+834, 410+781+835, 410+786+797, 410+786+834, 410+786+835, 410+797+834, 410+797+835, 410+834+835, 416+448+451, 416+448+471, 416+448+472, 416+448+507, 416+448+512, 416+448+515, 416+448+538, 416+448+598, 416+448+602, 416+448+605, 416+448+609, 416+448+676, 416+448+694, 416+448+698, 416+448+699, 416+448+711, 416+448+754, 416+448+760, 416+448+781, 416+448+786, 416+448+797, 416+448+834, 416+448+835, 416+451+471, 416+451+472, 416+451+507, 416+451+512, 416+451+515, 416+451+538, 416+451+598, 416+451+602, 416+451+605, 416+451+609, 416+451+676, 416+451+694, 416+451+698, 416+451+699, 416+451+711, 416+451+754, 416+451+760, 416+451+781, 416+451+786, 416+451+797, 416+451+834, 416+451+835, 416+471+472, 416+471+507, 416+471+512, 416+471+515, 416+471+538, 416+471+598, 416+471+602, 416+471+605, 416+471+609, 416+471+676, 416+471+694, 416+471+698, 416+471+699, 416+471+711, 416+471+754, 416+471+760, 416+471+781, 416+471+786, 416+471+797, 416+471+834, 416+471+835, 416+472+507, 416+472+512, 416+472+515, 416+472+538, 416+472+598, 416+472+602, 416+472+605, 416+472+609, 416+472+676, 416+472+694, 416+472+698, 416+472+699, 416+472+711, 416+472+754, 416+472+760, 416+472+781, 416+472+786, 416+472+797, 416+472+834, 416+472+835, 416+507+512, 416+507+515, 416+507+538, 416+507+598, 416+507+602, 416+507+605, 416+507+609, 416+507+676, 416+507+694, 416+507+698, 416+507+699, 416+507+711, 416+507+754, 416+507+760, 416+507+781, 416+507+786, 416+507+797, 416+507+834, 416+507+835, 416+512+515, 416+512+538, 416+512+598, 416+512+602, 416+512+605, 416+512+609, 416+512+676, 416+512+694, 416+512+698, 416+512+699, 416+512+711, 416+512+754, 416+512+760, 416+512+781, 416+512+786, 416+512+797, 416+512+834, 416+512+835, 416+515+538, 416+515+598, 416+515+602, 416+515+605, 416+515+609, 416+515+676, 416+515+694, 416+515+698, 416+515+699, 416+515+711, 416+515+754, 416+515+760, 416+515+781, 416+515+786, 416+515+797, 416+515+834, 416+515+835, 416+538+598, 416+538+602, 416+538+605, 416+538+609, 416+538+676, 416+538+694, 416+538+698, 416+538+699, 416+538+711, 416+538+754, 416+538+760, 416+538+781, 416+538+786, 416+538+797, 416+538+834, 416+538+835, 416+598+602, 416+598+605, 416+598+609, 416+598+676, 416+598+694, 416+598+698, 416+598+699, 416+598+711, 416+598+754, 416+598+760, 416+598+781, 416+598+786, 416+598+797, 416+598+834, 416+598+835, 416+602+605, 416+602+609, 416+602+676, 416+602+694, 416+602+698, 416+602+699, 416+602+711, 416+602+754, 416+602+760, 416+602+781, 416+602+786, 416+602+797, 416+602+834, 416+602+835, 416+605+609, 416+605+676, 416+605+694, 416+605+698, 416+605+699, 416+605+711, 416+605+754, 416+605+760, 416+605+781, 416+605+786, 416+605+797, 416+605+834, 416+605+835, 416+609+676, 416+609+694, 416+609+698, 416+609+699, 416+609+711, 416+609+754, 416+609+760, 416+609+781, 416+609+786, 416+609+797, 416+609+834, 416+609+835, 416+676+694, 416+676+698, 416+676+699, 416+676+711, 416+676+754,

416+676+760,416+676+781, 416+676+786,416+676+797,
416+676+834,416+676+835,416+694+698,416+694+699,
416+694+711, 416+694+754,416+694+760,416+694+781,
416+694+786,416+694+797,416+694+834,416+694+835,
416+698+699,416+698+711,416+698+754,416+698+760,
416+698+781,416+698+786,416+698+797, 416+698+834,
416+698+835,416+699+711,416+699+754,416+699+760,
416+699+781,416+699+786, 416+699+797,416+699+834,
416+699+835,416+711+754,416+711+760,416+711+781,
416+711+786, 416+711+797,416+711+834,416+711+835,
416+754+760,416+754+781,416+754+786,416+754+797,
416+754+834,416+754+835,416+760+781,416+760+786,
416+760+797,416+760+834,416+760+835, 416+781+786,
416+781+797,416+781+834,416+781+835,416+786+797,
416+786+834,416+786+835, 416+797+834,416+797+835,
416+834+835,448+451+471,448+451+472,448+451+507,
448+451+512, 448+451+515,448+451+538,448+451+598,
448+451+602,448+451+605,448+451+609,448+451+676,
448+451+694,448+451+698 448+451+699,448+451+711,
448+451+754,448+451+760,448+451+781, 448+451+786,
448+451+797,448+451+834,448+451+835,448+471+472,
448+471+507,448+471+512, 448+471+515,448+471+538,
448+471+598,448+471+602,448+471+605,448+471+609,
448+471+676, 448+471+694,448+471+698,448+471+699,
448+471+711,448+471+754,448+471+760,448+471+781,
448+471+786,448+471+797,448+471+834,448+471+835,
448+472+507,448+472+512,448+472+515, 448+472+538,
448+472+598,448+472+602,448+472+605,448+472+609,
448+472+676,448+472+694, 448+472+698,448+472+699,
448+472+711,448+472+754,448+472+760,448+472+781,
448+472+786, 448+472+797,448+472+834,448+472+835,
448+507+512,448+507+515,448+507+538,448+507+598,
448+507+602,448+507+605,448+507+609,448+507+676,
448+507+694,448+507+698,448+507+699, 448+507+711,
448+507+754,448+507+760,448+507+781,448+507+786,
448+507+797,448+507+834, 448+507+835,448+512+515,
448+512+538,448+512+598,448+512+602,448+512+605,
448+512+609, 448+512+676,448+512+694,448+512+698,
448+512+699,448+512+711,448+512+754,448+512+760,
448+512+781,448+512+786,448+512+797,448+512+834,
448+512+835,448+515+538,448+515+598, 448+515+602,
448+515+605,448+515+609,448+515+676,448+515+694,
448+515+698,448+515+699, 448+515+711,448+515+754,
448+515+760,448+515+781,448+515+786,448+515+797,
448+515+834, 448+515+835,448+538+598,448+538+602,
448+538+605,448+538+609,448+538+676,448+538+694,
448+538+698,448+538+699,448+538+711,448+538+754,
448+538+760,448+538+781,448+538+786, 448+538+797,
448+538+834,448+538+835,448+598+602,448+598+605,
448+598+609,448+598+676, 448+598+694,448+598+698,
448+598+699,448+598+711,448+598+754,448+598+760,
448+598+781, 448+598+786,448+598+797,448+598+834,
448+598+835,448+602+605,448+602+609,448+602+676,
448+602+694,448+602+698,448+602+699,448+602+711,
448+602+754,448+602+760,448+602+781, 448+602+786,
448+602+797,448+602+834,448+602+835,448+605+609,
448+605+676,448+605+694, 448+605+698,448+605+699,
448+605+711,448+605+754,448+605+760,448+605+781,
448+605+786, 448+605+797,448+605+834,448+605+835,
448+609+676,448+609+694,448+609+698,448+609+699,
448+609+711,448+609+754,448+609+760,448+609+781,
448+609+786,448+609+797,448+609+834, 448+609+835,
448+676+694,448+676+698,448+676+699,448+676+711,
448+676+754,448+676+760, 448+676+781,448+676+786,
448+676+797,448+676+834,448+676+835,448+694+698,
448+694+699, 448+694+711,448+694+754,448+694+760,
448+694+781,448+694+786,448+694+797,448+694+834,
448+694+835,448+698+699,448+698+711,448+698+754,
448+698+760,448+698+781,448+698+786, 448+698+797,
448+698+834,448+698+835,448+698+699+711,448+699+754,
448+699+760,448+699+781, 448+699+786,448+699+797,
448+699+834,448+699+835,448+711+754,448+711+760,
448+711+781, 448+711+786,448+711+797,448+711+834,
448+711+835,448+754+760,448+754+781,448+754+786,
448+754+797,448+754+834,448+754+835,448+760+781,
448+760+786,448+760+797,448+760+834, 448+760+835,
448+781+786,448+781+797,448+781+834,448+781+835,
448+786+797,448+786+834, 448+786+835,448+797+834,
448+797+835,448+834+835,451+471+472,451+471+507,
451+471+512, 451+471+515,451+471+538,451+471+598,
451+471+602,451+471+605,451+471+609,451+471+676,
451+471+694,451+471+698,451+471+699,451+471+711,
451+471+754,451+471+760,451+471+781, 451+471+786,
451+471+797,451+471+834,451+471+835,451+472+507,
451+472+512,451+472+515, 451+472+538,451+472+598,
451+472+602,451+472+605,451+472+609,451+472+676,
451+472+694, 451+472+698,451+472+699,451+472+711,
451+472+754,451+472+760,451+472+781,451+472+786,
451+472+797,451+472+834,451+472+835,451+507+512,
451+507+515,451+507+538,451+507+598, 451+507+602,
451+507+605,451+507+609,451+507+676,451+507+694,
451+507+698,451+507+699, 451+507+711,451+507+754,
451+507+760,451+507+781,451+507+786,451+507+797,
451+507+834, 451+507+835,451+512+515,451+512+538,
451+512+598,451+512+602,451+512+605,451+512+609,
451+512+676,451+512+694,451+512+698,451+512+699,
451+512+711,451+512+754,451+512+760, 451+512+781,
451+512+786,451+512+797,451+512+834,451+512+835,
451+515+538,451+515+598, 451+515+602,451+515+605,
451+515+609,451+515+676,451+515+694,451+515+698,
451+515+699, 451+515+711,451+515+754,451+515+760,
451+515+781,451+515+786,451+515+797,451+515+834,
451+515+835,451+538+598,451+538+602,451+538+605,
451+538+609,451+538+676,451+538+694, 451+538+698,
451+538+699,451+538+711,451+538+754,451+538+760,
451+538+781,451+538+786, 451+538+797,451+538+834,
451+538+835,451+598+602,451+598+605,451+598+609,
451+598+676, 451+598+694,451+598+698,451+598+699,
451+598+711,451+598+754,451+598+760,451+598+781,
451+598+786,451+598+797,451+598+834,451+598+835,
451+602+605,451+602+609,451+602+676, 451+602+694,
451+602+698,451+602+699,451+602+711,451+602+754,
451+602+760,451+602+781, 451+602+786,451+602+797,
451+602+834,451+602+835,451+605+609,451+605+676,
451+605+694, 451+605+698,451+605+699,451+605+711,
451+605+754,451+605+760,451+605+781,451+605+786,
451+605+797,451+605+834,451+605+835,451+609+676,
451+609+694,451+609+698,451+609+699, 451+609+711,
451+609+754,451+609+760,451+609+781,451+609+786,
451+609+797,451+609+834, 451+609+835,451+676+694,
451+676+698,451+676+699,451+676+711,451+676+754,
451+676+760, 451+676+781,451+676+786,451+676+797,
451+676+834,451+676+835,451+694+698,451+694+699,
451+694+711,451+694+754,451+694+760,451+694+781,
451+694+786,451+694+797,451+694+834, 451+694+835,
451+698+699,451+698+711,451+698+754,451+698+760,
451+698+781,451+698+786, 451+698+797,451+698+834,
451+698+835,451+699+711,451+699+754,451+699+760,
451+699+781, 451+699+786,451+699+797,451+699+834,
451+699+835,451+711+754,451+711+760,451+711+781,
451+711+786,451+711+797,451+711+834,451+711+835,
451+754+760,451+754+781,451+754+786, 451+754+797,
451+754+834,451+754+835,451+760+781,451+760+786,
451+760+797,451+760+834, 451+760+835,451+781+786,

451+781+797, 451+781+834, 451+781+835, 451+786+797, 451+786+834, 451+786+835, 451+797+834, 451+797+835, 451+834+835, 471+472+507, 471+472+512, 471+472+515, 471+472+538, 471+472+598, 471+472+602, 471+472+605, 471+472+609, 471+472+676, 471+472+694, 471+472+698, 471+472+699, 471+472+711, 471+472+754, 471+472+760, 471+472+781, 471+472+786, 471+472+797, 471+472+834, 471+472+835, 471+507+512, 471+507+515, 471+507+538, 471+507+598, 471+507+602, 471+507+605, 471+507+609, 471+507+676, 471+507+694, 471+507+698, 471+507+699, 471+507+711, 471+507+754, 471+507+760, 471+507+781, 471+507+786, 471+507+797, 471+507+834, 471+507+835, 471+512+515, 471+512+538, 471+512+598, 471+512+602, 471+512+605, 471+512+609, 471+512+676, 471+512+694, 471+512+698, 471+512+699, 471+512+711, 471+512+754, 471+512+760, 471+512+781, 471+512+786, 471+512+797, 471+512+834, 471+512+835, 471+515+538, 471+515+598, 471+515+602, 471+515+605, 471+515+609, 471+515+676, 471+515+694, 471+515+698, 471+515+699, 471+515+711, 471+515+754, 471+515+760, 471+515+781, 471+515+786, 471+515+797, 471+515+834, 471+515+835, 471+538+598, 471+538+602, 471+538+605, 471+538+609, 471+538+676, 471+538+694, 471+538+698, 471+538+699, 471+538+711, 471+538+754, 471+538+760, 471+538+781, 471+538+786, 471+538+797, 471+538+834, 471+538+835, 471+598+602, 471+598+605, 471+598+609, 471+598+676, 471+598+694, 471+598+698, 471+598+699, 471+598+711, 471+598+754, 471+598+760, 471+598+781, 471+598+786, 471+598+797, 471+598+834, 471+598+835, 471+602+605, 471+602+609, 471+602+676, 471+602+694, 471+602+698, 471+602+699, 471+602+711, 471+602+754, 471+602+760, 471+602+781, 471+602+786, 471+602+797, 471+602+834, 471+602+835, 471+605+609, 471+605+676, 471+605+694, 471+605+698, 471+605+699, 471+605+711, 471+605+754, 471+605+760, 471+605+781, 471+605+786, 471+605+797, 471+605+834, 471+605+835, 471+609+676, 471+609+694, 471+609+698, 471+609+699, 471+609+711, 471+609+754, 471+609+760, 471+609+781, 471+609+786, 471+609+797, 471+609+834, 471+609+835, 471+676+694, 471+676+698, 471+676+699, 471+676+711, 471+676+754, 471+676+760, 471+676+781, 471+676+786, 471+676+797, 471+676+834, 471+676+835, 471+694+698, 471+694+699, 471+694+711, 471+694+754, 471+694+760, 471+694+781, 471+694+786, 471+694+797, 471+694+834, 471+694+835, 471+698+699, 471+698+711, 471+698+754, 471+698+760, 471+698+781, 471+698+786, 471+698+797, 471+698+834, 471+698+835, 471+699+711, 471+699+754, 471+699+760, 471+699+781, 471+699+786, 471+699+797, 471+699+834, 471+699+835, 471+711+754, 471+711+760, 471+711+781, 471+711+786, 471+711+797, 471+711+834, 471+711+835, 471+754+760, 471+754+781, 471+754+786, 471+754+797, 471+754+834, 471+754+835, 471+760+781, 471+760+786, 471+760+797, 471+760+834, 471+760+835, 471+781+786, 471+781+797, 471+781+834, 471+781+835, 471+786+797, 471+786+834, 471+786+835, 471+797+834, 471+797+835, 471+834+835, 472+507+512, 472+507+515, 472+507+538, 472+507+598, 472+507+602, 472+507+605, 472+507+609, 472+507+676, 472+507+694, 472+507+698, 472+507+699, 472+507+711, 472+507+754, 472+507+760, 472+507+781, 472+507+786, 472+507+797, 472+507+834, 472+507+835, 472+512+515, 472+512+538, 472+512+598, 472+512+602, 472+512+605, 472+512+609, 472+512+676, 472+512+694, 472+512+698, 472+512+699, 472+512+711, 472+512+754, 472+512+760, 472+512+781, 472+512+786, 472+512+797, 472+512+834, 472+512+835, 472+515+538, 472+515+598, 472+515+602, 472+515+605, 472+515+609, 472+515+676, 472+515+694, 472+515+698, 472+515+699, 472+515+711, 472+515+754, 472+515+760, 472+515+781, 472+515+786, 472+515+797, 472+515+834, 472+515+835, 472+538+598, 472+538+602, 472+538+605, 472+538+609, 472+538+676, 472+538+694, 472+538+698, 472+538+699, 472+538+711, 472+538+754, 472+538+760, 472+538+781, 472+538+786, 472+538+797, 472+538+834, 472+538+835, 472+598+602, 472+598+605, 472+598+609, 472+598+676, 472+598+694, 472+598+698, 472+598+699, 472+598+711, 472+598+754, 472+598+760, 472+598+781, 472+598+786, 472+598+797, 472+598+834, 472+598+835, 472+602+605, 472+602+609, 472+602+676, 472+602+694, 472+602+698, 472+602+699, 472+602+711, 472+602+754, 472+602+760, 472+602+781, 472+602+786, 472+602+797, 472+602+834, 472+602+835, 472+605+609, 472+605+676, 472+605+694, 472+605+698, 472+605+699, 472+605+711, 472+605+754, 472+605+760, 472+605+781, 472+605+786, 472+605+797, 472+605+834, 472+605+835, 472+609+676, 472+609+694, 472+609+698, 472+609+699, 472+609+711, 472+609+754, 472+609+760, 472+609+781, 472+609+786, 472+609+797, 472+609+834, 472+609+835, 472+676+694, 472+676+698, 472+676+699, 472+676+711, 472+676+754, 472+676+760, 472+676+781, 472+676+786, 472+676+797, 472+676+834, 472+676+835, 472+694+698, 472+694+699, 472+694+711, 472+694+754, 472+694+760, 472+694+781, 472+694+786, 472+694+797, 472+694+834, 472+694+835, 472+698+699, 472+698+711, 472+698+754, 472+698+760, 472+698+781, 472+698+786, 472+698+797, 472+698+834, 472+698+835, 472+699+711, 472+699+754, 472+699+760, 472+699+781, 472+699+786, 472+699+797, 472+699+834, 472+699+835, 472+711+754, 472+711+760, 472+711+781, 472+711+786, 472+711+797, 472+711+834, 472+711+835, 472+754+760, 472+754+781, 472+754+786, 472+754+797, 472+754+834, 472+754+835, 472+760+781, 472+760+786, 472+760+797, 472+760+834, 472+760+835, 472+781+786, 472+781+797, 472+781+834, 472+781+835, 472+786+797, 472+786+834, 472+786+835, 472+797+834, 472+797+835, 472+834+835, 507+512+515, 507+512+538, 507+512+598, 507+512+602, 507+512+605, 507+512+609, 507+512+676, 507+512+694, 507+512+698, 507+512+699, 507+512+711, 507+512+754, 507+512+760, 507+512+781, 507+512+786, 507+512+797, 507+512+834, 507+512+835, 507+515+538, 507+515+598, 507+515+602, 507+515+605, 507+515+609, 507+515+676, 507+515+694, 507+515+698, 507+515+699, 507+515+711, 507+515+754, 507+515+760, 507+515+781, 507+515+786, 507+515+797, 507+515+834, 507+515+835, 507+538+598, 507+538+602, 507+538+605, 507+538+609, 507+538+676, 507+538+694, 507+538+698, 507+538+699, 507+538+711, 507+538+754, 507+538+760, 507+538+781, 507+538+786, 507+538+797, 507+538+834, 507+538+835, 507+598+602, 507+598+605, 507+598+609, 507+598+676, 507+598+694, 507+598+698, 507+598+699, 507+598+711, 507+598+754, 507+598+760, 507+598+781, 507+598+786, 507+598+797, 507+598+834, 507+598+835, 507+602+605, 507+602+609, 507+602+676, 507+602+694, 507+602+698, 507+602+699, 507+602+711, 507+602+754, 507+602+760, 507+602+781, 507+602+786, 507+602+797, 507+602+834, 507+602+835, 507+605+609, 507+605+676, 507+605+694, 507+605+698, 507+605+699, 507+605+711, 507+605+754, 507+605+760, 507+605+781, 507+605+786, 507+605+797, 507+605+834, 507+605+835, 507+609+676, 507+609+694, 507+609+698, 507+609+699, 507+609+711, 507+609+754, 507+609+760, 507+609+781, 507+609+786, 507+609+797, 507+609+834, 507+609+835, 507+676+694, 507+676+698, 507+676+699, 507+676+711, 507+676+754, 507+676+760, 507+676+781, 507+676+786, 507+676+797, 507+676+834, 507+676+835, 507+694+698, 507+694+699, 507+694+711, 507+694+754, 507+694+760, 507+694+781, 507+694+786, 507+694+797, 507+694+834, 507+694+835, 507+698+699,

507+698+711, 507+698+754, 507+698+760, 507+698+781, 507+698+786, 507+698+797, 507+698+834, 507+698+835, 507+699+711, 507+699+754, 507+699+760, 507+699+781, 507+699+786, 507+699+797, 507+699+834, 507+699+835, 507+711+754, 507+711+760, 507+711+781, 507+711+786, 507+711+797, 507+711+834, 507+711+835, 507+754+760, 507+754+781, 507+754+786, 507+754+797, 507+754+834, 507+754+835, 507+760+781, 507+760+786, 507+760+797, 507+760+834, 507+760+835, 507+781+786, 507+781+797, 507+781+834, 507+781+835, 507+786+797, 507+786+834, 507+786+835, 507+797+834, 507+797+835, 507+834+835, 512+515+538, 512+515+598, 512+515+602, 512+515+605, 512+515+609, 512+515+676, 512+515+694, 512+515+698, 512+515+699, 512+515+711, 512+515+754, 512+515+760, 512+515+781, 512+515+786, 512+515+797, 512+515+834, 512+515+835, 512+538+598, 512+538+602, 512+538+605, 512+538+609, 512+538+676, 512+538+694, 512+538+698, 512+538+699, 512+538+711, 512+538+754, 512+538+760, 512+538+781, 512+538+786, 512+538+797, 512+538+834, 512+538+835, 512+598+602, 512+598+605, 512+598+609, 512+598+676, 512+598+694, 512+598+698, 512+598+699, 512+598+711, 512+598+754, 512+598+760, 512+598+781, 512+598+786, 512+598+797, 512+598+834, 512+598+835, 512+602+605, 512+602+609, 512+602+676, 512+602+694, 512+602+698, 512+602+699, 512+602+711, 512+602+754, 512+602+760, 512+602+781, 512+602+786, 512+602+797, 512+602+834, 512+602+835, 512+605+609, 512+605+676, 512+605+694, 512+605+698, 512+605+699, 512+605+711, 512+605+754, 512+605+760, 512+605+781, 512+605+786, 512+605+797, 512+605+834, 512+605+835, 512+609+676, 512+609+694, 512+609+698, 512+609+699, 512+609+711, 512+609+754, 512+609+760, 512+609+781, 512+609+786, 512+609+797, 512+609+834, 512+609+835, 512+676+694, 512+676+698, 512+676+699, 512+676+711, 512+676+754, 512+676+760, 512+676+781, 512+676+786, 512+676+797, 512+676+834, 512+676+835, 512+694+698, 512+694+699, 512+694+711, 512+694+754, 512+694+760, 512+694+781, 512+694+786, 512+694+797, 512+694+834, 512+694+835, 512+698+699, 512+698+711, 512+698+754, 512+698+760, 512+698+781, 512+698+786, 512+698+797, 512+698+834, 512+698+835, 512+699+711, 512+699+754, 512+699+760, 512+699+781, 512+699+786, 512+699+797, 512+699+834, 512+699+835, 512+711+754, 512+711+760, 512+711+781, 512+711+786, 512+711+797, 512+711+834, 512+711+835, 512+754+760, 512+754+781, 512+754+786, 512+754+797, 512+754+834, 512+754+835, 512+760+781, 512+760+786, 512+760+797, 512+760+834, 512+760+835, 512+781+786, 512+781+797, 512+781+834, 512+781+835, 512+786+797, 512+786+834, 512+786+835, 512+797+834, 512+797+835, 512+834+835, 515+538+598, 515+538+602, 515+538+605, 515+538+609, 515+538+676, 515+538+694, 515+538+698, 515+538+699, 515+538+711, 515+538+754, 515+538+760, 515+538+781, 515+538+786, 515+538+797, 515+538+834, 515+538+835, 515+598+602, 515+598+605, 515+598+609, 515+598+676, 515+598+694, 515+598+698, 515+598+699, 515+598+711, 515+598+754, 515+598+760, 515+598+781, 515+598+786, 515+598+797, 515+598+834, 515+598+835, 515+602+605, 515+602+609, 515+602+676, 515+602+694, 515+602+698, 515+602+699, 515+602+711, 515+602+754, 515+602+760, 515+602+781, 515+602+786, 515+602+797, 515+602+834, 515+602+835, 515+605+609, 515+605+676, 515+605+694, 515+605+698, 515+605+699, 515+605+711, 515+605+754, 515+605+760, 515+605+781, 515+605+786, 515+605+797, 515+605+834, 515+605+835, 515+609+676, 515+609+694, 515+609+698, 515+609+699, 515+609+711, 515+609+754, 515+609+760, 515+609+781, 515+609+786, 515+609+797, 515+609+834, 515+609+835, 515+676+694, 515+676+698, 515+676+699, 515+676+711, 515+676+754, 515+676+760, 515+676+781, 515+676+786, 515+676+797, 515+676+834, 515+676+835, 515+694+698, 515+694+699, 515+694+711, 515+694+754, 515+694+760, 515+694+781, 515+694+786, 515+694+797, 515+694+834, 515+694+835, 515+698+699, 515+698+711, 515+698+754, 515+698+760, 515+698+781, 515+698+786, 515+698+797, 515+698+834, 515+698+835, 515+699+711, 515+699+754, 515+699+760, 515+699+781, 515+699+786, 515+699+797, 515+699+834, 515+699+835, 515+711+754, 515+711+760, 515+711+781, 515+711+786, 515+711+797, 515+711+834, 515+711+835, 515+754+760, 515+754+781, 515+754+786, 515+754+797, 515+754+834, 515+754+835, 515+760+781, 515+760+786, 515+760+797, 515+760+834, 515+760+835, 515+781+786, 515+781+797, 515+781+834, 515+781+835, 515+786+797, 515+786+834, 515+786+835, 515+797+834, 515+797+835, 515+834+835, 538+598+602, 538+598+605, 538+598+609, 538+598+676, 538+598+694, 538+598+698, 538+598+699, 538+598+711, 538+598+754, 538+598+760, 538+598+781, 538+598+786, 538+598+797, 538+598+834, 538+598+835, 538+602+605, 538+602+609, 538+602+676, 538+602+694, 538+602+698, 538+602+699, 538+602+711, 538+602+754, 538+602+760, 538+602+781, 538+602+786, 538+602+797, 538+602+834, 538+602+835, 538+605+609, 538+605+676, 538+605+694, 538+605+698, 538+605+699, 538+605+711, 538+605+754, 538+605+760, 538+605+781, 538+605+786, 538+605+797, 538+605+834, 538+605+835, 538+609+676, 538+609+694, 538+609+698, 538+609+699, 538+609+711, 538+609+754, 538+609+760, 538+609+781, 538+609+786, 538+609+797, 538+609+834, 538+609+835, 538+676+694, 538+676+698, 538+676+699, 538+676+711, 538+676+754, 538+676+760, 538+676+781, 538+676+786, 538+676+797, 538+676+834, 538+676+835, 538+694+698, 538+694+699, 538+694+711, 538+694+754, 538+694+760, 538+694+781, 538+694+786, 538+694+797, 538+694+834, 538+694+835, 538+698+699, 538+698+711, 538+698+754, 538+698+760, 538+698+781, 538+698+786, 538+698+797, 538+698+834, 538+698+835, 538+699+711, 538+699+754, 538+699+760, 538+699+781, 538+699+786, 538+699+797, 538+699+834, 538+699+835, 538+711+754, 538+711+760, 538+711+781, 538+711+786, 538+711+797, 538+711+834, 538+711+835, 538+754+760, 538+754+781, 538+754+786, 538+754+797, 538+754+834, 538+754+835, 538+760+781, 538+760+786, 538+760+797, 538+760+834, 538+760+835, 538+781+786, 538+781+797, 538+781+834, 538+781+835, 538+786+797, 538+786+834, 538+786+835, 538+797+834, 538+797+835, 538+834+835, 598+602+605, 598+602+609, 598+602+676, 598+602+694, 598+602+698, 598+602+699, 598+602+711, 598+602+754, 598+602+760, 598+602+781, 598+602+786, 598+602+797, 598+602+834, 598+602+835, 598+605+609, 598+605+676, 598+605+694, 598+605+698, 598+605+699, 598+605+711, 598+605+754, 598+605+760, 598+605+781, 598+605+786, 598+605+797, 598+605+834, 598+605+835, 598+609+676, 598+609+694, 598+609+698, 598+609+699, 598+609+711, 598+609+754, 598+609+760, 598+609+781, 598+609+786, 598+609+797, 598+609+834, 598+609+835, 598+676+694, 598+676+698, 598+676+699, 598+676+711, 598+676+754, 598+676+760, 598+676+781, 598+676+786, 598+676+797, 598+676+834, 598+676+835, 598+694+698, 598+694+699, 598+694+711, 598+694+754, 598+694+760, 598+694+781, 598+694+786, 598+694+797, 598+694+834, 598+694+835, 598+698+699, 598+698+711, 598+698+754, 598+698+760, 598+698+781, 598+698+786, 598+698+797, 598+698+834, 598+698+835, 598+699+711, 598+699+754, 598+699+760, 598+699+781, 598+699+786, 598+699+797, 598+699+834, 598+699+835, 598+711+754, 598+711+760, 598+711+781, 598+711+786, 598+711+797, 598+711+834,

598+711+835, 598+754+760, 598+754+781, 598+754+786, 598+754+797, 598+754+834, 598+754+835, 598+760+781, 598+760+786, 598+760+797, 598+760+834, 598+760+835, 598+781+786, 598+781+797, 598+781+834, 598+781+835, 598+786+797, 598+786+834, 598+786+835, 598+797+834, 598+797+835, 598+834+835, 602+605+609, 602+605+676, 602+605+694, 602+605+698, 602+605+699, 602+605+711, 602+605+754, 602+605+760, 602+605+781, 602+605+786, 602+605+797, 602+605+834, 602+605+835, 602+609+676, 602+609+694, 602+609+698, 602+609+699, 602+609+711, 602+609+754, 602+609+760, 602+609+781, 602+609+786, 602+609+797, 602+609+834, 602+609+835, 602+676+694, 602+676+698, 602+676+699, 602+676+711, 602+676+754, 602+676+760, 602+676+781, 602+676+786, 602+676+797, 602+676+834, 602+676+835, 602+694+698, 602+694+699, 602+694+711, 602+694+754, 602+694+760, 602+694+781, 602+694+786, 602+694+797, 602+694+834, 602+694+835, 602+698+699, 602+698+711, 602+698+754, 602+698+760, 602+698+781, 602+698+786, 602+698+797, 602+698+834, 602+698+835, 602+699+711, 602+699+754, 602+699+760, 602+699+781, 602+699+786, 602+699+797, 602+699+834, 602+699+835, 602+711+754, 602+711+760, 602+711+781, 602+711+786, 602+711+797, 602+711+834, 602+711+835, 602+754+760, 602+754+781, 602+754+786, 602+754+797, 602+754+834, 602+754+835, 602+760+781, 602+760+786, 602+760+797, 602+760+834, 602+760+835, 602+781+786, 602+781+797, 602+781+834, 602+781+835, 602+786+797, 602+786+834, 602+786+835, 602+797+834, 602+797+835, 602+834+835, 605+609+676, 605+609+694, 605+609+698, 605+609+699, 605+609+711, 605+609+754, 605+609+760, 605+609+781, 605+609+786, 605+609+797, 605+609+834, 605+609+835, 605+676+694, 605+676+698, 605+676+699, 605+676+711, 605+676+754, 605+676+760, 605+676+781, 605+676+786, 605+676+797, 605+676+834, 605+676+835, 605+694+698, 605+694+699, 605+694+711, 605+694+754, 605+694+760, 605+694+781, 605+694+786, 605+694+797, 605+694+834, 605+694+835, 605+698+699, 605+698+711, 605+698+754, 605+698+760, 605+698+781, 605+698+786, 605+698+797, 605+698+834, 605+698+835, 605+699+711, 605+699+754, 605+699+760, 605+699+781, 605+699+786, 605+699+797, 605+699+834, 605+699+835, 605+711+754, 605+711+760, 605+711+781, 605+711+786, 605+711+797, 605+711+834, 605+711+835, 605+754+760, 605+754+781, 605+754+786, 605+754+797, 605+754+834, 605+754+835, 605+760+781, 605+760+786, 605+760+797, 605+760+834, 605+760+835, 605+781+786, 605+781+797, 605+781+834, 605+781+835, 605+786+797, 605+786+834, 605+786+835, 605+797+834, 605+797+835, 605+834+835, 609+676+694, 609+676+698, 609+676+699, 609+676+711, 609+676+754, 609+676+760, 609+676+781, 609+676+786, 609+676+797, 609+676+834, 609+676+835, 609+694+698, 609+694+699, 609+694+711, 609+694+754, 609+694+760, 609+694+781, 609+694+786, 609+694+797, 609+694+834, 609+694+835, 609+698+699, 609+698+711, 609+698+754, 609+698+760, 609+698+781, 609+698+786, 609+698+797, 609+698+834, 609+698+835, 609+699+711, 609+699+754, 609+699+760, 609+699+781, 609+699+786, 609+699+797, 609+699+834, 609+699+835, 609+711+754, 609+711+760, 609+711+781, 609+711+786, 609+711+797, 609+711+834, 609+711+835, 609+754+760, 609+754+781, 609+754+786, 609+754+797, 609+754+834, 609+754+835, 609+760+781, 609+760+786, 609+760+797, 609+760+834, 609+760+835, 609+781+786, 609+781+797, 609+781+834, 609+781+835, 609+786+797, 609+786+834, 609+786+835, 609+797+834, 609+797+835, 609+834+835, 676+694+698, 676+694+699, 676+694+711, 676+694+754, 676+694+760, 676+694+781, 676+694+786, 676+694+797, 676+694+834, 676+694+835, 676+698+699, 676+698+711, 676+698+754, 676+698+760, 676+698+781, 676+698+786, 676+698+797, 676+698+834, 676+698+835, 676+699+711, 676+699+754, 676+699+760, 676+699+781, 676+699+786, 676+699+797, 676+699+834, 676+699+835, 676+711+754, 676+711+760, 676+711+781, 676+711+786, 676+711+797, 676+711+834, 676+711+835, 676+754+760, 676+754+781, 676+754+786, 676+754+797, 676+754+834, 676+754+835, 676+760+781, 676+760+786, 676+760+797, 676+760+834, 676+760+835, 676+781+786, 676+781+797, 676+781+834, 676+781+835, 676+786+797, 676+786+834, 676+786+835, 676+797+834, 676+797+835, 676+834+835, 694+698+699, 694+698+711, 694+698+754, 694+698+760, 694+698+781, 694+698+786, 694+698+797, 694+698+834, 694+698+835, 694+699+711, 694+699+754, 694+699+760, 694+699+781, 694+699+786, 694+699+797, 694+699+834, 694+699+835, 694+711+754, 694+711+760, 694+711+781, 694+711+786, 694+711+797, 694+711+834, 694+711+835, 694+754+760, 694+754+781, 694+754+786, 694+754+797, 694+754+834, 694+754+835, 694+760+781, 694+760+786, 694+760+797, 694+760+834, 694+760+835, 694+781+786, 694+781+797, 694+781+834, 694+781+835, 694+786+797, 694+786+834, 694+786+835, 694+797+834, 694+797+835, 694+834+835, 698+699+711, 698+699+754, 698+699+760, 698+699+781, 698+699+786, 698+699+797, 698+699+834, 698+699+835, 968+711+754, 698+711+760, 698+711+781, 698+711+786, 698+711+797, 698+711+834, 698+711+835, 698+754+760, 698+754+781, 698+754+786, 698+754+797, 698+754+834, 698+754+835, 698+760+781, 698+760+786, 698+760+797, 698+760+834, 698+760+835, 698+781+786, 698+781+797, 698+781+834, 698+781+835, 698+786+797, 698+786+834, 698+786+835, 698+797+834, 698+797+835, 698+834+835, 699+711+754, 699+711+760, 699+711+781, 699+711+786, 699+711+797, 699+711+834, 699+711+835, 699+754+760, 699+754+781, 699+754+786, 699+754+797, 699+754+834, 699+754+835, 699+760+781, 699+760+786, 699+760+797, 699+760+834, 699+760+835, 699+781+786, 699+781+797, 699+781+834, 699+781+835, 699+786+797, 699+786+834, 699+786+835, 699+797+834, 699+797+835, 699+834+835, 711+754+760, 711+754+781, 711+754+786, 711+754+797, 711+754+834, 711+754+835, 711+760+781, 711+760+786, 711+760+797, 711+760+834, 711+760+835, 711+781+786, 711+781+797, 711+781+834, 711+781+835, 711+786+797, 711+786+834, 711+786+835, 711+797+834, 711+797+835, 711+834+835, 754+760+781, 754+760+786, 754+760+797, 754+760+834, 754+760+835, 754+781+786, 754+781+797, 754+781+834, 754+781+835, 754+786+797, 754+786+834, 754+786+835, 754+797+834, 754+797+835, 754+834+835, 760+781+786, 60+781+797, 760+781+834, 760+781+835, 760+786+797, 760+786+834, 760+786+835, 760+797+834, 760+797+835 760+834+835, 781+786+797, 781+786+834, 781+786+835, 781+797+834, 781+797+835, 781+834+835, 786+797+834, 786+797+835, 786+834+835, and 797+834+835 of SEQ ID NO: 2.

In another aspect, a variant comprises an alteration at each position (or at least four positions) corresponding to positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2, wherein numbering is according to SEQ ID NO: 2.

In another aspect, the variant comprises or consists of an alteration at a position corresponding to position 17. In another aspect, the amino acid at a position corresponding to position 17 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution 517A of the mature polypeptide of SEQ ID NO: 2.

In another aspect, the variant comprises or consists of an alteration at a position corresponding to position 20. In another aspect, the amino acid at a position corresponding to position 20 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution F20P, F20N, F20G, or F20Y, of the mature polypeptide of SEQ ID NO: 2.

In another aspect, the variant comprises or consists of an alteration at a position corresponding to position 51. In another aspect, the amino acid at a position corresponding to position 51 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K51Q or K51H, of the mature polypeptide of SEQ ID NO: 2.

In another aspect, the variant comprises or consists of an alteration at a position corresponding to position 53. In another aspect, the amino acid at a position corresponding to position 53 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution E53P or E53Q, of the mature polypeptide of SEQ ID NO: 2.

In another aspect, the variant comprises or consists of an alteration at a position corresponding to position 55. In another aspect, the amino acid at a position corresponding to position 55 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Y55M of the mature polypeptide of SEQ ID NO: 2.

In another aspect, the variant comprises or consists of an alteration at a position corresponding to position 56. In another aspect, the amino acid at a position corresponding to position 56 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution V56M of the mature polypeptide of SEQ ID NO: 2.

In another aspect, the variant comprises or consists of an alteration at a position corresponding to position 60. In another aspect, the amino acid at a position corresponding to position 60 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Y60F of the mature polypeptide of SEQ ID NO: 2.

In another aspect, the variant comprises or consists of an alteration at a position corresponding to position 63. In another aspect, the amino acid at a position corresponding to position 63 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S63F of the mature polypeptide of SEQ ID NO: 2.

In another aspect, the variant comprises or consists of an alteration at a position corresponding to position 79. In another aspect, the amino acid at a position corresponding to position 79 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S79W of the mature polypeptide of SEQ ID NO: 2.

In another aspect, the variant comprises or consists of an alteration at a position corresponding to position 87. In another aspect, the amino acid at a position corresponding to position 87 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T87R of the mature polypeptide of SEQ ID NO: 2.

In another aspect, the variant comprises or consists of an alteration at a position corresponding to position 186. In another aspect, the amino acid at a position corresponding to position 186 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A186P of the mature polypeptide of SEQ ID NO: 2.

In another aspect, the variant comprises or consists of an alteration at a position corresponding to position 192. In another aspect, the amino acid at a position corresponding to position 192 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K192N of the mature polypeptide of SEQ ID NO: 2.

In another aspect, the variant comprises or consists of an alteration at a position corresponding to position 302. In another aspect, the amino acid at a position corresponding to position 302 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution I302D, I302V, I302M or I302H, of the mature polypeptide of SEQ ID NO: 2.

In another aspect, the variant comprises or consists of an alteration at a position corresponding to position 311. In another aspect, the amino acid at a position corresponding to position 311 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution H311N, of the mature polypeptide of SEQ ID NO: 2.

In another aspect, the variant comprises or consists of an alteration at a position corresponding to position 313. In another aspect, the amino acid at a position corresponding to position 302 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S313D of the mature polypeptide of SEQ ID NO: 2.

In another aspect, the variant comprises or consists of an alteration at a position corresponding to position 387. In another aspect, the amino acid at a position corresponding to position 387 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution I387T of the mature polypeptide of SEQ ID NO: 2.

In another aspect, the variant comprises or consists of an alteration at a position corresponding to position 388. In another aspect, the amino acid at a position corresponding to position 388 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K388R of the mature polypeptide of SEQ ID NO: 2.

In another aspect, the variant comprises or consists of an alteration at a position corresponding to position 390. In another aspect, the amino acid at a position corresponding to position 390 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K390Q of the mature polypeptide of SEQ ID NO: 2.

In another aspect, the variant comprises or consists of an alteration at a position corresponding to position 403. In another aspect, the amino acid at a position corresponding to position 403 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution I403Y of the mature polypeptide of SEQ ID NO: 2.

In another aspect, the variant comprises or consists of an alteration at a position corresponding to position 408. In another aspect, the amino acid at a position corresponding to position 408 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the alteration E408D, E408S, E408P, E408A, E408G, E408N, of the mature polypeptide of SEQ ID NO: 2.

In another aspect, the variant comprises or consists of an alteration at a position corresponding to position 410. In another aspect, the amino acid at a position corresponding to position 410 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution P410G of the mature polypeptide of SEQ ID NO: 2.

In another aspect, the variant comprises or consists of an alteration at a position corresponding to position 416. In another aspect, the amino acid at a position corresponding to position 416 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Q416S or Q416D, of the mature polypeptide of SEQ ID NO: 2.

In another aspect, the variant comprises or consists of an alteration at a position corresponding to position 448. In another aspect, the amino acid at a position corresponding to position 448 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A448E, A448S or A448W, of the mature polypeptide of SEQ ID NO: 2.

In another aspect, the variant comprises or consists of an alteration at a position corresponding to position 451. In another aspect, the amino acid at a position corresponding to position 451 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K451Q and K451S, of the mature polypeptide of SEQ ID NO: 2.

In another aspect, the variant comprises or consists of an alteration at a position corresponding to position 471. In another aspect, the amino acid at a position corresponding to position 471 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution G471S of the mature polypeptide of SEQ ID NO: 2.

In another aspect, the variant comprises or consists of an alteration at a position corresponding to position 472. In another aspect, the amino acid at a position corresponding to position 472 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S472Y of the mature polypeptide of SEQ ID NO: 2.

In another aspect, the variant comprises or consists of an alteration at a position corresponding to position 476. In another aspect, the amino acid at a position corresponding to position 476 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution D476R of the mature polypeptide of SEQ ID NO: 2.

In another aspect, the variant comprises or consists of an alteration at a position corresponding to position 489. In another aspect, the amino acid at a position corresponding to position 489 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Q489P of the mature polypeptide of SEQ ID NO: 2.

In another aspect, the variant comprises or consists of an alteration at a position corresponding to position 507. In another aspect, the amino acid at a position corresponding to position 507 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K507R of the mature polypeptide of SEQ ID NO: 2.

In another aspect, the variant comprises or consists of an alteration at a position corresponding to position 512. In another aspect, the amino acid at a position corresponding to position 512 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K512P of the mature polypeptide of SEQ ID NO: 2.

In another aspect, the variant comprises or consists of an alteration at a position corresponding to position 515. In another aspect, the amino acid at a position corresponding to position 515 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S515V of the mature polypeptide of SEQ ID NO: 2.

In another aspect, the variant comprises or consists of an alteration at a position corresponding to position 538. In another aspect, the amino acid at a position corresponding to position 538 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S538C of the mature polypeptide of SEQ ID NO: 2.

In another aspect, the variant comprises or consists of an alteration at a position corresponding to position 598. In another aspect, the amino acid at a position corresponding to position 598 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S598Q of the mature polypeptide of SEQ ID NO: 2.

In another aspect, the variant comprises or consists of an alteration at a position corresponding to position 599. In another aspect, the amino acid at a position corresponding to position 599 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A599S of the mature polypeptide of SEQ ID NO: 2.

In another aspect, the variant comprises or consists of an alteration at a position corresponding to position 602. In another aspect, the amino acid at a position corresponding to position 602 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution 1602T or 1602D, of the mature polypeptide of SEQ ID NO: 2.

In another aspect, the variant comprises or consists of an alteration at a position corresponding to position 603. In another aspect, the amino acid at a position corresponding to position 603 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution V603P of the mature polypeptide of SEQ ID NO: 2.

In another aspect, the variant comprises or consists of an alteration at a position corresponding to position 605. In another aspect, the amino acid at a position corresponding to position 605 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution 5605T of the mature polypeptide of SEQ ID NO: 2.

In another aspect, the variant comprises or consists of an alteration at a position corresponding to position 609. In another aspect, the amino acid at a position corresponding to position 609 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution G609E of the mature polypeptide of SEQ ID NO: 2.

In another aspect, the variant comprises or consists of an alteration at a position corresponding to position 676. In another aspect, the amino acid at a position corresponding to position 676 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution D676H of the mature polypeptide of SEQ ID NO: 2.

In another aspect, the variant comprises or consists of an alteration at a position corresponding to position 688. In another aspect, the amino acid at a position corresponding to position 688 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A688G of the mature polypeptide of SEQ ID NO: 2.

In another aspect, the variant comprises or consists of an alteration at a position corresponding to position 690. In another aspect, the amino acid at a position corresponding to position 690 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Y690F of the mature polypeptide of SEQ ID NO: 2.

In another aspect, the variant comprises or consists of an alteration at a position corresponding to position 694. In another aspect, the amino acid at a position corresponding to position 694 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T694A of the mature polypeptide of SEQ ID NO: 2.

In another aspect, the variant comprises or consists of an alteration at a position corresponding to position 697. In another aspect, the amino acid at a position corresponding to position 697 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T697G of the mature polypeptide of SEQ ID NO: 2.

In another aspect, the variant comprises or consists of an alteration at a position corresponding to position 698. In another aspect, the amino acid at a position corresponding to position 698 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution R698W of the mature polypeptide of SEQ ID NO: 2.

In another aspect, the variant comprises or consists of an alteration at a position corresponding to position 699. In another aspect, the amino acid at a position corresponding to position 699 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T699A of the mature polypeptide of SEQ ID NO: 2.

In another aspect, the variant comprises or consists of an alteration at a position corresponding to position 711. In another aspect, the amino acid at a position corresponding to position 711 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T711V or T711T, of the mature polypeptide of SEQ ID NO: 2.

In another aspect, the variant comprises or consists of an alteration at a position corresponding to position 719. In another aspect, the amino acid at a position corresponding to position 719 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution W719R of the mature polypeptide of SEQ ID NO: 2.

In another aspect, the variant comprises or consists of an alteration at a position corresponding to position 754. In another aspect, the amino acid at a position corresponding to position 754 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K754R of the mature polypeptide of SEQ ID NO: 2.

In another aspect, the variant comprises or consists of an alteration at a position corresponding to position 756. In another aspect, the amino acid at a position corresponding to position 756 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution V756H or V756Y of the mature polypeptide of SEQ ID NO: 2.

In another aspect, the variant comprises or consists of an alteration at a position corresponding to position 760. In another aspect, the amino acid at a position corresponding to position 760 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S760G of the mature polypeptide of SEQ ID NO: 2.

In another aspect, the variant comprises or consists of an alteration at a position corresponding to position 781. In another aspect, the amino acid at a position corresponding to position 781 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T781M of the mature polypeptide of SEQ ID NO: 2.

In another aspect, the variant comprises or consists of an alteration at a position corresponding to position 786. In another aspect, the amino acid at a position corresponding to position 786 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution N786K of the mature polypeptide of SEQ ID NO: 2.

In another aspect, the variant comprises or consists of an alteration at a position corresponding to position 797. In another aspect, the amino acid at a position corresponding to position 797 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T797S of the mature polypeptide of SEQ ID NO: 2.

In another aspect, the variant comprises or consists of an alteration at a position corresponding to position 824. In another aspect, the amino acid at a position corresponding to position 824 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A824D of the mature polypeptide of SEQ ID NO: 2.

In another aspect, the variant comprises or consists of an alteration at a position corresponding to position 833. In another aspect, the amino acid at a position corresponding to position 833 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution N833D of the mature polypeptide of SEQ ID NO: 2.

In another aspect, the variant comprises or consists of an alteration at a position corresponding to position 834. In another aspect, the amino acid at a position corresponding to position 834 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Q834E of the mature polypeptide of SEQ ID NO: 2.

In another aspect, the variant comprises or consists of an alteration at a position corresponding to position 835. In another aspect, the amino acid at a position corresponding to position 835 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S835D of the mature polypeptide of SEQ ID NO: 2.

In another aspect, the variant comprises or consists of an alteration at a position corresponding to position 1048. In another aspect, the amino acid at a position corresponding to position 1048 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution F1048W of the mature polypeptide of SEQ ID NO: 2.

In one embodiment, the endoglucanase variant comprised in the detergent compositions may further comprise an alteration at one or more positions selected from the group consisting of alterations in positions:
216, 283, 346, 559, 564, 579, 636, 638, 651, 824, 848, 869, 880, 881, 883, 887, 892, 905, 906, 912, 921, 928, 934, 937, 948, 956, 999 and 1037, or corresponding to those positions.

More specifically the endoglucanase variant comprised in the detergent compositions may further comprise one or more alterations at one or more positions selected from the group consisting of: N216D, N216Q, A283D, A346D, A559P, A559N, A564E, Y579W, S636K, S636N, F638N, A651P, A824D, N848D, A869V, R880K, V881T, V881Q, T883R, T887K, T892P, N905D, F906A, A912V, K921R, S928D, Y934G, A937E, K948R, Q956Y, T999R, and A1037E, or corresponding to those positions.

In another aspect, the variant comprises or consists of an alteration at a position corresponding to position selected from the group consisting of alterations in positions: 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 834, 833, 835 and 1048 of SEQ ID NO: 2, wherein numbering is according to SEQ ID NO: 2.

In another aspect, the amino acid at a position corresponding to any of positions as described above is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution selected from the group consisting of: 517A, F20P, F20N, F20G, F20Y, K51Q, K51H, E53P, E53G, Y55M, V56M, Y60F, S63F, T87R, A186P, K192N, I302D, I302H, I302V, I302M, H311N, S313D, I387T, K388R, K390Q, 1403Y, E408D, E408S, E408P, E408A, E408G, E408N, P410G, Q416S, Q416D, A448E, A448W, A448S, K451S, G471S, S472Y, D476R, Q489P, K507R, K512P, S515V, S538C, Y579W, S598Q, A599S, 1602T, 1602D, V603P, 5605T, G609E, D676H, A688G, Y690F, T694A, T697G, R698W, T699A, T711V, T711Y, W719R, K754R, V756H, V756Y, 5760G, T781M, N786K, T797S, A824D, N833D, Q834E, S835D and F1048W, wherein numbering is according to SEQ ID NO: 2.

In a particular embodiment, a detergent composition may include an endoglucanase variant selected from the group consisting of the endoglucananase variants set forth in Table 2 herein.

In a particular embodiment, a detergent composition may include an endoglucananase variant selected from the group consisting of the endoglucananase variants set forth in Table 3 herein.

In a particular embodiment, a detergent composition may include an endoglucananase variant selected from the group consisting of the endoglucananase variants set forth in Table 4 herein.

In a particular embodiment, a detergent composition may include an endoglucananase variant selected from the group consisting of the endoglucananase variants set forth in Table 5 herein.

In a particular embodiment, a detergent composition may include an endoglucananase variant selected from the group consisting of the endoglucananase variants set forth in Table 6 herein.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and aspara-gine), hydrophobic amino acids (leucine, isoleucine and valine), aromatic amino acids (phenylalanine, tryp-tophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for xanthan lyase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In one embodiment, a detergent composition may include an endoglucanase variant, having the total number of alterations compared to SEQ ID NO: 2 between 1 and 20, e.g., between 1 and 10 or between 1 and 5, such as 1, 2, 3, 4, 5, 6, 7, 8, 9 or 10 alterations.

In one embodiment, a detergent composition may include an endoglucanase variant, wherein an activity on xanthan gum pre-treated with xanthan lyase is a xanthan degrading activity, said xanthan degrading activity is endoglucanase EC 3.2.1.4 activity.

In an embodiment, the variant has an improved stability in a detergent composition compared to a parent enzyme (e.g., SEQ ID NO: 2).

In one embodiment, a detergent composition may include an endoglucanase variant, wherein said variant has an improved stability in a detergent composition compared to a parent endoglucanase (e.g., with SEQ ID NO: 2).

In one embodiment, a detergent composition may include an endoglucanase variant, wherein said variant has a half-life improvement factor (HIF)≥1.0; said variant has a half-life improvement factor (HIF)>1.0 relative to a parent endoglucanase, e.g. an endoglucanase of SEQ ID NO: 2. A way of calculating said half-life improvement factor (HIF) is described in example 3 herein. Accordingly, residual activity (RA) can be calculated using the following formula:

$$RA(\%) = \frac{Abs(Stress)}{Abs(Ref)} \times 100\%$$

wherein Abs(Stress) is the absorbance at 405 nm of the sample in the stress microtiter plate (MTP) (e.g. incubated at 25° C. over-night or any other combination of temperature and time) after subtracting relevant background absorbance contributions, Abs(Ref) is the absorbance at 405 nm of the sample in the reference MTP (e.g. incubated at 5° C. over-night) after subtracting relevant background absorbance contributions, wherein half-lives for the degradation of each variant and parent endoglucanase (e.g. at 25° C.) are calculated using the following formula:

$$T1/2 = -\frac{\ln(2) \times T}{\ln\left(\frac{Abs(Stress)}{Abs(Ref)}\right)}$$

wherein T is the incubation time for both the stress and reference MTP, wherein half-life-improvement factors (HIFs) are calculated using the following formula:

$$HIF = \frac{T1/2, \text{variant}}{T1/2, wt}$$

e.g. wherein T1/2 wt (or wild type) is the T1/2 of the mature parent endoglucanase with SEQ ID NO: 2.

In one embodiment, a detergent composition may include an endoglucanase variant, wherein a half-life improvement factor (HIF) is determined after incubation of said endoglucanase variant in a detergent composition at 25° C. for a time period from about 17 to about 20 hours.

Parent

The parent endoglucanase may be (a) a polypeptide having at least 60% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, or (ii) the full-length complement of (i); or (c) a polypeptide encoded by a polynucleotide having at least 60% sequence identity to the mature polypeptide coding sequence of SEQ ID NO: 1.

In an aspect, the parent has a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xanthan lyase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2. In another aspect, the parent is a fragment of the mature polypeptide of SEQ ID NO: 2 containing at least 85%, 86%, 87%, 88%, 89%, 90%, 91%, 92%, 93%, 94% or 95% of the number of amino acids of SEQ ID NO: 2. In another embodiment, the parent is an allelic variant of the mature polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, New York).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. In a non-limiting embodiment, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin).

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

Hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length com-element thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide. A fusion polypeptide is produced by fusing a polynucleotide encoding another polypeptide to a polynucleotide. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes herein, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial enzyme. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* enzyme, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* enzyme.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* enzyme.

In another aspect, the parent is a *Streptococcus equisimilis, Streptococcus pyogenes, Streptococcus uberis*, or *Streptococcus equi* subsp. *zooepidemicus* enzyme.

In another aspect, the parent is a *Streptomyces achromogenes, Streptomyces avermitilis, Streptomyces coelicolor, Streptomyces griseus*, or *Streptomyces lividans* enzyme.

The parent may be a fungal enzyme. For example, the parent may be a yeast enzyme such as a *Candida, Kluyveromyces, Pichia, Saccharomyces, Schizosaccharomyces*, or *Yarrowia* enzyme; or a filamentous fungal enzyme such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosparia, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor,*

Schizophyllum, Scytalidium, Talaromyces, Thermoascus, Thielavia, Tolypocladium, Trichoderma, Trichophaea, Verticillium, Volvariella, or Xylaria enzyme.

In another aspect, the parent is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis enzyme.

In another aspect, the parent is an Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei, or Trichoderma viride enzyme.

In another aspect, the parent is a Paenibacillus sp. xanthan lyase, e.g., the xanthan lyase of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

Methods for obtaining a variant having endoglucanase activity, may comprise: (a) introducing into a parent endoglucanase an alteration at one or more (e.g., several) positions corresponding to positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2 of the mature polypeptide of SEQ ID NO: 2, wherein the variant has endoglucanase activity; and (b) recovering the variant.

In an embodiment, the variant to be obtained may further comprise an alteration at one or more positions corresponding to positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999 and 1037 of SEQ ID NO: 2 of the mature polypeptide of SEQ ID NO: 2, wherein the variant has endoglucanase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microflu-idic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Embodiments

In one embodiment, to a detergent composition may include at least one (e.g. 1, 2, 3, 4, 5, 6, 7, 8, 9 or 10) endoglucanase variant.

In one embodiment, a detergent composition may include at least one (e.g. 1, 2, 3, 4, 5, 6, 7, 8, 9 or 10) endoglucanase variant, further comprising one or more detergent components.

In one embodiment, a detergent composition may include at least one (e.g. 1, 2, 3, 4, 5, 6, 7, 8, 9 or 10) endoglucanase variant, further comprising one or more additional enzymes selected from the group consisting of: xanthan lyases, proteases, amylases, lichenases, lipases, cutinases, cellulases, endoglucanases, xyloglucanases, pectinases, pectin lyases, xanthanases, peroxidases, haloperoxygenases, catalases and mannanases, or any mixture thereof.

In one embodiment, a detergent composition may include at least one (e.g. 1, 2, 3, 4, 5, 6, 7, 8, 9 or 10) endoglucanase variant, further comprising one or more detergent components and one or more additional enzymes selected from the group consisting of: xanthan lyases, proteases, amylases, lichenases, lipases, cutinases, cellulases, endoglucanases, xyloglucanases, pectinases, pectin lyases, xanthanases, peroxidases, haloperoxygenases, catalases and mannanases, or any mixture thereof.

In one embodiment, a detergent composition may include at least one (e.g. 1, 2, 3, 4, 5, 6, 7, 8, 9 or 10) endoglucanase variant, further comprising one or more detergent components, wherein said detergent composition is in form of a bar, a homogenous tablet, a tablet having two or more layers, a pouch having one or more compartments, a regular or compact powder, a granule, a paste, a gel, or a regular, compact or concentrated liquid.

In one embodiment, a detergent composition, may be used for degrading xanthan gum and use in a cleaning process, such as laundry or hard surface cleaning such as dish wash.

In one embodiment, a detergent composition may have an enzyme detergency benefit In one embodiment, a method for degrading xanthan gum may include: applying a detergent composition to a xanthan gum.

In one embodiment, a method for degrading xanthan gum may include: applying a detergent composition to a xanthan gum, wherein said xanthan gum is on the surface of a textile or hard surface, such as dish wash.

Polynucleotides

Also disclosed herein are isolated polynucleotides encoding a variant. Accordingly, in one aspect, the present disclosure relates to isolated polynucleotides encoding a variant comprising an alteration at one or more positions in a region selected from the group consisting of: i) region 10 corresponding to amino acids 1 to 94 of SEQ ID NO: 2, ii) region 11 corresponding to amino acids 106 to 114 of SEQ ID NO: 2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleo-tide-based amplification (NASBA) may be used. The polynucleotides may be cloned in a strain of *Bacillus subtilis* or *E. coli*, or a related organism and thus, for example, may be an allelic or species variant of the polypeptide encoding region of the polynucleotide.

Modification of a polynucleotide encoding a polypeptide may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, Ford et al., (1991), '*Protein Expression and Purification*', 2: 95-107.

Nucleic Acid Constructs

Also disclosed herein are nucleic acid constructs comprising a polynucleotide encoding a variant as described herein operably linked to one or more control sequences that direct the expression of the coding sequence in a suitable host cell under conditions compatible with the control sequences. Accordingly, disclosed are nucleic acid constructs comprising a polynucleotide encoding a variant comprising an alteration at one or more positions in a region selected from the group consisting of: i) region 10 corresponding to amino acids 1 to 94 of SEQ ID NO: 2, ii) region 11 corresponding to amino acids 106 to 114 of SEQ ID NO:

2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2, operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used.

Non-limiting terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Non-limiting terminators for filamentous fungal host cells are obtained from the genes for *Aspergillus nidulans* anthranilate synthase, *Aspergillus niger* glucoamylase, *Aspergillus niger* alpha-glucosidase, Aspergillus *oryzae* TAKA amylase, and *Fusarium oxysporum* trypsin-like protease.

Non-limiting terminators for yeast host cells are obtained from the genes for *Saccharomyces cerevisiae* enolase, *Saccharomyces cerevisiae* cytochrome C (CYC1), and *Saccharomyces cerevisiae* glyceralde-hyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Non-limiting leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Non-limiting polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus* stearothermophilus neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (npr7), *Myceliophthora thermophile* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

Disclosed herein are recombinant expression vectors comprising a polynucleotide encoding a variant as described herein, a promoter, and transcriptional and translational stop signals. Accordingly, the present disclosure relates to recombinant expression vectors comprising a polynucleotide encoding a variant comprising an alteration at one or more positions in a region selected from the group consisting of: i) region 10 corresponding to amino acids 1 to 94 of SEQ ID NO: 2, ii) region 11 corresponding to amino acids 106 to 114 of SEQ ID NO: 2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2, a promoter, and transcriptional and translational stop signals.

The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof *Aspergillus nidulans* or *Aspergillus oryzae* amdS and pyrG genes and a *Streptomyces hygroscopicus* bar gene may be used in an *Aspergillus* cell.

The vector contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAIV1111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Further disclosed are recombinant host cells, comprising a polynucleotide encoding a variant as described herein operably linked to one or more control sequences that direct the production of a variant. Accordingly, in one aspect, the present disclosure relates to recombinant host cells, comprising a polynucleotide encoding a variant comprising an alteration at one or more positions in a region selected from the group consisting of: i) region 10 corresponding to amino acids 1 to 94 of SEQ ID NO: 2, ii) region 11 corresponding to amino acids 106 to 114 of SEQ ID NO: 2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2, operably linked to one or more control sequences that direct the production of a variant comprising an alteration at one or more positions in a selected from the group consisting of: i) region 10 corresponding to amino acids 1 to 94 of SEQ ID NO: 2, ii) region 11 corresponding to amino acids 106 to 114 of SEQ ID NO: 2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2.

A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla *Ascomycota, Basidiomycots, Chytridiomycota*, and *Zygomycota* as well as the *Oomycota* and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, yeast shall be defined as described in Biology and Activities of Yeast (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by bud-ding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora* crassa, *Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

Also disclosed are methods of producing (e.g., in vitro or ex vivo methods) a variant, comprising: (a) cultivating a host cell under conditions suitable for expression of the variant; and (b) recovering the variant. Accordingly, in one aspect, the present disclosure relates to methods of producing (e.g. in vitro or ex vivo methods) a variant comprising an alteration at one or more positions in a region selected from the group consisting of: i) region 10 corresponding to amino acids 1 to 94 of SEQ ID NO: 2, ii) region 11 corresponding to amino acids 106 to 114 of SEQ ID NO: 2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2, the method comprising cultivating a host cell comprising a polynucleotide encoding the variant, under conditions suitable for expression of the variant; and (b) optionally, recovering the variant.

Further disclosed are methods of producing (e.g., in vitro or ex vivo methods) a variant as described herein, comprising (a) cultivating a cell, which in its wild-type form produces the polypeptide, under conditions conducive for production of the polypeptide; and (b) recovering the polypeptide. In an aspect, the cell is a *Paenibacillus* cell, or a *Microbacterium* cell.

Also disclosed are methods of producing (e.g., in vitro or ex vivo methods) a variant as described herein, comprising (a) cultivating a recombinant host cell under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid-state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The variant polypeptide may be detected using methods known in the art that are specific for the polypeptides such as methods for determining cellulose or xanthan lyase activity. These detection methods include, but are not limited to, use of specific antibodies, formation of an enzyme product, or disappearance of an enzyme substrate. For example, an enzyme assay may be used to determine the activity of the polypeptide.

The variant polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The variant polypeptide may be purified by a variety of procedures known in the art including, but not limited to, chromatography (e.g., ion exchange, affinity, hydrophobic, chromatofocusing, and size exclu-sion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the variant polypeptide is not recovered, but rather a host cell expressing the polypeptide is used as a source of the variant polypeptide.

Corn positions

In one certain aspect, the variants have improved stability in detergents compared to a parent enzyme or compared to an endoglucanase having the identical amino acid sequence of the variant, but not having an alteration (e.g., a substitution, deletion or insertion) at one or more of the specified positions or compared to the endoglucanase with SEQ ID NO: 2, wherein activity and/or stability in detergent is measured as disclosed in example 3 herein. Thus, in one embodiment, detergent compositions may include a variant comprising an alteration at one or more positions in a region selected from the group consisting of: i) region 10 corresponding to amino acids 1 to 94 of SEQ ID NO: 2, ii) region 11 corresponding to amino acids 106 to 114 of SEQ ID NO: 2, iii) region 12 corresponding to amino acids 139 to 209 of SEQ ID NO: 2, iv) region 13 corresponding to amino acids 252 to 266 of SEQ ID NO: 2, v) region 14 corresponding to amino acids 302 to 338 of SEQ ID NO: 2, vi) region 15 corresponding to amino acids 362 to 546 of SEQ ID NO: 2, vii) region 16 corresponding to amino acids 596 to 611 of SEQ ID NO: 2, viii) region 17 corresponding to amino acids 661 to 805 of SEQ ID NO: 2, ix) region 18 corresponding to amino acids 829 to 838 of SEQ ID NO: 2, and x) region 19 corresponding to amino acids 1043 to 1055 of SEQ ID NO: 2, wherein said variant has at least 60% and less than 100% sequence identity to SEQ ID NO: 2.

Besides enzymes the detergent compositions may comprise additional components. The choice of additional components is within the skill of the artisan and includes conventional ingredients, including the exemplary non-limiting components set forth below. The choice of components may include, for fabric care, the consider-ation of the type of fabric to be cleaned, the type and/or degree of soiling, the temperature at which cleaning is to take place, and the formulation of the detergent product. Although components mentioned below are cate-gorized by general header according to a particular functionality, this is not to be construed as a limitation, as a component may comprise additional functionalities as will be appreciated by the skilled artisan.

The detergent composition may be suitable for the laundering of textiles such as e.g. fabrics, cloths or linen, or for cleaning hard surfaces such as e.g. floors, tables, or dish wash.

Detergent Compositions

In one embodiment, a variant as described herein may be added to a detergent composition in an amount corresponding to 0.0001-200 mg of enzyme protein, such as 0.0005-100 mg of enzyme protein, such as 0.001-30 mg of enzyme protein, alternatively 0.005-8 mg of enzyme protein, or 0.01-2 mg of enzyme protein per litre of wash liquor.

A composition for use in automatic dishwash (ADW), for example, may comprise 0.0001%-50%, such as 0.001%-20%, such as 0.01%-10%, such as 0.05-5% of enzyme protein by weight of the composition.

A composition for use in laundry granulation or a solid/granular laundry composition in general, for example, may comprise 0.0001%-50%, such as 0.001%-20%, such as 0.01%-10%, such as 0.05%-5% of enzyme protein by weight of the composition.

A composition for use in laundry liquid, for example, may comprise 0.0001%-10%, such as 0.001-7%, such as 0.1%-5% of enzyme protein by weight of the composition.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments.

A polypeptide may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more non-ionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually comprise from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually comprise from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually comprise from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propox-ylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), al-kylpolyglycosides (APG), alkoxylated amines, fatty acid monoethanolamides (FAM), fatty acid diethanola-mides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glu-camides, GA, or fatty acid glucamide, FAGA), as well as products available under the trade names SPAN and TWEEN, and combinations thereof.

When included therein the detergent will usually comprise from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxy-ethyl)amine oxide, fatty acid alkanolamides and ethoxylated fatty acid alkanolamides, and combinations thereof.

When included therein the detergent will usually comprise from about 0% to about 10% by weight of a zwitterionic surfactant. Non-limiting examples of zwitterionic surfactants include betaine, alkyldimethylbeta-ine, sulfobetaine, and combinations thereof.

Hydrotropes

A hydrotrope is a compound that solubilises hydrophobic compounds in aqueous solutions (or oppo-sitely, polar substances in a non-polar environment). Typically, hydrotropes have both hydrophilic and a hydrophobic character (so-called amphiphilic properties as known from surfactants); however, the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming micel-lar, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may comprise 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may comprise about 0-65% by weight, such as about 5% to about 45% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyro-phosphates), triphosphates such as sodium triphosphate (STP or STPP), carbonates such as sodium car-bonate, soluble silicates such as sodium meta-silicate, layered silicates (e.g., SKS-6 from Hoechst), ethanolamines such as 2-aminoethan-1-ol (MEA), dietha-nolamine (DEA, also known as iminodiethanol), triethanolamine (TEA, also known as 2,2',2"-nitrilotriethanol), and carboxymethyl inulin (CMI), and combinations thereof.

The detergent composition may also comprise 0-20% by weight, such as about 5% to about 10%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocar-boxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetri-aminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphos-phonic acid (HEDP), ethylenediaminetetra-(methylenephosphonic acid) (EDTMPA), diethylenetriamine-pentakis(methylenephosphonic acid) (DTPMPA or DTMPA), N-(2-hydroxyethyl) iminodiacetic acid (EDG), aspartic acid-N-monoacetic acid (ASMA), aspartic acid-N,N-diacetic acid (ASDA), aspartic acid-N-mono-propionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGO, N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)-ethylidenediamine-N,N; N'-triacetate (HEDTA), diethanolgly-cine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may comprise 0-50% by weight, such as about 0.1% to about 25%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy) benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO98/17767. A particular family of bleach activators of interest was disclosed in EP624154 and in that family is acetyl triethyl citrate (ATC). ATC or a short chain triglyceride like triacetin has the advantage that it is environmental friendly as it eventually degrades into citric acid and alcohol. Furthermore, acetyl triethyl citrate and triacetin has a good hydrolytical stability in the product upon storage and it is an efficient bleach activator. Finally, ATC provides a good building capacity to the laundry additive. Alternatively, the bleaching system may comprise peroxy-acids of, for example, the amide, imide, or sulfone type. The bleaching system may also comprise peracids such as 6-(phthalimido) peroxyhexanoic acid (PAP). The bleaching system may also include a bleach catalyst. In some embodiments the bleach component may be an organic catalyst selected from the group consisting of organic catalysts having the following formulae:

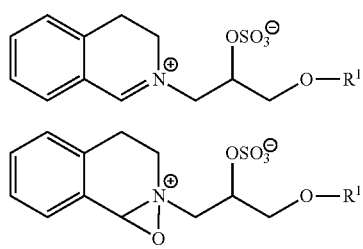

(iii) and mixtures thereof; wherein each $R^1$ is independently a branched alkyl group containing from 9 to 24 carbons or linear alkyl group containing from 11 to 24 carbons, or each $R^1$ is independently a branched alkyl group containing from 9 to 18 carbons or linear alkyl group containing from 11 to 18 carbons, or each $R^1$ is independently selected from the group consisting of 2-propylheptyl, 2-butyloctyl, 2-pentylnonyl, 2-hex-yldecyl, n-dodecyl, n-tetradecyl, n-hexadecyl, n-octadecyl, iso-nonyl, iso-decyl, iso-tridecyl and iso-penta-decyl. Other exemplary bleaching systems are described, e.g. in WO2007/087258, WO2007/087244, WO2007/087259 and WO2007/087242. Suitable photobleaches may for example be sulfonated zinc phthalocyanine.

Polymers

The detergent may comprise 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide anti-redeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(eth-yleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid co-polymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrol-idone-vinylimidazole (PVPVI). Further exemplary polymers include sulfonated polycarboxylates, polyeth-ylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions may also comprise fabric hueing agents such as dyes or pigments, which when formulated in detergent compositions can deposit onto a fabric when said fabric is contacted with a wash liquor comprising said detergent compositions and thus altering the tint of said fabric through absorp-tion/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent when the composition is in the form of a unit dose pouch. Suitable hueing agents are also disclosed in, e.g. WO 2007/087257 and WO2007/087243.

Additional Enzymes

The detergent additive as well as the detergent composition may comprise one or more [additional] enzymes such as a xanthan lyase, protease, lipase, cutinase, an amylase, lichenase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (La, pH-optimum, compatibility with other enzymatic and non-enzymatic ingredients, etc.), and the en-zyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, U.S. Pat. Nos. 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially variants thereof having substitution, insertion and/or deletion at one or more of the positions corresponding to the following positions in SEQ ID NO: 8 of WO 02/099091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, such as P19A, G20K, Q44K, N48E, Q119H or Q146 R.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases

The additional enzyme may be another protease or protease variant. The protease may be of animal, vegetable or microbial origin, including chemically or genetically modified mutants. Microbial origin may be used. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4, M5, M7 or M8.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one aspect the protease may be a subtilase, such as a subtilisin or a variant hereof. Further the subtilases (and the serine proteases) are characterised by having two active site amino acid residues apart from the serine, namely a histidine and an aspartic acid residue.

Examples of subtilisins are those derived from *Bacillus* such as subtilisin *lentus, Bacillus lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. An example of a subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. The subtilase variants may comprise the mutations: S3T, V41, S9R, A15T, K27R, *36D, V68A, N76D, N87S,R, *97E, A98S, S99G,D,A, S99AD, S101G,M,R S103A, V1041,Y,N, S106A, G118V,R, H120D,N, N123S, S128L, P129Q, S130A, G160D, Y167A, R170S, A194P, G195E, V199M, V2051, L217D, N218D, M222S, A232V, K235L, Q236H, Q245R, N252K, T274A (using BPN' numbering). A further protease is the alkaline protease from *Bacillus lentus* DSM 5483, as described for example in WO 95/23221, and variants thereof which are described in WO 92/21760, WO 95/23221, EP 1921147 and EP 1921148.

Examples of trypsin-like proteases are trypsin (e.g. of porcine or bovine origin) and the *Fusarium* protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044993.

Non-limiting commercially available protease enzymes include Alcalase™, Coronase™, Duralase™ Durazym™, Esperase™, Everlase™, Kannase™, Liquanase™, Liquanase Ultra™, Ovozyme™, Polarzyme™, Primase™, Relase™, Savinase™ and Savinase Ultra™, (Novozymes A/S), Axapem™ (Gist-Brocases N.V.), BLAP and BLAP X (Henkel AG & Co. KGaA), Excellase™, FN2™, FN3™, FN4™, Maxaca™, Maxapem™, Maxatase™, Properase™, Purafast™, PurafectlM, Purafect OxP™, Purafect Prime™ and Puramax™ (Genencor int.).

Lipases and Cutinases

Suitable lipases and cutinases include those of bacterial or fungal origin. Chemically modified or protein engineered mutant enzymes are included. Examples include lipase from *Thermomyces*, e.g. from T. lanu-ginosus (previously named *Humicola lanuginosa*) as described in EP258068 and EP305216, cutinase from *Humicola*, e.g. *H. insolens* (WO96/13580), lipase from strains of *Pseudomonas* (some of these now re-named to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from Thermobifida fusca (WO11/084412), Geobacillus stearothermophilus lipase (WO11/084417), lipase from *Bacillus subtilis* (WO11/084599), and lipase from *Streptomyces griseus* (WO11/150157) and *S. pristinaespiralis* (WO12/137147).

Further examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Non-limiting commercial lipase products include Lipolase™, Lipex™; Lipolex™ and Lipoclean™ (Novozymes A/S), Lumafast (originally from Genencor) and Lipomax (originally from Gist-Brocades).

Amylases

The amylase may be an alpha-amylase, a beta-amylase or a glucoamylase and may be of bacterial or fungal origin.

Chemically modified or protein engineered mutants are included. Amylases include, for example, alpha-amylases obtained from *Bacillus*, e.g., a special strain of *Bacillus licheniformis*, described in more detail in GB 1,296,839.

Examples of amylases are those having SEQ ID NO: 3 in WO 95/10603 or variants having 90% sequence identity to SEQ ID NO: 3 thereof. Non-limiting variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 of SEQ ID NO: 3 in WO 95/10603.

Other amylases are variants of SEQ ID NO: 1 of WO 2016/203064 having at least 75% sequence identity to SEQ ID NO: 1 thereof. Non-limiting variants are variants comprising a modification in one or more positions corresponding to positions 1, 54, 56, 72, 109, 113, 116, 134, 140, 159, 167, 169, 172, 173, 174, 181, 182, 183, 184, 189, 194, 195, 206, 255, 260, 262, 265, 284, 289, 304, 305, 347, 391, 395, 439, 469, 444, 473, 476, or 477 of SEQ ID NO: 1, wherein said alpha-amylase variant has a sequence identity of at least 75% but less than 100% to SEQ ID NO: 1.

Further amylases which can be used are amylases having SEQ ID NO: 6 in WO 02/010355 or variants thereof having 90% sequence identity to SEQ ID NO: 6. Non-limiting variants of SEQ ID NO: 6 are those having a deletion in positions 181 and 182 and a substitution in position 193.

Other amylase examples are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Non-limiting variants of this hybrid alpha-amylase are those having a substitution, a deletion or an insertion in one of more of the following positions: G48, T49, G107, H156, A181, N190, M197, 1201, A209 and Q264. Variants of the hybrid alpha-amylase may include residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48+T49+G107+H156+A181+N190+1201+A209+Q264.

Further amylase examples are amylases having SEQ ID NO: 6 in WO 99/019467 or variants thereof having 90% sequence identity to SEQ ID NO: 6. Non-limiting variants of SEQ ID NO: 6 are those having a substitution, a deletion or an insertion in one or more of the following positions: R181, G182, H183, G184, N195, 1206, E212, E216 and K269. Non-limiting amylases are those having deletion in positions G182 and H183 or positions H183 and G184.

Additional amylases are those having SEQ ID NO: 1, SEQ ID NO: 2 or SEQ ID NO: 7 of WO 96/023873 or variants thereof having 90% sequence identity to SEQ ID NO: 1, SEQ ID NO: 2 or SEQ ID NO: 7. Non-limiting variants of SEQ ID NO: 1, SEQ ID NO: 2 or SEQ ID NO: 7 are those having a substitution, a deletion or an insertion in one or more of the following positions: 140, 181, 182, 183, 184, 195, 206, 212, 243, 260, 269, 304 and 476. Non-limiting variants are those having a deletion in positions 182 and 183 or positions 183 and 184. Non-limiting amylase variants of SEQ ID NO: 1, SEQ ID NO: 2 or SEQ ID NO: 7 are those having a deletion in positions 183 and 184 and a substitution in positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Non-limiting variants of SEQ ID NO: 10 in WO 01/66712 are those having a substitution, a deletion or an insertion in one of more of the following positions: 176, 177, 178, 179, 190, 201, 207, 211 and 264.

Further amylases which can be used are amylases having SEQ ID NO: 2 of WO 09/061380 or variants thereof having 90% sequence identity to SEQ ID NO: 2. Non-limiting variants of SEQ ID NO: 2 are those having a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. Non-limiting variants of SEQ ID NO: 2 are those having the substitution in one of more of the following positions: Q87E,R, Q98R, S125A, N128C, T131I , T165I, K178L, T182G, M201L, F202Y, N225E,R, N272E,R, S243Q,A,E, D, Y305R, R309A, Q320R, Q359E, K444E and G475K and/or deletion in position R180 and/or S181. Non-limiting amylase variants of SEQ ID NO: 2 are those having the substitutions: N128C+K178L+T182G+Y305R+G475K; N1280+K178L+T182G+F202Y+Y305R+D319T+G475K; S125A+N1280+K178L+T182G+Y305R+G475K; or S125A+N128C+T131I+T165I+K178L+T182G+Y305R+G475K wherein the variant optionally further comprises a substitution at position 243 and/or a deletion at position 180 and/or position 181.

Other examples of amylases are the alpha-amylase having SEQ ID NO: 12 in WO01/66712 or a variant having at least 90%, such as at least 95%, sequence identity to SEQ ID NO: 12. Non-limiting amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Non-limiting amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, non-limiting a variant that additionally has substitutions in all these positions.

Commercially available amylases are Duramyl™, Termamyl™, Fungamyl™, Stainzyme™, Stainzyme Plus™, Natalase™ and BAN™ (Novozymes A/S), Rapidase™ and Purastar™ (from Genencor International Inc.).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive, i.e., a separate additive or a combined additive, can be formulated, for example, as a granulate, liquid, slurry, etc. Non-limiting detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants:

The detergent compositions can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents:

The detergent compositions may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent:

The detergent compositions will also contain additional components that may tint articles being cleaned, such as fluorescent whitening agent or optical brighteners. Where present the brightener is at a level of about 0,01% to about 0,5%. Any fluorescent whitening agent suitable for use in a laundry detergent composimine may be used in the composition. The most commonly used fluorescent whitening agents are those belonging to the classes of diaminostilbene-sulphonic acid derivatives, diarylpy-razoline derivatives and bisphenyl-distyryl derivatives. Examples of the diaminostilbene-sulphonic acid derivative type of fluorescent whitening agents include the sodium salts of: 4,4'-bis-(2-diethanolamino-4-ani-lino-s-triazin-6-ylamino)-stilbene-2,2'-disulphonate; 4,4'-bis-(2,4-dianilino-s-triazin-6-ylamino)-stilbene-2,2'-disulphonate; 4,4'-bis-(2-anilino-4(N-methyl-N-2-hydroxy-ethylamino)-s-triazin-6-ylamino)-stilbene-2, 2'-disulphonate, 4,4'-bis-(4-phenyl-2,1,3-triazol-2-yl)-stilbene-2,2'-disulphonate; 4,4'-bis-(2-anilino-4-(1-methyl-2-hydroxy-ethylamino)-s-triazin-6-ylamino)-stilbene-2,2'-disulphonate and 2-(stilbyl-4"-naptho-1,2':4,5)-1,2,3-trizole-2"-sulphonate. Non-limiting fluorescent whitening agents are Tinopal DMS and Tinopal CBS available from Ciba-Geigy AG, Basel, Switzerland. Tinopal DMS is the disodium salt of 4,4'-bis-(2-morpho-lino-4 anilino-s-triazin-6-ylamino)-stilbene disulphonate. Tinopal CBS is the disodium salt of 2,2'-bis-(phenyl-styryl) disulphonate. Also usable are fluorescent whitening agents is the commercially available Parawhite KX, supplied by Paramount Minerals and Chemicals, Mumbai, India. Other fluorescers suitable for use include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers:

The detergent compositions may also include one or more soil release polymers which aid the removal of soils from fabrics such as cotton and polyester based fabrics, in particular the removal of hydrophobic soils from polyester based fabrics. The soil release polymers may for example be non-ionic or anionic terephthalate-based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents:

The detergent compositions may also include one or more anti-redeposition agents such as carboxymethylcellulose (CMC), polyvinyl alcohol (PVA), polyvinylpyrrolidone (PVP), poly-oxyethylene and/or polyethyleneglycol (PEG), homopolymers of acrylic acid, copolymers of acrylic acid and maleic acid, and ethoxylated polyethyleneimines. The cellulose-based polymers described under soil release polymers above may also function as anti-redeposition agents.

Other Suitable Adjunct Materials Include, but are not Limited to, Anti-Shrink Agents, Anti-Wrinkling Agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Non-limiting films are polymeric materials, such as polymers which are formed into a film or sheet. Non-limiting polymers, copolymers or derivates therof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, such as polyvinyl alcohol copolymers and, hydroxypropyl methyl cellulose (HPMC). In a non-limiting embodiment, the level of polymer in the film for example PVA is at least about 60%. Non-limiting average molecular weight will typically be about 20,000 to about 150,000. Films can also be of blend compositions comprising hydrolytically degradable and water-soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids. Ref: (US2009/0011970 A1).

Detergent ingredients can be separated physically from each other by compartments in water dissolv-able pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycar-bonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two-stage vacuum plodder, extruders, cutters, logo-stampers, cooling tunnels and wrappers. The invention is not limited to preparing the laundry soap bars by any single method. The premix may be added to the soap at different stages of the process. For example, the premix containing a soap, an enzyme, optionally one or more additional enzymes, a protease inhibitor, and a salt of a monovalent cation and an organic anion may be prepared, and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Method of Producing the Composition

The method may be relevant for the (storage) stability of the detergent composition: e.g. Soap bar premix method WO2009155557.

Uses

The detergent compositions may be used for example in any detergent application which requires the degradation of xanthan gum.

Use to Degrade Xanthan Gum

Xanthan gum has been used as an ingredient in many consumer products including foods and cosmetics and has found use in the oil industry. Therefore, the degradation of xanthan gum can result in improved cleaning processes, such as the easier removal of stains containing gums, such as xanthan gum. Thus, use of detergent compositions comprising GH9 endoglucanases (e.g. variants described herein) may degrade xanthan gum. The use of xanthan lyases in the detergent compositions may degrade xanthan gum. An embodiment is the use of GH9 endoglucanases as described herein (e.g. variants) together with xanthan lyases in detergent compositions to degrade xanthan gum. Degradation of xanthan gum can be measured using the viscosity reduction assay (e.g., ViPr assay) or alternatively as described in example 3 herein.

GH9 endoglucanase activity may alternatively be measured by assessment of reducing ends on xanthan gum pre-treated with xanthan lyase using the colorimetric assay developed by Lever (1972), *Anal. Biochem.* 47: 273-279, 1972. A non-limiting embodiment is the use of 0.1% xanthan gum pre-treated with xanthan lyase. Degradation of xanthan gum pre-treated with xanthan lyase may be determined by calculating difference between blank and sample, wherein a difference of more than 0.5 mAU, more than 0.6 mAU, more than 0.7 mAU or more than 0.8 mAU, shows degradation of xanthan gum pre-treated with xanthan lyase.

Xanthan lyase activity may alternatively be measured by assessment of reducing ends liberated from xanthan gum using the colorimetric assay developed by Lever (1972), *Anal. Biochem.* 47: 273-279, 1972. A non-limiting embodiment is the use of 0.1% xanthan gum. Degradation of xanthan gum may be determined by calculating difference between blank and sample wherein a difference of more than 0.1 mAU, more than 0.15 mAU, more than 0.2 mAU or more than 0.25 mAU shows degradation of xanthan gum.

GH9 endoglucanase and xanthan lyase activity may alternatively be measured by assessment of reducing ends liberated from xanthan gum using the colorimetric assay developed by Lever (1972), *Anal. Biochem.* 47: 273-279, 1972. A non-limiting embodiment is the use of 0.1% xanthan gum. Degradation of xanthan gum may be determined by calculating difference between blank and sample wherein a difference of more than 0.4 mAU, more than 0.5 mAU, more than 0.6 mAU or more than 0.8 mAU shows degradation of xanthan gum.

The invention also relates to methods for degrading xanthan gum comprising applying a detergent composition comprising one or more GH9 endoglucanases as described herein (e.g. variants) to xanthan gum. An embodiment is a method for degrading xanthan gum comprising applying a detergent composition comprising one or more GH9 endoglucanases as described herein (e.g. variants) together with one or more xanthan lyases to xanthan gum.

Use in Detergents

GH9 endoglucanases as described herein may be used in detergent compositions for cleaning processes such as the laundering of textiles and fabrics (e.g. household laundry washing and industrial laundry washing), as well as household and industrial hard surface cleaning, such as dish wash. The GH9 endoglucanases as described herein may be added to a detergent composition comprising of one or more detergent components.

In some aspects, GH9 endoglucanases as described herein may be used together with a xanthan lyase(s) in detergent compositions for cleaning processes such as the laundering of textiles and fabrics (e.g. household laundry washing and industrial laundry washing), as well as household and industrial hard surface cleaning, such as dish wash. The GH9 endoglucanases as described herein together with a xanthan lyase(s) may be added to a detergent composition comprising of one or more detergent components.

The polypeptides described herein (e.g. variants) may be added to and thus become a component of a detergent composition. The detergent composition may be formulated, for example, as a hand or machine laundry detergent composition for both household and industrial laundry cleaning, including a laundry additive composition suitable for pre-treatment of stained fabrics and a rinse added fabric softener composition, or be formulated as a detergent composition for use in general household or industrial hard surface cleaning operations, or be formulated for hand or machine (both household and industrial) dishwashing operations. In a specific aspect, a detergent additive may include a polypeptide as described herein.

The invention also relates to methods for degrading xanthan gum on the surface of a textile or hard surface, such as dish wash, comprising applying a detergent composition comprising one or more GH9 endoglucanases as described herein (e.g. variants) to xanthan gum. In some aspects, the invention relates a method for degrading xanthan gum on the surface of a textile or hard surface, such as dish wash, comprising applying a detergent composition comprising one or more GH9 endoglucanases as described herein (e.g. variants) together with one or more xanthan lyases to xanthan gum. In some aspects, the invention relates to a detergent composition comprising one or more detergent components as described herein. Also encompassed is the use of GH9 endoglucanases having an enzyme detergency benefit in the detergent compositions.

It has been contemplated that the use of a GH9 endoglucanase as described herein (e.g., a) alone gives an enzyme detergency benefit, an enzyme detergency benefit on xanthan gum.

In some aspects, the invention relates to the use of a detergent composition comprising one or more detergent components and an isolated GH9 endoglucanase as described herein (e.g. a variant) together with a xanthan lyase. In some aspects, the invention relates to the use of a detergent composition comprising one or more detergent components and an isolated GH9 endoglucanase (e.g. a variant) together with a xanthan lyase.

1. A detergent composition comprising an endoglucanase variant, comprising an alteration (e.g., a substitution, deletion or insertion) at one or more positions in a region selected from the group consisting of:
 i) region 1 corresponding to amino acids 95 to 105 of SEQ ID NO: 2, e.g., said alteration at one or more positions selected from the group consisting of positions: 95, 96, 97, 98, 99, 100, 101, 102, 103, 104, 105, wherein said positions correspond to amino acid positions of SEQ ID NO: 2 (e.g., using the numbering of SEQ ID NO: 2),
 ii) region 2 corresponding to amino acids 115 to 138 of SEQ ID NO: 2, e.g., said alteration at one or more positions selected from the group consisting of positions: 115, 116, 117, 118, 119, 120, 121, 122, 123, 124, 125, 126, 127, 128, 129, 130, 131, 132, 133, 134, 135, 136, 137, 138, wherein said positions correspond to amino acid positions of SEQ ID NO: 2 (e.g., using the numbering of SEQ ID NO: 2),
 iii) region 3 corresponding to amino acids 210 to 251 of SEQ ID NO: 2, e.g., said alteration at one or more positions selected from the group consisting of positions: 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, wherein said positions correspond to amino acid positions of SEQ ID NO: 2 (e.g., using the numbering of SEQ ID NO: 2), iv) region 4 corresponding to amino acids 267 to 301 of SEQ ID NO: 2, e.g., said alteration at one or more positions selected from the group consisting of positions: 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, wherein said positions correspond to amino acid positions of SEQ ID NO: 2 (e.g., using the numbering of SEQ ID NO: 2), v) region 5 corresponding to amino acids 339 to 361 of SEQ ID NO: 2, e.g., said alteration at one or more positions selected from the group consisting of positions: 339, 340, 341, 342, 343, 344, 345, 346, 347, 348, 349, 350, 351, 352, 353, 354, 355, 356, 357, 358, 359, 360, 361, wherein said positions correspond to amino acid positions of SEQ ID NO: 2 (e.g., using the numbering of SEQ ID NO: 2), vi) region 6 corresponding to amino acids 547 to 595 of SEQ ID NO: 2, e.g., said alteration at one or more positions selected from the group consisting of positions: 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, wherein said positions correspond to amino acid positions of SEQ ID NO: 2 (e.g., using the numbering of SEQ ID NO: 2), vii) region 7 corresponding to amino acids 612 to 660 of SEQ ID NO: 2, e.g., said alteration at one or more positions selected from the group consisting of positions: 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, wherein said positions correspond to amino acid positions of SEQ ID NO: 2 (e.g., using the numbering of SEQ ID NO: 2), viii) region 8 corresponding to amino acids 806 to 828 of SEQ ID NO: 2, e.g., said alteration at one or more positions selected from the group consisting of positions: 806, 807, 808, 809, 810, 811, 812, 813, 814, 815, 816, 817, 818, 819, 820, 821, 822, 823, 824, 825, 826, 827, 828, wherein said positions correspond to amino acid positions of SEQ ID NO: 2 (e.g., using the numbering of SEQ ID NO: 2), and ix) region 9 corresponding to amino acids 839 to 1042 of SEQ ID NO: 2, e.g., said alteration at one or more positions selected from the group consisting of positions: 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, wherein said positions correspond to amino acid positions of SEQ ID NO: 2 (e.g., using the numbering of SEQ ID NO: 2), wherein said variant has at least 60%, e.g., at least 70%, at least 75%, at least 80%, at least 85%, at least 90%, at least 95%, at least 96%, at least 97%, at least 98%, or at least 99%, and less than 100% sequence identity to SEQ ID NO: 2; preferably said endoglucanase variant has activity on xanthan gum pre-treated with xanthan lyase, further preferably said activity is a xanthan gum degrading activity.

2. The detergent composition comprising an endoglucanase variant of paragraph 1, which is a variant of a parent endoglucanase selected from the group consisting of:
   a) a polypeptide having at least 60% sequence identity to the mature polypeptide of SEQ ID NO: 2;
   b) a polypeptide encoded by a polynucleotide that hybridizes under low stringency conditions with (i) the mature polypeptide coding sequence of SEQ ID NO: 1, or (ii) the full-length complement of (i);
   c) a polypeptide encoded by a polynucleotide having at least 60% identity to the mature polypeptide coding sequence of SEQ ID NO: 1; and
   d) a fragment of the mature polypeptide of SEQ ID NO: 2, which has endoglucanase activity.

3. The detergent composition comprising an endoglucanase variant of paragraph 2, wherein the parent endoglucanase having at least 60%, e.g., at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO: 2.

4. The detergent composition comprising an endoglucanase variant of any of paragraphs 2-3, wherein the parent endoglucanase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1 or (ii) the full-length complement of (i).

5. The detergent composition comprising an endoglucanase variant of any of paragraphs 2-4, wherein the parent endoglucanase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 1.

6. The detergent composition comprising an endoglucanase variant of any of paragraphs 2-5, wherein the parent endoglucanase comprises or consists of the mature polypeptide of SEQ ID NO: 2.

7. The detergent composition comprising an endoglucanase variant of any of paragraphs 2-6, wherein the parent endoglucanase is a fragment of the mature polypeptide of SEQ ID NO: 2, wherein the fragment has endoglucanase activity.

8. The detergent composition comprising an endoglucanase variant of any of paragraphs 2-7, which has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent endoglucanase.

9. The detergent composition comprising an endoglucanase variant of any of paragraphs 1-8, wherein said variant has at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

10. The detergent composition comprising an endoglucanase variant of any of paragraphs 1-9, wherein said alteration at one or more positions is selected from the group consisting of alterations in positions: 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 603, 605, 609, 676, 688, 690, 694, 697, 698, 699, 711, 719, 754, 756, 760, 781, 786, 797, 833, 834, 835 and 1048 of SEQ ID NO: 2, wherein numbering is according to SEQ ID NO: 2.

11. The detergent composition comprising an endoglucanase variant of any of paragraphs 1-10, wherein said alteration at one or more positions is selected from the group consisting of: 517A, F20P, F20N, F20G, F20Y, K51Q, K51H, E53P, E53G, Y55M, V56M, Y60F, S63F, T87R, A186P, K192N, I302D, I302H, I302V, I302M, H311N, S313D, I387T, K388R, K390Q, I403Y, E408D, E408S, E408P, E408A, E408G, E408N, P410G, Q416S, Q416D, A448E, A448W, A448S, K451S, G471S, S472Y, D476R, Q489P, K507R, K512S, S515V, S538C, Y579W, S598Q, A599S, I602T, I602D, V603P, S605T, G609E, D676H, A688G, Y690F, T694A, T697G, R698W, T699A, T711V, T711Y, W719R, K754R, V756H, V756Y, S760G, T781M, N786K, T797S, A824D, N833D, Q834E, S835D and F1048W of SEQ ID NO: 2.

12. The detergent composition comprising an endoglucanase variant according to any one of paragraphs 1-11, wherein the variant further comprises an alteration at one or more positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999 and 1037.

13. The detergent composition comprising an endoglucanase variant according to any one of paragraphs 1-12, further wherein said alteration at one or more positions is selected from the group consisting of: N216D, N216Q, A283D, A346D, A559P, A559N, A564E, Y579W, S636K, S636N, F638N, A651P, A824D, N848D, A869V, R880K, V881T, V881Q, T883R, T887K, T892P, N905D, F906A, A912V, K921R, S928D, Y934G, A937E, K948R, Q956Y, T999R, and A1037E.

14. The detergent composition comprising an endoglucanase variant according to any one of claims 1-13, wherein the variant comprises one or more of the following set of substitutions:

| |
|---|
| F20Y + A448S + T781M |
| E408D + K451S |
| E408D + A448E |
| E408D |
| Y579W + E408D |

15. The detergent composition comprising an endoglucanase variant according to any one of claims 1-14, wherein the variant comprises one or more of the following set of substitutions:

| |
|---|
| S17A, F20P, N216D, A283D, H311N, E408D, Y579W, I602T, A651P, A688G, T883R, F906A, Y934G, Q956Y |
| F20P, I302D, S313D, E408D, D476R, Y579W, S636K, T697G, V756Y, V881Q, T887K, F906A, A937E |
| F20P, S313D, E408D, Y579W, S636K, A688G, T697G, N905D, A937E |
| F20P, I302D, S313D, E408D, D476R, Y579W, S636K, T697G, W719R, V756Y, V881Q, T887K, F906A, A937E |
| N216Q, S313D, E408D, D476R, Y579W, I602T, F638N, A651P, T697G, W719R, R880K, T887K, K921R, Y934G |
| N216D, S313D, E408D, D476R, A564E, Y579W, I602T, F638N, A651P, Y690F, T697G, W719R, V756H, N833D, A869V, R880K, V881T, T887K, K921R, S928D, Y934G, T999R |
| F20P, I302D, S313D, E408D, D476R, Y579W, S636K, T697G, W719R, V756Y, N848D, A869V, V881Q, T887K, N905D, F906A, Q912V, A937E, T999R, F1048W |
| F20P, I302D, S313D, E408D, D476R, Q489P, Y579W, S636N, T697G, W719R, V756Y, A824D, N848D, V881Q, T887K, F906A, S928D, A937E |
| F20P, I302D, S313D, E408D, Q416S, D476R, Q489P, Y579W, I602T, S636K, A651P, T697G, W719R, V756Y, A824D, N833D, N848D, T883R, T887K, F906A, A937E |
| F20P, A186P, I302D, S313D, E408D, D476R, Q489P, Y579W, A599S, I602T, S636K, A651P, T697G, W719R, V756Y, N848D, T883R, T887K, F906A, A937E |
| N216D, S313D, E408D, D476R, Y579W, I602T, V603P, F638N, A651P, A688G, T697G, W719R, V756H, R880K, T887K, K921R, S928D, Y934G, K948R |
| F20P, K51Q, I302D, S313D, E408D, D476R, Q489P, Y579W, I602T, S636K, A651P, T697G, W719R, V756Y, N848D, T883R, T887K, F906A, A937E |
| F20P, I302D, S313D, A346D, E408D, D476R, Q489P, Y579W, S636N, T697G, W719R, V756Y, A824D, N848D, V881Q, T887K, F906A, A937E, T999R |
| F20P, I302D, S313D, E408D, D476R, Q489P, Y579W, I602T, S636N, T697G, W719R, V756Y, A824D, N848D, V881Q, T887K, N905D, F906A, A937E, T999R, A1037E, F1048W |
| F20P, K51Q, I302D, S313D, E408D, D476R, Q489P, Y579W, I602T, S636K, A651P, T697G, W719R, V756Y, A824D, N848D, T883R, T887K, F906A, S928D, A937E, A1037E |
| N216D, S313D, A346D, E408D, D476R, Q489P, A559P, Y579W, I602T, F638N, A651P, A688G, T697G, W719R, V756H, R880K, T887K, K921R, S928D, Y934G |
| F20P, I302D, S313D, A346D, E408D, D476R, Q489P, Y579W, I602T, T697G, W719R, V756Y, N848D, V881Q, T887K, F906A, A937E |
| N216D, S313D, E408D, D476R, Q489P, A559P, Y579W, I602T, F638N, A651P, A688G, T697G, W719R, V756H, Q834E, R880K, T887K, T892P, K921R, S928D, Y934G |
| F20P, I302D, S313D, E408D, D476R, Q489P, A559N, Y579W, I602T, S636K, A651P, T697G, W719R, V756Y, N848D, T883R, T887K, F906A, S928D, A937E |
| F20P, I302D, S313D, E408D, D476R, Q489P, Y579W, I602T, S636K, A651P, T697G, W719R, V756Y, N848D, T883R, T887K, F906A, A937E |
| F20P, I302D, S313D, E408D, Q416S, D476R, Q489P, A559N, Y579W, I602T, S636K, A651P, T697G, W719R, V756Y, N848D, T883R, T887K, F906A, A937E |
| F20P, I302D, S313D, E408D, D476R, Y579W, I602T, S636N, T697G, W719R, V756Y, A824D, N848D, V881Q, T887K, F906A, S928D, A937E, T999R, F1048W |

16. The detergent composition comprising an endoglucanase variant of any of paragraphs 1-15, wherein the total number of alterations compared to the parent endoglucanase (e.g., SEQ ID NO: 2) is between 1 and 25, e.g., between 1 and 20, e.g., between 1 and 10 or between 1 and 5, such as 1, 2, 3, 4, 5, 6, 7, 8, 9 or 10 alterations.

17. The detergent composition comprising an endoglucanase variant of any of paragraphs 1-16, wherein said activity on xanthan gum pre-treated with xanthan lyase is a xanthan degrading activity, preferably said xanthan degrading activity is endoglucanase EC 3.2.1.4 activity.

18. The detergent composition comprising an endoglucanase variant of any of paragraphs 1-17, wherein said variant has an improved stability in a detergent composition compared to a parent endoglucanase (e.g., with SEQ ID NO: 2).

19. The detergent composition comprising an endoglucanase variant of any of paragraphs 1-18, wherein said variant has a half-life improvement factor (HIF) of 1.0; preferably said variant has a half-life improvement factor (HIF) of >1.0 relative to a parent endoglucanase, e.g. an endoglucanase of SEQ ID NO: 2.
20. The detergent composition comprising an endoglucanase variant of paragraph 19, wherein said half-life improvement factor (HIF) is determined after incubation of said endoglucanase variant in a detergent composition at 25° C. for a time period from about 5 to about 140 hours.
21. The detergent composition of any of paragraphs 1-20, further comprising one or more detergent components.
22. The detergent composition of any of paragraphs 1-21 further comprising one or more additional enzymes selected from the group consisting of: endoglucanases, proteases, amylases, lichenases, lipases, cutinases, cellulases, xanthan lyases, xyloglucanases, pectinases, pectin lyases, xanthanases, peroxidases, haloperoxygenases, catalases and mannanases, or any mixture thereof.
23. The detergent composition of any of paragraphs 1-22, further comprising an endoglucanase, such as xanthan endoglucanase.
24. The detergent composition of any of paragraphs 1-23, wherein said composition is in form of a bar, a homogenous tablet, a tablet having two or more layers, a pouch having one or more compartments, a regular or compact powder, a granule, a paste, a gel, or a regular, compact or concentrated liquid.
25. Use of a detergent composition of any of paragraphs 1-24 for degrading xanthan gum.
26. The use of paragraph 25, wherein said endoglucanase variant has an enzyme detergency benefit.
27. A method for degrading xanthan gum comprising: applying a detergent composition of any of paragraphs 1-24 to a xanthan gum.
28. The method of paragraph 27, wherein said xanthan gum is on a surface or hard surface.

EXAMPLES

Example 1: Construction of GH9 Endoglucanase Variants of the Mature Parent Endoglucanase Having SEQ ID NO: 2

A linear integration vector-system was used for cloning of the mature parent nucleotide sequence having SEQ ID NO: 1 (same also disclosed as mature peptide within SEQ ID NO: 1 of WO 2013/167581A1) coding for the mature parent polypeptide of the GH9 endoglucanase of SEQ ID NO: 2, and its variants. The linear integration construct was a PCR fusion made by fusing the gene between two *Bacillus subtilis* homologous chromosomal regions along with strong promoters and a chloramphenicol resistance marker. The fusion was made by Splicing by Overlap Extension (SOE) PCR (Horton, R. M, Hunt, H. D., Ho, S. N., Pullen, J. K. and Pease, L. R. (1989). Engineering hybrid genes without the use of restriction enzymes, or gene splicing were produced by overlap extension (Gene 77: 61-68). The SOE PCR method is also described in patent application WO 2003/095658. The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for chloramphenicol acetyltransferase was used as marker (described in e.g. Diderichsen, B.; Poulsen, G. B.; Joergensen, S.T.; A useful cloning vector for *Bacillus subtilis*. Plasmid 30:312, 1993). The final gene constructs were integrated on the *Bacillus* chromosome by homologous recombination into the pectate lyase locus. The gene fragments were amplified from chromosomal DNA of the corresponding strains with gene specific primers containing overhang to the two flanking vector fragments. All genes were expressed with a *Bacillus licheniformis* alpha-amylase secretion signal having the nucleotide sequence of SEQ ID NO: 3 and the amino acid sequence of SEQ ID NO: 4 replacing the native secretion signal.

Variants of the mature parent GH9 endoglucanase from *Paenibacillus* sp-62047 having SEQ ID NO: 2 as described in Examples 3-4 below were made by the megaprimer mutagenesis method using specifically designed mutagenic oligonucleotides introducing desired mutations in the resulting sequence. Design and production methods for such mutagenic oligonucleotides introducing desired mutations into target sequences are well known to those skilled in the art. Consequently, mutagenic oligos were designed and synthesized corresponding to the DNA sequence flanking the desired site(s) of mutation, separated by the DNA base pairs defining the substitutions. The final expression cassette composed the reference GH9 endocluconase from *Paenibacillus* sp-62047 as described above (i.e., parent GH9 endocluconase having SEQ ID NO: 1). Successful introduction of the desired substitutions was confirmed by DNA sequencing of the GH9 endoglucanase gene. An aliquot of the PCR product was subsequently transformed into *Bacillus subtilis*. Transformants were selected on LB agar plates supplemented with 10 mM K2PO4, 0.4% extra glucose and 6 µg of chloramphenicol per ml. The resulting recombinant *Bacillus subtilis* clone containing the integrated expression construct was grown in liquid culture as described below. The enzyme containing supernatants were harvested and the enzymes (variants) were either stress tested using a reducing sugar assay or purified as described below.

Variants above were produced by fermentation using standard protocols (TB-glycerol media containing a standard trace metal mix as described in F. William Studier, "Protein production by auto-induction in high-density shaking cultures", Protein Expression and Purification, 41 (2005) 207-234) and grown for 4 days at 30° C. before harvested). Supernatants of samples used for stress testing were inoculated from an overnight culture grown at 37° C. and subsequently fermented in 96-well plate format (TB-glycerol media described above without calcium in the trace metal mix for 4 days 30° C.).

Example 2: Purification of GH9 Endoglucanase Variants

The culture broth was centrifuged at 13'000 rpm (45 min, 18° C., F12S-6×500 rotor) using a Sorval RC-6 plus centrifuge (ThermoFisher Scientific). The supernatant was supplemented with $(NH_4)_2SO_4$ to a final concentration of 0.8 M. The mixture was filtered using 0.2 µm bottle-top rapid flow filters (Nalgene). The mixture was loaded on a 50 mL Phenyl Sepharose High Performance (GE Healthcare, Uppsala, Swe-den) pre-equilibrated with 20 mM Tris-HCl, pH 8.0 with 0.8 M $(NH_4)_2SO_4$. Flowrate was set to 3 mL/min. After protein loading, the flow rate was increased to 5 mL/min and unbound or loosely bound protein was washed out by several column volumes of equilibration buffer. Elution was carried out by step-wise increase of elution buffer (20 mM Tris-HCl, pH 8.0). The target protein eluted during the (75-100%) elution step. Fractions of 8 mL were collected during the purification. The fractions were evaluated using SDS-PAGE (NuPAGE, Invitrogen). Fractions eluting with 20 mM Tris-HCl, pH 8.0 were pooled and desalted on a 350 mL G25 desalting column pre-equilibrated with 20 mM Tris-HCl, pH 8.5. The desalted protein solution was applied on a 20 mL Source15Q column pre-equilibrated with 20 mM Tris-HCl, pH 8.5 at 2 mL/min. Unbound or loosely bound proteins were washed using at least two column volumes of equilibration buffer until a stable UV baseline was obtained. The flow rate was raised to 4 mL/min and elution was done by a linear NaCl gradient using the elution buffer (20 mM Tris-HCl, pH 8.5+750 mM NaCl). 3 mL fractions were collected during the purification. SDS-PAGE was used to evaluate the fractions. Pure fractions were pooled and concentrated if necessary using Vivaspin 20 (10 kDa Cut-off, Sartorius). Protein concentration was determined using absorbance measurements at 280 nm.

Example 3: Detergent Stability Assay

GH9 endoglucanase (EG) activity (EC 3.2.1.4) was determined by reducing ends on xanthan gum pre-treated with xanthan lyase using the colorimetric assay developed by Lever (1972), Anal. Biochem. 47: 273-279, 1972. Pre-treated xanthan gum is a modified form of the xanthan sugar, where the terminal pyruvated mannose from side chains is removed (prepared according to Nankai et al. (1999) from the source Keltran). The GH9 mature parent endoglucanase and its variants cleave at beta(1,4)-glucosyl bonds in the glucan backbone of pre-treated xanthan gum releasing glucans with a reducing end which can be determined by reaction with p-Hydroxybenzoic acid hydrazide (PAHBAH). The increase of colour is proportional to the enzyme activity under the conditions used in the assay (e.g., Table 1) and used to estimate the residual activity (RA), half-life (T1l2) and the half-life improvement factor (HIF).

TABLE 1

Description of assays

| Stress assay: | |
|---|---|
| Detergent | Persil Universal Gel |
| Assay buffer (AB) | 50 mM MOPS, 4 mM CaCl$_2$, 0.01% Triton X-100, pH 7.0 |
| Reference sample conditions | 4° C. for 5-138 hours |
| Stress conditions | 25, 26, 28 or 30° C. for 5-138 hours |
| Activity assay: | |
| Substrate concentration | 4 mg/mL modified xanthan gum |
| Xanthan gum incubation | 50° C. for 1 h |
| PAHBAH solution | 15 mg/mL 4-hydroxybenzoic acid hydrazide (PAHBAH), 50 g/L potassium sodium tartrate tetrahydrate, 20 g/L NaOH |
| PAHBAH development | 95° C. for 10 min |

Method Steps:

30 µL enzyme sample (purified variant, 10-150 ppm) was mixed with 270 µL detergent using magnetic stirring for 15 minutes in a micro titer plate (MTP). This plate was designated as the "stress MTP". 20 µL of the mixture was transferred to a new MTP and diluted 100-fold using a 2-step dilution (2×10-fold dilution). The sample was diluted into assay buffer (AB): 50 mM MOPS, 4 mM CaCl$_2$), 0.01% Triton X-100, pH 7.0. This diluted MTP is the "reference MTP" and is stored at 4° C. for 5-138 h (at a time interval equal to that of the stress MTP below). The stress MTP was incubated at 25, 26, 28 or 30° C. for 5-138 h. After incubation, the stress MTP was initially mixed by magnetic stirring for 15 minutes, and the stress MTP was then diluted 100-fold as described for the reference MTP. To assess the enzymatic activity, 50 µL of diluted enzyme:detergent sample (from both reference and stress MTPs) was mixed with 50 µL 4 mg/mL modified xanthan gum in PCR plates. The samples were then incubated at 50° C. for 1 h. Finally, the level of reducing ends was estimated by adding 75 µL PAHBAH solution (15 mg/mL PAHBAH, 50 g/L potassium sodium tartrate tetrahydrate, 20 g/L NaOH) to all samples in the PCR plates. The samples were then incubated at 95° C. for 10 min. After cooling down to room temperature, the absorbance at 405 nm was measured. The residual activity (RA) was calculated using the following formula:

$$RA\ (\%) = (Abs(Stress))/(Abs(Ref)) \times 100\%$$

Abs(Stress): The absorbance at 405 nm of the sample in the stress MTP (incubated at 25, 26, 28 or 30° C.) after subtracting relevant background absorbance contributions.

Abs(Ref): The absorbance at 405 nm of the sample in the reference MTP (incubated at 4° C.).

Also, the half-lives for the degradation of each variant and parent endoglucanase were calculated using the following formula (by applying 1st order kinetics for the degradation of EG):

$$T1/2 = -\frac{\ln(2) \times T}{\ln\left(\frac{Abs(Stress)}{Abs(Ref)}\right)}$$

T: The incubation time.

Abs(Stress) and Abs(Ref): See above.

Half-life improvement factors (HIFs) can then be calculated as:

$$HIF = \frac{T1/2,\ variant}{T1/2,\ wt}$$

T1/2, variant: The half-life for a specific variant

T1/2, wt (or wild-type): The half-life for EG wt (EG wild type), wherein said T1/2 wt is T1/2 of the mature parent endoglucanase with SEQ ID NO: 2.

The HIFs of the tested purified variants are shown in Tables 2-5 below. HIFs in Tables 3-5 were calculated in the same way as in Table 2 except for a slightly increased incubation temperature for variants and controls (26-30 degrees Celsius). All half-life values of the purified variants were calculated relative to the half-life of GH9 wild-type (mature parent endoglucanase with SEQ ID No: 2) incubated at the same detergent concentration and temperature measured as purified protein. HIF of GH9 wild-type in all tables is 1 (per definition).

TABLE 2

Purified variants of the mature parent GH9 endoglucanase (SEQ ID NO: 2) with corresponding half-life improvement factors (HIF) incubated at 25° C. relative to a parent endoglucanase, e.g. an endoglucanase of SEQ ID NO: 2.

| Alteration as compared to SEQ ID NO: 2 | PUG (detergent concentration) | Incubation time (hrs) | HIF |
|---|---|---|---|
| K507R | 90% PUG | 16 | 1.1 |
| S17A | 90% PUG | 16 | 1.1 |
| S63F | 90% PUG | 16 | 1.1 |
| T694A | 90% PUG | 16 | 1.1 |
| F20Y + A448S + T781M | 90% PUG | 16 | 1.3 |
| Q834E | 90% PUG | 16 | 1.3 |
| V56M | 90% PUG | 16 | 1.3 |
| I602T | 90% PUG | 18 | 1.4 |
| A448E | 90% PUG | 16 | 1.4 |
| A448W | 90% PUG | 16 | 1.5 |
| F20G | 90% PUG | 16 | 1.5 |
| I403Y | 90% PUG | 16 | 1.5 |
| S538C | 90% PUG | 16 | 1.5 |
| E408N | 90% PUG | 16 | 2.2 |
| F20N | 90% PUG | 16 | 2.4 |
| K512P | 90% PUG | 16 | 2.5 |
| E408G | 90% PUG | 16 | 2.9 |
| P410G | 90% PUG | 16 | 2.9 |
| E408A | 90% PUG | 16 | 3.0 |
| F20P | 90% PUG | 16 | 3.3 |
| E408P | 90% PUG | 16 | 4.2 |
| E408S | 90% PUG | 16 | 5.4 |

TABLE 3

Purified variants of the mature parent GH9 endoglucanase (SEQ ID NO: 2) with corresponding half-life improvement factors (HIF) incubated at 26° C. relative to a parent endoglucanase, e.g. an endoglucanase of SEQ ID NO: 2.

| Alteration as compared to SEQ ID NO: 2 | PUG (detergent concentration) | Incubation time (hrs) | HIF |
|---|---|---|---|
| I302H | 90% PUG | 17.25 | 1.1 |
| I387T | 90% PUG | 19.5 | 1.1 |
| K51H | 90% PUG | 19.5 | 1.1 |
| K754R | 90% PUG | 19.5 | 1.1 |
| K390Q | 90% PUG | 18 | 1.2 |
| S605T | 90% PUG | 18.5 | 1.3 |
| I602D | 90% PUG | 18.5 | 1.3 |
| K51Q | 90% PUG | 18 | 1.6 |
| Y55M | 90% PUG | 18 | 1.6 |
| K451S | 90% PUG | 18 | 1.9 |
| Q416S | 90% PUG | 18 | 2.2 |
| Q416D | 90% PUG | 18 | 2.5 |

TABLE 4

Purified variants of the mature parent GH9 endoglucanase (SEQ ID NO: 2) with corresponding half-life improvement factors (HIF) incubated at 28° C. relative to a parent endoglucanase, e.g. an endoglucanase of SEQ ID NO: 2.

| Alteration as compared to SEQ ID NO: 2 | PUG (detergent concentration) | Incubation time (hrs) | HIF |
|---|---|---|---|
| K388R | 90% PUG | 5 | 1.3 |
| T711Y | 90% PUG | 5.5 | 1.8 |
| T711V | 90% PUG | 5.5 | 1.9 |

TABLE 5

Purified variants of the mature parent GH9 endoglucanase (SEQ ID NO: 2) with corresponding half-life improvement factors (HIF) incubated at 30° C. relative to a parent endoglucanase, e.g. an endoglucanase of SEQ ID NO: 2.

| Alteration as compared to SEQ ID NO: 2 | PUG (detergent concentration) | Incubation time (hrs) | HIF |
|---|---|---|---|
| E408D + K451S | 90% PUG | 16 | 26.1 |
| E408D + A448E | 90% PUG | 16 | 36.3 |
| E408D | 90% PUG | 138 | 53.3 |
| E408D + A448E | 90% PUG | 138 | 53.7 |
| E408D + K451S | 90% PUG | 138 | 57.6 |
| Y579W + E408D | 90% PUG | 138 | 72.5 |

Example 4: Calculating Half-Lives and Half-Life Improvement Factors (HIF) for Xanthan Endoglucanase Variants Half-life (T½ (in hours)) was calculated at a given detergent concentration and storage temperature (Persil Universal Gel (PUG) 95%, 30° C., 4 wk or more) for the wild-type controls and/or variants, as the residual activity follows an exponential decay and the incubation time (hours) is known, i.e., according to the following formulas:

$T_{1/2}(\text{variants}) = (Ln(0.5)/Ln(\text{RA-variants}/100))*\text{Time}$ $T_{1/2}(\text{Wild-type}) = (Ln(0.5)/Ln(\text{RA-wild-type}/100))*\text{Time}$ A half-life improvement factor (HIF) is calculated as HIF=T½ (Variant)/T ½ (Wild-type), where the wild-type is incubated under the same storage condition as the variant.

In the cases where the difference in stability between Wild-type and variants is too big to accurately assess half-life for both Wild-type and variant using the same incubation time, the incubation time for Wild-type and variant is different e.g. 1 h for Wild-type and 672 h for the most stable variants, Half-life Improvement Factor of variants were calculated by HIF=T½ (Variant)/T % (Wild-type) where T½ of the WT was 1.5 hr.

TABLE 6

| Variant # | Mutations | HIF |
|---|---|---|
| 1 | S17A, F20P, N216D, A283D, H311N, E408D, Y579W, I602T, A651P, A688G, T883R, F906A, Y934G, Q956Y | 300 |
| 2 | F20P, I302D, S313D, E408D, D476R, Y579W, S636K, T697G, V756Y, V881Q, T887K, F906A, A937E | 310 |
| 3 | F20P, S313D, E408D, Y579W, S636K, A688G, T697G, N905D, A937E | 375 |
| 4 | F20P, I302D, S313D, E408D, D476R, Y579W, S636K, T697G, W719R, V756Y, V881Q, T887K, F906A, A937E | 442 |
| 5 | N216Q, S313D, E408D, D476R, Y579W, I602T, F638N, A651P, T697G, W719R, R880K, T887K, K921R, Y934G | 521 |
| 6 | N216D, S313D, E408D, D476R, A564E, Y579W, I602T, F638N, A651P, T690F, T697G, W719R, V756H, N833D, A869V, R880K, V881T, T887K, K921R, S928D, Y934G, T999R | 553 |
| 7 | F20P, I302D, S313D, E408D, D476R, Y579W, S636K, T697G, W719R, V756Y, N848D, A869V, V881Q, T887K, N905D, F906A, Q912V, A937E, T999R, F1048W | 557 |
| 8 | F20P, I302D, S313D, E408D, D476R, Q489P, Y579W, S636K, T697G, W719R, V756Y, A824D, N848D, V881Q, T887K, F906A, S928D, A937E | 566 |

TABLE 6-continued

| Variant # | Mutations | HIF |
|---|---|---|
| 9 | F20P, I302D, S313D, E408D, Q416S, D476R, Q489P, Y579W, I602T, S636K, A651P, T697G, W719R, V756Y, A824D, N833D, N848D, T883R, T887K, F906A, A937E | 597 |
| 10 | F20P, A186P, I302D, S313D, E408D, D476R, Q489P, Y579W, I602T, A599S, S636K, A651P, T697G, W719R, V756Y, N848D, T883R, T887K, F906A, A937E | 616 |
| 11 | N216D, S313D, E408D, D476R, Y579W, I602T, V603P, F638N, A651P, A688G, T697G, W719R, V756H, R880K, T887K, K921R, S928D, Y934G, K948R | 622 |
| 12 | F20P, K51Q, I302D, S313D, E408D, D476R, Q489P, Y579W, I602T, S636K, A651P, T697G, W719R, V756Y, N848D, T883R, T887K, F906A, A937E | 640 |
| 13 | F20P, I302D, S313D, A346D, E408D, D476R, Q489P, Y579W, S636N, T697G, W719R, V756Y, A824D, N848D, V881Q, T887K, F906A, A937E, T999R | 644 |
| 14 | F20P, I302D, S313D, E408D, D476R, Q489P, Y579W, I602T, S636N, T697G, W719R, V756Y, A824D, N848D, V881Q, T887K, N905D, F906A, A937E, T999R, A1037E, F1048W | 655 |
| 15 | F20P, K51Q, I302D, S313D, E408D, D476R, Q489P, Y579W, I602T, S636K, A651P, T697G, W719R, V756Y, A824D, N848D, T883R, T887K, F906A, S928D, A937E, A1037E | 658 |
| 16 | N216D, S313D, A346D, E408D, D476R, Q489P, A559P, Y579W, I602T, F638N, A651P, A688G, T697G, W719R, V756H, R880K, T887K, K921R, S928D, Y934G | 663 |
| 17 | F20P, I302D, S313D, A346D, E408D, D476R, Q489P, Y579W, I602T, T697G, W719R, V756Y, N848D, V881Q, T887K, F906A, A937E | 663 |
| 18 | N216D, S313D, E408D, D476R, Q489P, A559P, Y579W, I602T, F638N, A651P, A688G, T697G, W719R, V756H, Q834E, R880K, T887K, T892P, K921R, S928D, Y934G | 679 |
| 19 | F20P, I302D, S313D, E408D, D476R, Q489P, A559N, Y579W, I602T, S636K, A651P, T697G, W719R, V756Y, N848D, T883R, T887K, F906A, S928D, A937E | 693 |
| 20 | F20P, I302D, S313D, E408D, D476R, Q489P, Y579W, I602T, S636K, A651P, T697G, W719R, V756Y, N848D, T883R, T887K, F906A, A937E | 702 |
| 21 | F20P, I302D, S313D, E408D, Q416S, D476R, Q489P, A559N, Y579W, I602T, S636K, A651P, T697G, W719R, V756Y, N848D, T883R, T887K, F906A, A937E | 720 |
| 22 | F20P, I302D, S313D, E408D, D476R, Y579W, I602T, S636N, T697G, W719R, V756Y, A824D, N848D, V881Q, T887K, F906A, S928D, A937E, T999R, F1048W | 769 |

The invention claimed is:

1. A detergent composition comprising an endoglucanase variant, wherein the variant comprises an alteration at one or more positions in a region selected from the group consisting of:
   i) region 10 corresponding to amino acids 1 to 94 of SEQ ID NO: 2,
   ii) region 11 corresponding to amino acids 106 to 114 of SEQ ID NO: 2,
   iii) region 12 corresponding to amino acids 139 to 209 of SEQ ID NO: 2,
   iv) region 13 corresponding to amino acids 252 to 266 of SEQ ID NO: 2,
   v) region 14 corresponding to amino acids 302 to 338 of SEQ ID NO: 2,
   vi) region 15 corresponding to amino acids 362 to 546 of SEQ ID NO: 2,
   vii) region 16 corresponding to amino acids 596 to 611 of SEQ ID NO: 2,
   viii) region 17 corresponding to amino acids 661 to 805 of SEQ ID NO: 2,
   ix) region 18 corresponding to amino acids 829 to 838 of SEQ ID NO: 2,
   x) region 19 corresponding to amino acids 1043 to 1055 of SEQ ID NO: 2, and
   xi) combinations thereof;
   wherein said variant has at least 90% and less than 100% sequence identity to SEQ ID NO: 2; wherein said variant has an improved storage stability in the detergent composition compared to a wild-type endoglucanase having a sequence identity that is identical to SEQ ID NO: 2.

2. The detergent composition comprising an endoglucanase variant according to claim 1, wherein said alteration at one or more positions is selected from the group consisting of alterations in positions: 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 605, 609, 676, 688, 690, 694, 697, 698, 699, 711, 719, 754, 756, 760, 781, 786, 797, 833, 834, 835, 1048, and combinations thereof of SEQ ID NO: 2, wherein numbering is according to SEQ ID NO: 2.

3. The detergent composition comprising an endoglucanase variant according to claim 1, wherein said alteration at one or more positions is selected from the group consisting of: 517A, F20P, F20N, F20G, F20Y, K51Q, K51H, E53P, E53G, Y55M, V56M, Y60F, S63F, T87R, A186P, K192N, I320D, I302H, I302V, I302M, H311N, S313D, I387T, K388R, K390Q, I403Y, E408D, E408S , E408P, E408A, E408G, E408N, P410G, Q416S , Q416D, A448E, A448W, A448S, K451S, G471S, S472Y, D476R, Q489P, K507R, K512P, S515V, S538C, Y579W, S598Q, A599S, I602T, I602D, V603P, 5605T, G609E, D676H, A688G, Y690F, T694A, T697G, R698W, T699A, T711V, T711Y, W719R, K754R, V756H, V756Y, 5760G, T781M, N786K, T797S, A824D, N833D, Q834E, S835D, F1048W, and combinations thereof, wherein numbering is according to SEQ ID NO: 2.

4. The detergent composition comprising an endoglucanase variant according to claim 1, wherein said alteration at one or more positions is selected from the group consisting of alterations in positions: 17, 20, 302, 311, 313, 408, 476, 602, 688, 697, 719, and combinations thereof wherein numbering is according to SEQ ID NO: 2.

5. The detergent composition comprising an endoglucanase variant according to claim 1, wherein said alteration at one or more positions is selected from the group consisting of alterations in positions: S 517A, F20P, I 302D, H311N, S313D, E408D, D476R, I 602T, A688G, T697G, W719R, and combinations thereof wherein numbering is according to SEQ ID NO: 2.

6. The detergent composition comprising an endoglucanase variant according to claim 1, wherein the variant further comprises an alteration at one or more positions selected from the group consisting of alterations in positions: 216, 283, 346, 559, 564, 579, 636, 638, 651, 824, 848, 869, 880, 881, 883, 887, 892, 905, 906, 912, 921, 928, 934, 937, 948, 956, 999, 1037, and combinations thereof wherein numbering is according to SEQ ID NO: 2.

7. The detergent composition comprising an endoglucanase variant according to claim 1, wherein said alteration at one or more positions is selected from the group consisting of: N216D, N216Q, A283D, A346D, A559P, A559N, A564E, Y579W, S636K, S636N, F638N, A651P, A824D, N848D, A869V, R880K, V881T, V881Q, T883R, T887K, T892P, N905D, F906A, A912V, K921R, S928D, Y934G, A937E, K948R, Q956Y, T999R, A1037E, and combinations thereof wherein numbering is according to SEQ ID NO: 2.

8. The detergent composition comprising an endoglucanase variant according to claim 1, wherein the variant comprises one or more of the following set of substitutions:

F20Y + A448S + T781M
E408D + K451S
E408D + A448E
E408D
Y579W + E408D

9. The detergent composition comprising an endoglucanase variant according to claim 1, wherein the variant comprises one or more of the following set of substitutions:

S17A, F20P, N216D, A283D, H311N, E408D, Y579W, I602T, A651P, A688G, T883R, F906A, Y934G, Q956Y
F20P, I302D, S313D, E408D, D476R, Y579W, S636K, T697G, V756Y, V881Q, T887K, F906A, A937E
F20P, S313D, E408D, Y579W, S636K, A688G, T697G, N905D, A937E
F20P, I302D, S313D, E408D, D476R, Y579W, S636K, T697G, W719R, V756Y, V881Q, T887K, F906A, A937E
N216Q, S313D, E408D, D476R, Y579W, I602T, F638N, A651P, T697G, W719R, R880K, T887K, K921R, Y934G
N216D, S313D, E408D, D476R, A564E, Y579W, I602T, F638N, A651P, Y690F, T697G, W719R, V756H, N833D, A869V, R880K, V881T, T887K, K921R, S928D, Y934G, T999R
F20P, I302D, S313D, E408D, D476R, Y579W, S636K, T697G, W719R, V756Y, N848D, A869V, V881Q, T887K, N905D, F906A, Q912V, A937E, T999R, F1048W
F20P, I302D, S313D, E408D, D476R, Q489P, Y579W, S636N, T697G, W719R, V756Y, A824D, N848D, V881Q, T887K, F906A, S928D, A937E
F20P, I302D, S313D, E408D, Q416S, D476R, Q489P, Y579W, I602T, S636K, A651P, T697G, W719R, V756Y, A824D, N833D, N848D, T883R, T887K, F906A, A937E
F20P, A186P, I302D, S313D, E408D, D476R, Q489P, Y579W, A599S, I602T, S636K, A651P, T697G, W719R, V756Y, N848D, T883R, T887K, F906A, A937E
N216D, S313D, E408D, D476R, Y579W, I602T, V603P, F638N, A651P, A688G, T697G, W719R, V756H, R880K, T887K, K921R, S928D, Y934G, K948R
F20P, K51Q, I302D, S313D, E408D, D476R, Q489P, Y579W, I602T, S636K, A651P, T697G, W719R, V756Y, N848D, T883R, T887K, F906A, A937E
F20P, I302D, S313D, A346D, E408D, D476R, Q489P, Y579W, S636N, T697G, W719R, V756Y, A824D, N848D, V881Q, T887K, F906A, A937E, T999R
F20P, I302D, S313D, E408D, D476R, Q489P, Y579W, I602T, S636N, T697G, W719R, V756Y, A824D, N848D, V881Q, T887K, N905D, F906A, A937E, T999R, A1037E, F1048W
F20P, K51Q, I302D, S313D, E408D, D476R, Q489P, Y579W, I602T, S636K, A651P, T697G, W719R, V756Y, A824D, N848D, T883R, T887K, F906A, S928D, A937E, A1037E
N216D, S313D, A346D, E408D, D476R, Q489P, A559P, Y579W, I602T, F638N, A651P, A688G, T697G, W719R, V756H, R880K, T887K, K921R, S928D, Y934G
F20P, I302D, S313D, A346D, E408D, D476R, Q489P, Y579W, I602T, T697G, W719R, V756Y, N848D, V881Q, T887K, F906A, A937E
N216D, S313D, E408D, D476R, Q489P, A559P, Y579W, I602T, F638N, A651P, A688G, T697G, W719R, V756H, Q834E, R880K, T887K, T892P, K921R, S928D, Y934G
F20P, I302D, S313D, E408D, D476R, Q489P, A559N, Y579W, I602T, S636K, A651P, T697G, W719R, V756Y, N848D, T883R, T887K, F906A, S928D, A937E
F20P, I302D, S313D, E408D, D476R, Q489P, Y579W, I602T, S636K, A651P, T697G, W719R, V756Y, N848D, T883R, T887K, F906A, A937E
F20P, I302D, S313D, E408D, Q416S, D476R, Q489P, A559N, Y579W, I602T, S636K, A651P, T697G, W719R, V756Y, N848D, T883R, T887K, F906A, A937E
F20P, I302D, S313D, E408D, D476R, Y579W, I602T, S636N, T697G, W719R, V756Y, A824D, N848D, V881Q, T887K, F906A, S928D, A937E, T999R, F1048W

10. The detergent composition comprising an endoglucanase variant according to claim 1, wherein said endoglucanase variant has activity on xanthan gum pre-treated with xanthan lyase.

11. The detergent composition comprising an endoglucanase variant according to claim 1, wherein said variant has a half-life improvement factor (HIF) of >1.0 relative to the wild-type endoglucanase.

12. A method of washing an article comprising:
applying the detergent composition of claim 1 to an article; wherein the article is a laundry article, a surface, or combinations thereof; and
degrading xanthan gum from the article.

* * * * *